United States Patent
Knappik et al.

(10) Patent No.: US 10,294,306 B2
(45) Date of Patent: May 21, 2019

(54) AFFINITY LIGANDS AND METHODS RELATING THERETO

(71) Applicant: Bio-Rad Laboratories, Inc., Hercules, CA (US)

(72) Inventors: Achim Knappik, Moorenweis (DE); Stefan Paschen, Krailling (DE)

(73) Assignee: Bio-Rad Laboratories, Inc., Hercules, CA (US)

( * ) Notice: Subject to any disclaimer, the term of this patent is extended or adjusted under 35 U.S.C. 154(b) by 141 days.

(21) Appl. No.: 15/166,761

(22) Filed: May 27, 2016

(65) Prior Publication Data

US 2016/0347826 A1  Dec. 1, 2016

Related U.S. Application Data

(60) Provisional application No. 62/167,387, filed on May 28, 2015.

(51) Int. Cl.
| | |
|---|---|
| *C07K 1/22* | (2006.01) |
| *C07K 16/42* | (2006.01) |
| *B01J 20/32* | (2006.01) |
| *B01D 15/38* | (2006.01) |
| *C07K 16/06* | (2006.01) |
| *B01J 20/286* | (2006.01) |

(52) U.S. Cl.
CPC ...... *C07K 16/4283* (2013.01); *B01D 15/3809* (2013.01); *B01J 20/286* (2013.01); *B01J 20/3208* (2013.01); *B01J 20/3274* (2013.01); *C07K 1/22* (2013.01); *C07K 16/065* (2013.01); *C07K 16/4291* (2013.01); *C07K 2317/21* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 6,372,425 B1 | 4/2002 | Arnold et al. | |
| 8,772,018 B2 * | 7/2014 | Bian | B01J 20/103 430/514 |
| 2005/0287604 A1 * | 12/2005 | Bohmer | G01N 33/56966 435/7.2 |
| 2010/0008851 A1 * | 1/2010 | Nicolaides | C07K 16/3084 424/1.49 |
| 2011/0165620 A1 * | 7/2011 | Romijn | C12N 15/67 435/69.1 |
| 2014/0271617 A1 | 9/2014 | Igawa et al. | |
| 2016/0024147 A1 * | 1/2016 | Tustian | C07K 1/22 530/387.3 |

FOREIGN PATENT DOCUMENTS

| | | |
|---|---|---|
| EP | 2868744 A1 | 5/2015 |
| WO | 2004/039337 A2 | 5/2004 |
| WO | 2011/111007 A2 | 9/2011 |
| WO | 2013/138680 A1 | 9/2013 |
| WO | 2014/028354 A1 | 2/2014 |

OTHER PUBLICATIONS

Gupta et al. "Isolation of circulating immune complexes by conglutinin and separation of antigen from dissociated complexes by immobilized protein A" Clin. exp. Immunol. (1981) 46, 919 (Year: 1981).*
Lloyd et al. "Modelling the human immune response: performance of a 10 to 11 human antibody repertoire against a broad panel of therapeutically relevant antigens" Protein Engineering Design and Selection, 22(3), pp. 159-168 (Year: 2009).*
Mimoto, F., et al., "Engineered antibody Fc variant with selectively enhanced FcγRIIb binding over both FcγRIIaR131 and FcγRIIaH131," Protein Engineering, Design & Selection, Jun. 5, 2013, vol. 26, No. 10, pp. 589-598.
International Search Report and Written Opinion dated Oct. 31, 2016 in PCT/US2016/034589, 13 pages.
Partial Supplementary European Search Report in EP Appln. 16800784.7 dated Oct. 26, 2018; 18 pages.

* cited by examiner

*Primary Examiner* — Daniel E Kolker
*Assistant Examiner* — James L Rogers
(74) *Attorney, Agent, or Firm* — Kilpatrick Townsend and Stockton LLP

(57) ABSTRACT

Affinity ligands useful for mild elution affinity chromatography, including affinity ligands specific for immunoglobulins M, A, and E, are disclosed as are method of identifying and using such affinity ligands.

14 Claims, 19 Drawing Sheets
Specification includes a Sequence Listing.

Anti-IgE Antibodies – Heavy Chain CDR Sequences

| Ab Ref | H-CDR1 | SEQ ID | H-CDR2 | SEQ ID | H-CDR3 | SEQ ID |
|---|---|---|---|---|---|---|
| AbD22512 | GYSFSSYWIT | 1 | WMGIIFPDDSYTIYSPSFQG | 18 | MGYYTAGQAHAYDF | 35 |
| AbD22628 | GYTFTGYDIH | 2 | WMGWIAPYNGGTNYAQKFQG | 19 | DMGTSYLPSNWSYPFAY | 36 |
| AbD22629 | GGTFSDYAIS | 3 | WMGGIIPIFGTANYAQKFQG | 20 | SRASYSYGFDY | 37 |
| AbD22630 | GGTFSTYAIS | 4 | WMGGIIPIFGTADYAQKFQG | 21 | SQRGGASVYSYAFDI | 38 |
| AbD22631 | GYSFTSYWIG | 5 | WMGIIDPSNSDTRYSPSFQG | 22 | GRGYSYPFDY | 39 |
| AbD22632 | GDSVSRNSAAWN | 6 | WLGRIQYRSKWNDYAVSVKS | 23 | DSYTSIGGMDI | 40 |
| AbD22633 | GGTFSSYYIH | 7 | WMGGIGPIFGVANYAQKFQG | 24 | DHSYYPVFYFDN | 41 |
| AbD22634 | GFTFSSYVMT | 8 | WVSAISYDGSSTYYADSVKG | 25 | SEYAIVYFDY | 42 |
| AbD22635 | GGTFNSYAIH | 9 | WMGGIAPIFGTANYAQKFQG | 26 | SRTLVSGYYPFDV | 43 |
| AbD22636 | GGTFSDYAIS | 10 | WMGGIEPVFGTAKYAQKFQG | 27 | MGYYPPAGAMDV | 44 |
| AbD22637 | GFTFSSYAIS | 11 | WVSYISSGGSETYYADSVKG | 28 | VRGYYSYPFDV | 45 |
| AbD22638 | GGTFSDYAIS | 12 | WMGGISPDFGTANYAQKFQG | 29 | SIKTYYVYQAFDH | 46 |
| AbD22639 | GFTFSTYAMH | 13 | WVGRIKSKQDGGTTDYAAPVKG | 30 | TRRGTWYRYARSLDV | 47 |
| AbD22640 | GFTFRSHGMS | 14 | WVSTISGSGSNTYYADSVKG | 31 | YAYAAGTIFDV | 48 |
| AbD22641 | GFTFRSHGMS | 15 | WVSTISGSGSNTYYADSVKG | 32 | YAYAAGTIFDV | 49 |
| AbD22642 | GYTFTGYYMS | 16 | WMGYTSPYSGKTNYAQKFQG | 33 | EMGYYQGFDI | 50 |
| AbD22643 | GFTFSDYAIH | 17 | WVGRIKSHAYGGTTDYAAPVKG | 34 | ESYFDY | 51 |

FIG. 1A

Anti-IgE Antibodies – Light Chain CDR Sequences

| Ab Ref. | L-CDR1 | SEQ ID | L-CDR2 | SEQ ID | L-CDR3 | SEQ ID |
|---|---|---|---|---|---|---|
| AbD22512 | SGDKIGKKYAY | 52 | LVIYSDNNRPS | 69 | YVTDGYFTTG | 86 |
| AbD22628 | SGDNIGSKFAS | 53 | LVIYDDSKRPS | 70 | YSRAQSGSPV | 87 |
| AbD22629 | SGDNLGDKFAH | 54 | LVIYDDNDRPS | 71 | QSYDSSSSLR | 88 |
| AbD22630 | SGDALGTQFAH | 55 | LVIYDIDNKRPS | 72 | QSADWMDY | 89 |
| AbD22631 | SGDALPTMFAH | 56 | LVIYDDNKRPS | 73 | ASYASSLNPV | 90 |
| AbD22632 | SGDSLVKKHAS | 57 | LVIYDDDKRPS | 74 | ASYDGWGNER | 91 |
| AbD22633 | SGDNLGKKYVH | 58 | PVIYDDSKRPS | 75 | QSYDRSLDFN | 92 |
| AbD22634 | RASQGISSYLN | 59 | LLIYSASNLQS | 76 | QQGISWLR | 93 |
| AbD22635 | SGDNLGFKFAH | 60 | LVIYDDSNRPS | 77 | SSYDYSSV | 94 |
| AbD22636 | SGDNIRTQFVQ | 61 | LVIYDDNHRPS | 78 | ASRDKSANSV | 95 |
| AbD22637 | SGDAIGDKFVH | 62 | LVIYDDSKRPS | 79 | QSYDFGGNGI | 96 |
| AbD22638 | SGDALGTKYVH | 63 | LVISDDNERPS | 80 | QSYDFSASSV | 97 |
| AbD22639 | SGSSNIGYNYVS | 64 | LLIYSNTKRPS | 81 | QSRAHGGNSI | 98 |
| AbD22640 | SGSSSNIGANTVS | 65 | LLIYGNIQRPS | 82 | AAYDAIFNKI | 99 |
| AbD22641 | SGSSSNIGANTVS | 66 | LLIYGNIQHPS | 83 | AAYDAIFNKI | 100 |
| AbD22642 | RASQSIINYLN | 67 | LLISDASSLQS | 84 | QQNLSGPF | 101 |
| AbD22643 | SGDNLGEKFVH | 68 | LVIYYDNHRPS | 85 | ASWDIESV | 102 |

FIG. 1B

Anti-IgA Antibodies -- Heavy Chain Sequences

| Ab Ref. | H-CDR1 | SEQ ID | H-CDR2 | SEQ ID | H-CDR3 | SEQ ID |
|---|---|---|---|---|---|---|
| AbD20776 | GGTFSSYSIS | 103 | WMGGIIPIFGIASYAQKFQG | 123 | DSSIEYFDY | 143 |
| AbD20777 | GGTFRSYAIS | 104 | WMGGIIPRFGIANYAQKFQG | 124 | GHRYTDGFAY | 144 |
| AbD20778 | GGTFSSYAIS | 105 | WMGGIYPFVGTAHYAQKFQG | 125 | DRSIYSYFDY | 145 |
| AbD20779 | GGTFSSYSIS | 106 | WMGGIIPIFGSANYAQKFQG | 126 | HGVSEAFDY | 146 |
| AbD20780 | GGTFSSNTS | 107 | WMGGIIPIFGTANYAQKFQG | 127 | EVDSSYPEDY | 147 |
| AbD20781 | GGTFSSYAIS | 108 | WMGGIIPIFGIAKYAQKFQG | 128 | DIRISTHFDY | 148 |
| AbD20782 | GYTFSYYH | 109 | WMGWINPNNGNTRYAQKIQr | 129 | NSFYSEWFDY | 149 |
| AbD20783 | GGTFSSYAIN | 110 | WMGGIIPFGTANYAQKFQG | 130 | VLYSSYYGMGHYEYFDI | 150 |
| AbD20784 | GGTFSSYAIS | 111 | WMGGIIPIFGIAKYAQKFQG | 131 | DIRISTHFDY | 151 |
| AbD20785 | GGTFSSYAIG | 112 | WMGGIIPHFGTANYAQKFQG | 132 | HSYSTGLYMGSDYMDY | 152 |
| AbD20786 | GGTFSSYAIS | 113 | WMGGIHPAFGTATYAQKFQG | 133 | HAGYGASGYEYMDN | 153 |
| AbD20787 | GGTFSSYAIN | 114 | WMGGIIPIFGTANYAQKFQG | 134 | DVSSYYYGHYHAYWFDV | 154 |
| AbD20788 | GGTFSGYGIS | 115 | WMGGIYPIFGVANYAQKFQG | 135 | DSDYFDY | 155 |
| AbD20789 | GFTFSDYGLH | 116 | WVGRIKSKTNGGITDYAAPVKG | 136 | SKGRGLYQNIQDY | 156 |
| AbD20790 | GGTFSSYAVN | 117 | WMGGIAPIFGTANYAQKFQG | 137 | GHYISSYAFDV | 157 |
| AbD20791 | GGTFSSYAIS | 118 | WMGGIIPIFGTASYAQKFQG | 138 | DIRISTHFDY | 158 |
| AbD20797 | GGTFSTYAIS | 119 | WMGGIIPIFGTANYAQKFQG | 139 | DFYDGFDY | 159 |
| AbD20798 | GGTFRSYAVH | 120 | WMGGIIPNFGTAHYAQKFQG | 140 | DEYVGHYFDH | 160 |
| AbD20799 | GGTFSDNAIS | 121 | WMGGIIPHFGTANYAQKFQG | 141 | EPIVNSSPMAV | 161 |
| AbD20813 | GGTFSSYAIS | 122 | WMGGIIPIFGAATYAQKFQG | 142 | QEYSYYNFDP | 162 |

FIG. 2A

Anti-IgA Antibodies – Light Chain Sequences

| Ab Ref. | L-CDR1 | SEQ ID | L-CDR2 | SEQ ID | L-CDR3 | SEQ ID |
|---|---|---|---|---|---|---|
| AbD20776 | RASQSINTYLA | 163 | LLIYGASSLQS | 183 | QQAYTRSF | 203 |
| AbD20777 | RASQGISNHLN | 164 | LLIYGASSLQS | 184 | QQEYSSPI | 204 |
| AbD20778 | SGSSSNIGKNYVH | 165 | VLIYRDNQRPS | 185 | QAYDLLSRRW | 205 |
| AbD20779 | RASQSISNYLN | 166 | LLIYDASSLQS | 186 | QQYYHFPI | 206 |
| AbD20780 | RASQDMLNLN | 167 | LLIYATSSLQS | 187 | QQRSHWSN | 207 |
| AbD20781 | RASQSIRNYLA | 168 | LLIYDASSLQS | 188 | HQYYSTPL | 208 |
| AbD20782 | RASQSINSYLA | 169 | LLIYAASNLQS | 189 | QQYYSWPI | 209 |
| AbD20783 | RASQIVSSSYLV | 170 | LLIYGASSRAT | 190 | QQADQYPM | 210 |
| AbD20784 | RASQGILSFLT | 171 | LLIYDASSLQS | 191 | HQYYSTPL | 211 |
| AbD20785 | RASQDISRYLN | 172 | LLIYGASNLQS | 192 | QQAYSIPV | 212 |
| AbD20786 | RASQSIKYLA | 173 | LLIYGASKLQS | 193 | QQYYSYPA | 213 |
| AbD20787 | SGDNIRKKYVH | 174 | LVIYDDNERPS | 194 | QVATYLNR | 214 |
| AbD20788 | RASQDIRNYLN | 175 | LLIYQVSTQQS | 195 | QQAYSNPH | 215 |
| AbD20789 | SGDKIGDKYAD | 176 | LVIYRDSNRPS | 196 | ASYDWHMIHY | 216 |
| AbD20790 | SGDKLGSSYAI | 177 | LVIYEQSKRPS | 197 | QVWTRIQY | 217 |
| AbD20791 | RASQSIRNYLA | 178 | LLIYDASSLQS | 198 | HQYYSTPL | 218 |
| AbD20797 | RASQSIKTYLA | 179 | LLIYAVSSLQS | 199 | MQSYSSPY | 219 |
| AbD20798 | RASQSIFNYLN | 180 | LLIYAASRLQS | 200 | QQMYDKPF | 220 |
| AbD20799 | RASQSISSYLN | 181 | LLIHDASSLQS | 201 | QQSLQYY | 221 |
| AbD20813 | RASQSINNYLN | 182 | LLIYQASRLQS | 202 | QQGYSSPF | 222 |

FIG. 2B

Anti-IgM Antibodies – Heavy Chain Sequences

| Ab Ref. | H-CDR1 | SEQ ID | H-CDR2 | SEQ ID | H-CDR3 | SEQ ID |
|---|---|---|---|---|---|---|
| AbD20768 | GDSVSDSSAAWN | 223 | WLGRIYYRSKWYNDYAYSVKS | 231 | ESPADVSGINFDI | 239 |
| AbD20769 | GFTFSRYGMN | 224 | WVSGISGSGSYTYYADSVKG | 232 | RSRYPYVYVFDY | 240 |
| AbD20770 | GFTFGDYWIH | 225 | WVSSISGGGNTYYADSVKG | 233 | SLYWRYSSYFDP | 241 |
| AbD20771 | GFTFSRYAMS | 226 | WVSSISYKGSNTYYADSVKG | 234 | APYPGSVSRYGAFDY | 242 |
| AbD20772 | GGTTSGYAIS | 227 | WMGRIFPRSGFANYAQKFQG | 235 | DVSGVTGYRKARDY | 243 |
| AbD20773 | GYSFTTYTIS | 228 | WMGIIYPSDSDTIYSPSFQG | 236 | SSVVGFDV | 244 |
| AbD20774 | GFTFSSYGMH | 229 | WVGRIKSKMNGGTIDYAAPVKG | 237 | SLTSGFDY | 245 |
| AbD20775 | GFTFSSFALT | 230 | WVGFIKSKTHGGTTDYAAPVKG | 238 | NRGHFDY | 246 |

FIG. 3A

Anti-IgM Antibodies – Light Chain Sequences

| Ab Ref. | L-CDR1 | SEQ ID | L-CDR2 | SEQ ID | L-CDR3 | SEQ ID |
|---|---|---|---|---|---|---|
| AbD20768 | RASQSIYSHLA | 247 | LLIYAASNLQS | 255 | QQSDESI | 263 |
| AbD20769 | SGSSSNIGSYYVN | 248 | LLIYRNNQRPS | 256 | SAYTGLSSSP | 264 |
| AbD20770 | RASQTISNHLN | 249 | LLIYAASSLQS | 257 | QQSLHYPY | 265 |
| AbD20771 | TGSSSNIGAGYYVH | 250 | LLIYGNNQRPS | 258 | GARDFQLSSW | 266 |
| AbD20772 | RASQGIRTRLK | 251 | LLIYGASTLQS | 259 | QQQDQTPY | 267 |
| AbD20773 | RASQSISSYLN | 252 | LLIYAASRLQS | 260 | QQHLSWPE | 268 |
| AbD20774 | SGDNLRDKYVY | 253 | LVIYSNSNRPS | 261 | YAWARRHTGA | 269 |
| AbD20775 | SGSSSNIGAYYVY | 254 | LLIYGNNQRPS | 262 | YSWDHMLNGY | 270 |

FIG. 3B

FIG. 4A anti-IgM - AbD20771

HC (SEQ ID NO: 271):
EVQLLESGGGLVQPGGSLRLSCAASGFTFSRYAMSWVRQAPGKGLEWVSSISYKGSNTYYADSVKGR
FTISRDNSKNTLYLQMNSLRAEDTAVYYCARAPYPGSVSRYGAFDYWGQGTLVTVSSASTKGPSVFPL
APSSKSTSGGTAALGCLVKDYFPEPVTVSWNSGALTSGVHTFPAVLQSSGLYSLSSVVTVPSSSLGTQT
YICNVNHKPSNTKVDKKVEPKSEFDYKDDDDKGAPHHHHHH

LC (SEQ ID NO: 272):
DIVLTQPPSVSGAPGQRVTISCTGSSSNIGAGYYVHWYQQLPGTAPKLLIYGNNQRPSGVPDRFSGSKS
GTSASLAITGLQAEDEADYYCGARDFQLSSWVFGGGTKLTVLGQPKAAPSVTLFPPSSEELQANKATLV
CLISDFYPGAVTVAWKADSSPVKAGVETTTPSKQSNNKYAASSYLSLTPEQWKSHRSYSCQVTHEGST
VEKTVAPTEA

FIG. 4B anti-IgM - AbD20775

HC (SEQ ID NO: 273):
EVQLVESGGGLVKPGGSLRLSCAASGFTFSSFALTWVRQAPGKGLEWVGFIKSKTHGGTTDYAAPVKG
RFTISRDDSKNTLYLQMNSLRTEDTAVYYCARNRGHFDYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVETKSEFDYKDDDDKGAPHHHHHH

LC (SEQ ID NO: 274):
DIVLTQPPSVSGAPGQRVTISCSGSSSNIGAYYVYWYQQLPGTAPKLLIYGNNQRPSGVPDRFSGSKSG
TSASLAITGLQAEDEADYYCSWDHMLNGYVFGGGTKLTVLGQPKAAPSVTLFPPSSEELQANKATLVC
LISDFYPGAVTVAWKADSSPVKAGVETTTPSKQSNNKYAASSYLSLTPEQWKSHRSYSCQVTHEGSTV
EKTVAPTEA

FIG. 4C anti-IgM – AbD20774

HC (SEQ ID NO: 275):
EVQLVESGGGLVKPGGSLRLSCAASGFTFSSYGMHWVRQAPGKGLEWVGRIKSKMNGGTTDYAAPV
KGRFTISRDDSKNTLYLQMNSLKTEDTAVYYCARSLTSGFDYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICNV
NHKPSNTKVDKKVEPKSEFDYKDDDDKGAPHHHHHH

LC (SEQ ID NO: 276):
DIELTQPPSVSVSPGQTASITCSGDNLRDKYVYWYQQKPGQAPVLVIYSNSNRPSGIPERFSGSNSGNT
ATLTISGTQAEDEADYYCYAWARRHTGAVFGGGTKLTVLGQPKAAPSVTLFPPSSEELQANKATLVCLI
SDFYPGAVTVAWKADSSPVKAGVETTTPSKQSNNKYAASSYLSLTPEQWKSHRSYSCQVTHEGSTVE
KTVAPTEA

FIG. 4D anti-IgM – AbD20772

HC (SEQ ID NO: 277):
QVQLVQSGAEVKKPGSSVKVSCKASGGTFSGYAISWVRQAPGQGLEWMGRIFPRSGFANYAQKFQG
RVTITADESTSTAYMELSSLRSEDTAVYYCARDVSGVTGYRKARDYWGQGTLVTVSSASTKGPSVFPL
APSSKSTSGGTAALGCLVKDYFPEPVTVSWNSGALTSGVHTFPAVLQSSGLYSLSSVVTVPSSSLGTQT
YICNVNHKPSNTKVDKKVEPKSEFDYKDDDDKGAPHHHHHH

LC (SEQ ID NO: 278):
DIQMTQSPSSLSASVGDRVTITCRASQGIRTRLKWYQQKPGKAPKLLIYGASTLQSGVPSRFSGSGSGT
DFTLTISSLQPEDFATYYCQQDTPYTFGQGTKVEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTK
SFNRGEA

FIG. 4E anti-IgM – AbD20770

HC (SEQ ID NO: 279):
EVQLLESGGGLVQPGGSLRLSCAASGFTFGDYWIHWVRQAPGKGLEWVSSISGGGNTYYADSVKGRF
TISRDNSKNTLYLQMNSLRAEDTAVYYCARSLYWRYSSYFDPWGQGTLVTVSSASTKGPSVFPLAPSS
KSTSGGTAALGCLVKDYFPEPVTVSWNSGALTSGVHTFPAVLQSSGLYSLSSVVTVPSSSLGTQTYICN
VNHKPSNTKVDKKVEPKSEFDYKDDDDKGAPHHHHHH

LC (SEQ ID NO: 280):
DIQMTQSPSSLSASVGDRVTITCRASQTISNHLNWYQQKPGKAPKLLIYAASSLQSGVPSRFSGSGSGT
DFTLTISSLQPEDFATYYCQQSLHYPYTFGQGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKS
FNRGEA

FIG. 4F anti-IgM – AbD20768

HC (SEQ ID NO: 281):
QVQLQQSGPGLVKPSQTLSLTCAISGDSVSDSSAAWNWIRQSPSRGLEWLGRIYYRSKWYNDYAVSV
KSRITINPDTSKNQFSLQLNSVTPEDTAVYYCARESPADVSGINFDIWGQGTLVTVSSASTKGPSVFPLA
PSSKSTSGGTAALGCLVKDYFPEPVTVSWNSGALTSGVHTFPAVLQSSGLYSLSSVVTVPSSSLGTQTY
ICNVNHKPSNTKVDKKVEPKSEFDYKDDDDKGAPHHHHHH

LC (SEQ ID NO: 282):
DIQMTQSPSSLSASVGDRVTITCRASQSIYSHLAWYQQKPGKAPKLLIYAASNLQSGVPSRFSGSGSGT
DFTLTISSLQPEDFATYYCQQSDESITFGQGTKVEIKRTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSF
NRGEA

FIG. 4G anti-IgM – AbD20794

HC (SEQ ID NO: 283):
QVQLVQSGAEVKKPGASVKVSCKASGYTFTGYDVSWVRQAPGQGLEWMGIINPYNGKTKYAQKFQGR
VTMTRDTSISTAYMELSRLRSEDTAVYYCARKPVGARYFDWGQGTLVTVSSASTKGPSVFPLAPSSKS
TSGGTAALGCLVKDYFPEPVTVSWNSGALTSGVHTFPAVLQSSGLYSLSSVVTVPSSSLGTQTYICNVN
HKPSNTKVDKKVEPKSEFDYKDDDDKGAPHHHHHH

LC (SEQ ID NO: 284):
DIVLTQPPSVSGAPGQRVTISCTGSSSNIGAGYVVHWYQQLPGTAPKLLIYDNNKRPSGVPDRFSGSKS
GTSASLAITGLQAEDEADYYCASWDLGRKYSVFGGGTKLTVLGQPKAAPSVTLFPPSSEELQANKATLV
CLISDFYPGAVTVAWKADSSPVKAGVETTTPSKQSNNKYAASSYLSLTPEQWKSHRSYSCQVTHEGST
VEKTVAPTEA

FIG. 4H anti-IgM – AbD20795

HC (SEQ ID NO: 285):
QVQLVQSGAEVKKPGASVKVSCKASGYIFTSYDMHWVRQAPGQGLEWMGWINPYNGGTKYAQKFQ
GRVTMTRDTSISTAYMELSRLRSEDTAVYYCARASYGGYSHVYSFDNWGQGTLVTVSSASTKGPSVFPL
APSSKSTSGGTAALGCLVKDYFPEPVTVSWNSGALTSGVHTFPAVLQSSGLYSLSSVVTVPSSSLGTQT
YICNVNHKPSNTKVDKKVEPKSEFDYKDDDDKGAPHHHHHH

LC (SEQ ID NO: 286):
DIELTQPPSVSVSPGQTASITCSGDKLRRKIVHWYQQKPGQAPVLVIYSDTDRPSGIPERFSGSNSGNTA
TLTISGTQAEDEADYYCASRTLGPRIWVFGGGTKLTVLGQPKAAPSVTLFPPSSEELQANKATLVCLISDF
YPGAVTVAWKADSSPVKAGVETTTPSKQSNNKYAASSYLSLTPEQWKSHRSYSCQVTHEGSTVEKTV
APTEA

FIG. 4I anti-IgM - AbD20800

HC (SEQ ID NO: 287):
EVQLVQSGAEVKKPGESLKISCKGSGYSFTTYTISWVRQMPGKGLEWMGIIYPSDSDTIYSPSFQGQVTI
SADKSISTAYLQWSSLKASDTAMYYCARSSVVGFDVWGQGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSEFDYKDDDDKGAPHHHHHH

LC (SEQ ID NO: 288):
DIQMTQSPSSLSASVGDRVTITCRASQSISSYLNWYQQKPGKAPKLLIYAASRLQSGVPSRFSGSGSGT
DFTLTISSLQPEDFATYYCQQHLSWPETFGQGTKVEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTK
SFNRGEA

US 10,294,306 B2

AFFINITY LIGANDS AND METHODS RELATING THERETO

CROSS-REFERENCE TO RELATED APPLICATIONS

This application claims the benefit of priority of U.S. Provisional Application No. 62/167,387, filed May 28, 2015, the entire content of which is incorporated herein by reference.

FIELD OF THE INVENTION

The invention relates to affinity ligands, such as antibody affinity ligands, and methods for using, identifying, and making affinity ligands.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1010888-105410US$_{13}$_ST25.txt, created on May 26, 2016, and having a size of 103,871 bytes and is filed concurrently with the specification. The sequence listing contained in this ASCII formatted document is part of the specification and is herein incorporated by reference in its entirety.

BACKGROUND OF THE INVENTION

Affinity chromatography is a method of separating biochemical mixtures based on highly specific interactions between an affinity ligand and its target, such as that between antibody and antigen. An affinity ligand that selectively interacts with the desired target is immobilized onto a solid support in order to create an affinity matrix that can be used in a column format. Affinity chromatography can be used in a number of applications, including nucleic acid purification, protein purification from cell free extracts or cell culture supernatants, and purification from blood.

BRIEF SUMMARY OF THE INVENTION

The present disclosure provides methods of generating affinity ligands, uses of such affinity ligands, and specific affinity ligands.

In one aspect, provided are affinity ligands that bind specifically to a target molecule, wherein the specific binding strength of the affinity ligand to the target molecule is reduced under buffer conditions including (i) a pH of about 4.0 to about 5.5 or (ii) about 1-2 M MgCl$_2$.

In some instances, the buffer condition may have a pH of about 4.0 to about 5.0. In some instances, the buffer condition may have a pH of about 4.0. In some instances, the buffer condition may have a pH of about 5.0. In some instances, the buffer condition may include 2 M MgCl$_2$. In some instances, the buffer condition may include 2 M MgCl$_2$ and a relatively neutral pH.

In some instances, the target molecule may be an immunoglobulin. In some instances, the target molecule may be an immunoglobulin selected from the group consisting of an immunoglobulin M (IgM), an immunoglobulin A (IgA), or an immunoglobulin E (IgE).

In some instances, the affinity ligand may be an immunoglobulin. For example, in some instances the affinity ligand may be a recombinant Fab fragment or Fab fragment derivative. In some instances, the affinity ligand may be an anti-IgE antibody comprising heavy chain complementarity determining regions CDR1, CDR2, and CDR3 sequences selected from any of the sequences set forth in FIG. 1A. In some instances, the affinity ligand may be an anti-IgE antibody having a light chain complementarity determining regions CDR1, CDR2, and CDR3 sequences selected from any of the sequences set forth in FIG. 1B. In some instances, the affinity ligand may be an anti-IgA antibody comprising heavy chain complementarity determining regions CDR1, CDR2, and CDR3 sequences selected from any of the sequences set forth in FIG. 2A. In some instances, the affinity ligand may be an anti-IgA antibody comprising light chain complementarity determining regions CDR1, CDR2, and CDR3 sequences selected from any of the sequences set forth in FIG. 2B. In some instances, the affinity ligand may be an anti-IgM antibody comprising heavy chain complementarity determining regions CDR1, CDR2, and CDR3 sequences selected from any of the sequences set forth in FIG. 3A. In some instances, the affinity ligand may be an anti-IgM antibody comprising light chain complementarity determining regions CDR1, CDR2, and CDR3 sequences selected from any of the sequences set forth in FIG. 3B.

In some instances, the affinity ligand may be linked to a solid support. In some instances, the solid support may be a bead or a sample plate. In some instances, the bead may be an agarose bead, a polystyrene bead, a polymethacrylate bead, a polyacrylamide bead, a magnetic bead, or a paramagnetic bead.

In another aspect, provided are methods of isolating a target molecule, the method comprising the steps of: providing a solid support linked to an affinity ligand; contacting the solid support with a sample containing the target molecule; washing the solid support with a wash buffer to remove unbound components of the sample; and eluting bound target molecule from the solid support with an elution buffer comprising (i) a pH of about 4.0 to about 5.5 or (ii) about 1-2 M MgCl$_2$.

In some instances, the elution buffer may include a pH of about 4.0 to about 5.5 and a relatively low salt concentration. In some instances, the elution buffer may include about 1 M to 2 M MgCl$_2$ and a relatively neutral pH. In some instances, the elution buffer may include about 1 M to 2 M MgCl$_2$ and a pH of about 6.0 to 8.0. In some instances, the eluting may be a single-step elution with an elution buffer comprising (i) a pH of about 4.0 to about 5.5 or (ii) about 1-2 M MgCl$_2$. In some instances, the eluting may be a multiple-step elution with a plurality of elution buffers comprising (i) a pH of about 4.0 to about 5.5 or (ii) about 1-2 M MgCl$_2$, wherein the plurality of elution buffers are applied to the solid support sequentially, wherein elution buffers having higher salt concentrations are applied after elution buffers having lower salt concentrations and elution buffers having lower pH are applied after elution buffers having higher pH. In some instances, the eluting may be a gradient elution with an elution buffer having a gradient of linearly increasing salt concentration during the time of the eluting, wherein the maximum salt concentration is about 1-2 M MgCl$_2$. In some instances, the eluting may be a gradient elution with an elution buffer having a gradient of linearly decreasing pH during the time of the eluting, wherein the minimum pH is about 4.0. In some instances, the wash buffer may have a pH of 6.0-8.0. In some instances, the wash buffer may have a relatively low salt concentration.

In some instances, the affinity ligand may be an immunoglobulin. In some instances, the target molecule may be an immunoglobulin M (IgM), an immunoglobulin A (IgA), or an immunoglobulin E (IgE). In some instances, the affinity ligand may be an anti-IgE antibody comprising heavy chain complementarity determining regions CDR1, CDR2, and CDR3 sequences selected from any of the sequences set forth in FIG. 1A. In some instances, the affinity ligand may be an anti-IgE antibody comprising light chain complementarity determining regions CDR1, CDR2, and CDR3 sequences selected from any of the sequences set forth in FIG. 1B. In some instances, the affinity ligand may be an anti-IgA antibody comprising heavy chain complementarity determining regions CDR1, CDR2, and CDR3 sequences selected from any of the sequences set forth in FIG. 2A. In some instances, the affinity ligand may be an anti-IgA antibody comprising light chain complementarity determining regions CDR1, CDR2, and CDR3 sequences selected from any of the sequences set forth in FIG. 2B. In some instances, the affinity ligand may be an anti-IgM antibody comprising heavy chain complementarity determining regions CDR1, CDR2, and CDR3 sequences selected from any of the sequences set forth in FIG. 3A. In some instances, the affinity ligand may be an anti-IgM antibody comprising light chain complementarity determining regions CDR1, CDR2, and CDR3 sequences selected from any of the sequences set forth in FIG. 3B.

In another aspect, provided are methods of selecting an affinity ligand that specifically binds to a target molecule under neutral buffer conditions and has reduced binding strength to the target molecular under mild elution conditions, the method including the steps of: expressing a naive affinity ligand library to produce a plurality of affinity ligands; providing a solid support linked to a target; contacting the solid support with the plurality of affinity ligands; washing the solid support with a wash buffer to remove unbound affinity ligands, wherein the wash buffer comprises neutral buffer conditions; contacting the solid support with an elution buffer comprising (i) a pH of about 4.0 to about 5.5 or (ii) about 1-2 M $MgCl_2$; and identifying affinity ligands that substantially dissociate from the solid support in the elution buffer.

In some instances, the affinity ligand library may not be preselected for characteristics favoring reduced binding strength to the target molecule under mild elution conditions. In some instances, the plurality of affinity ligands may be encoded by a plurality of nucleic acid sequences. In some instances, the plurality of nucleic acid sequences includes a heterologous promoter operably linked thereto. In some instances, the plurality of affinity ligands may be expressed on a plurality of phage.

In some instances, the elution buffer may have a pH of about 4.0 to about 5.5 and a relatively low salt concentration. In some instances, the elution buffer may include about 1 M to 2 M $MgCl_2$ and may have a relatively neutral pH. In some instances, the elution buffer may include about 1 M to 2 M $MgCl_2$ and may have a pH of about 6.0 to 8.0. In some instances, the wash buffer may have a pH of 6.0-8.0. In some instances, the wash buffer may have a relatively low salt concentration.

In some instances, the target may be an immunoglobulin. In some instances, the target may be an immunoglobulin M (IgM), an immunoglobulin A (IgA), or an immunoglobulin E (IgE).

In some instances, the plurality of affinity ligands may be a plurality of antibodies or derivatives thereof. In some instances, the plurality of affinity ligands is a plurality of Fab fragments or derivatives thereof. In some instances, the affinity ligand identified may be encoded by a polynucleotide comprising a nucleic acid sequence encoding heavy chain complementarity determining regions CDR1, CDR2, and CDR3 sequences selected from any of the sequences set forth in FIG. 1A. In some instances, the affinity ligand identified may be encoded by a polynucleotide comprising a nucleic acid sequence encoding light chain complementarity determining regions CDR1, CDR2, and CDR3 sequences selected from any of the sequences set forth in FIG. 1B. In some instances, the affinity ligand identified may be encoded by a polynucleotide comprising a nucleic acid sequence encoding heavy chain complementarity determining regions CDR1, CDR2, and CDR3 sequences selected from any of the sequences set forth in FIG. 2A. In some instances, the affinity ligand identified may be encoded by a polynucleotide comprising a nucleic acid sequence encoding light chain complementarity determining regions CDR1, CDR2, and CDR3 sequences selected from any of the sequences set forth in FIG. 2B. In some instances, the affinity ligand identified may be encoded by a polynucleotide comprising a nucleic acid sequence encoding heavy chain complementarity determining regions CDR1, CDR2, and CDR3 sequences selected from any of the sequences set forth in FIG. 3A. In some instances, the affinity ligand identified may be encoded by a polynucleotide comprising a nucleic acid sequence encoding light chain complementarity determining regions CDR1, CDR2, and CDR3 sequences selected from any of the sequences set forth in FIG. 3B.

In another aspect, provided are kits including the affinity ligand described above.

It will be appreciated from a review of the remainder of this application that further methods and compositions are also part of the invention.

BRIEF DESCRIPTION OF THE DRAWINGS

FIG. 1A and FIG. 1B show heavy and light chain CDR sequences, respectively, for anti-IgE antibodies according to some examples.

FIG. 2A and FIG. 2B show heavy and light chain CDR sequences, respectively, for anti-IgA antibodies according to some examples.

FIG. 3A and FIG. 3B show heavy and light chain CDR sequences, respectively, for anti-IgM antibodies according to some examples.

FIGS. 4A-4I show heavy and light chain sequences for anti-IgM antibodies according to some examples.

DEFINITIONS

Figure 5:
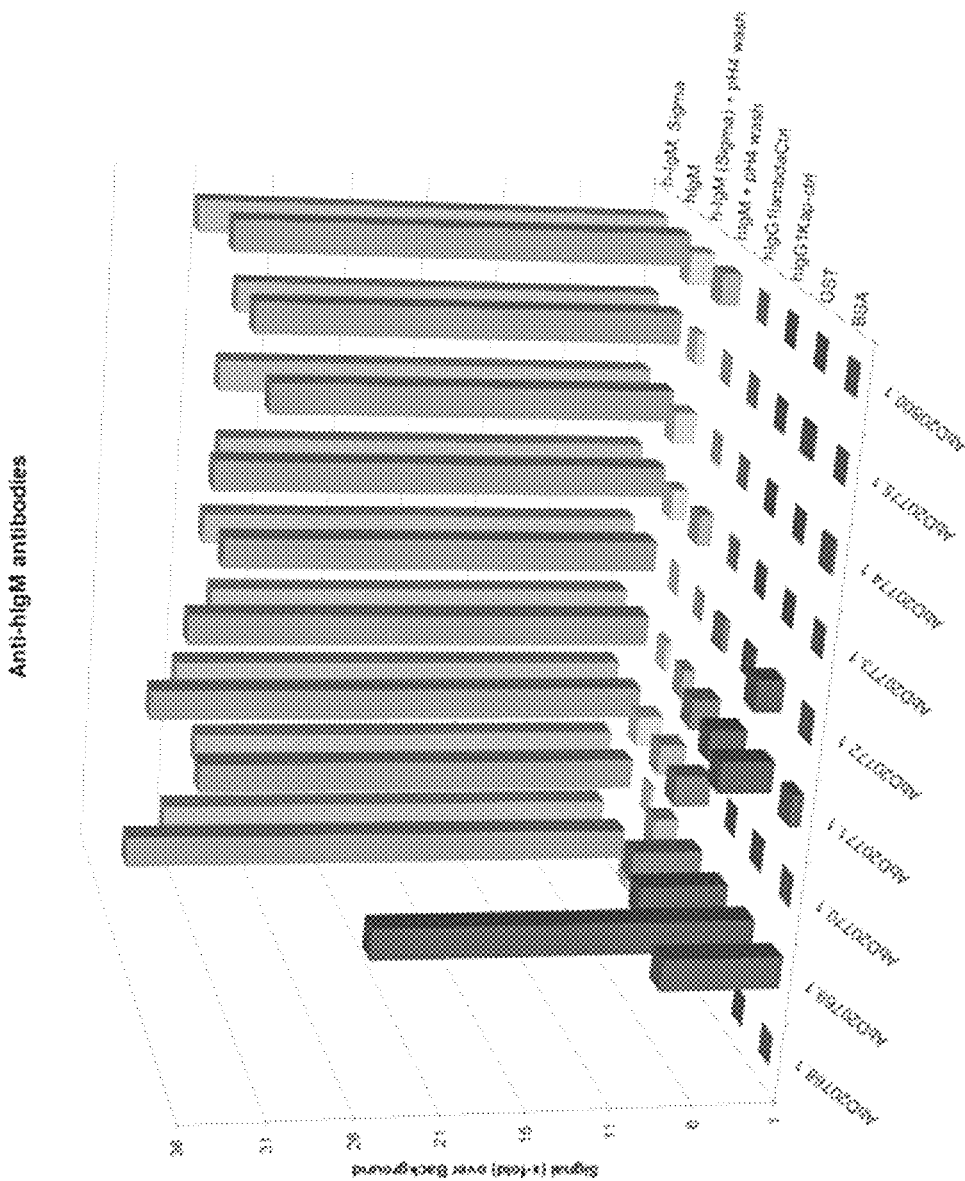
FIG. 5 shows ELISA results for a first set of anti-IgM antibody affinity ligands assessing binding to and elution of target molecules according to one example.

"Affinity ligand" or "ligand" refers to a composition (such as, for example, an antibody or non-antibody protein), that binds specifically to a specific substance, such as a protein, protein complex, or organic compound having a defined structure.

The term "solid support" is used herein to denote a solid inert surface or body to which an agent, such as an antibody or an antigen, that is reactive in any of the binding reactions described herein can be immobilized. The term "immobilized" as used herein denotes a molecularly-based coupling that is not dislodged or de-coupled under any of the conditions imposed during any of the steps of the assays described herein. Such immobilization can be achieved through a covalent bond, an ionic bond, an affinity-type bond, or any other covalent or non-covalent bond.

The term "antibody" or "immunoglobulin" refers to an immunoglobulin, composite, or fragmentary form thereof. The term may include but is not limited to polyclonal or monoclonal antibodies of the classes IgA, IgD, IgE, IgG, and IgM, derived from human or other cell lines, including natural or genetically modified forms such as humanized, human, single-chain, chimeric, synthetic, recombinant, hybrid, mutated, grafted, and in vitro generated antibodies and fragments thereof. "Antibody" may also include composite forms including but not limited to fusion proteins containing an immunoglobulin moiety. "Antibody" may also include non-quaternary antibody structures (such as camelids and camelid derivatives). "Antibody" may also include antibody fragments such as Fab (fragment-antigen binding), F(ab')2, Fv, scFv, Fd, dAb, Fc and other compositions that retain antigen-binding function. In addition, the term "antibody" includes aggregates, polymers, and conjugates of immunoglobulins or their fragments, where the molecules largely retain binding affinity for their epitope(s). Further, an "antibody" may be modified, such as, for example, by linking to a chemical or peptide moiety or detectable tag moiety.

The term "complementarity determining region" or "CDR" (also known as "hypervariable region" or "HVR") refers to an immunoglobulin hypervariable domain that determines specific binding of an immunoglobulin to an epitope. The variable regions of both the heavy and light chains of an antibody each generally contain three CDRs. Antibodies with different specificities have different CDRs, while antibodies of the exact same specificity may have identical CDRs.

A "constant region" refers to a region in the heavy and light chains of an antibody having relatively less variability compared to the N' terminal variable region of the heavy and light chains of an antibody. On the heavy chains, the constant region is generally the same in all antibodies of the same isotype and differs in antibodies of different isotypes. There are two primary types of light chains (kappa and lambda), each with a distinct constant region.

"Neutral buffer" or "neutral buffer condition" refers to a buffer having approximately physiological pH. Such buffers/conditions allow binding of proteins to an affinity column without resulting in substantial protein denaturation or aggregation. A neutral buffer or neutral buffer condition may permit near optimal interaction between an affinity ligand and a target molecule. A neutral buffer condition or neutral buffer generally has a pH in the range of about 6.0 to 8.0.

"Mild elution condition" or "mild elution buffer" refers to a buffer in which an affinity ligand that specifically binds to a target molecule dissociates from the target molecule (such as on an affinity matrix) without resulting in substantial protein denaturation or aggregation of the target molecule. This is in contrast to the harsh conditions that are typically applied in elution of a target molecule, such as low pH (about pH 2 to 3.5, for example). Such mild elution buffers may include relatively high pH (pH ≥4.0) or relatively high salt or ionic strength.

"Physiological pH" refers to the pH of human blood, which is about 7.4. A pH in the range of pH 7.0 to pH 7.8 may be considered approximately physiological pH.

"Naive expression library," for the purposes of expressing affinity ligands, refers to an expression library that expresses a large number of recombinant proteins, polypeptides, or peptides that have a large diversity of structure or specificity in their binding domains. A naive library is one generated from synthetic or natural ligand repertoires that have not previously subjected to selections for increased affinity for a target. A naive expression library is generated from a plurality of nucleic acid sequences that encode a plurality of affinity ligands or at least a plurality of target binding regions.

"Relatively neutral pH" refers to a pH of about pH 6.0 to 8.0.

A "solid support" refers to a material or group of materials having a rigid or semi-rigid surface or surfaces. In some embodiments, the solid support takes the form of thin films or membranes, beads, bottles, dishes, fibers, woven fibers, shaped polymers, particles, and microparticles, including but not limited to, microspheres. A solid support can be formed, for example, from an inert solid support of natural material, such as glass and collagen, or synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. In some cases, some functional groups naturally present on the surface of a carrier (for example, carboxylic acid (—COOH), free amine (—NH2), and sulfhydryl (—SH) groups) can be used for peptide linkage. In case no such functional group is naturally available, a desired functional group, such as a carboxylic acid group, or a moiety known to be a partner of a binding interaction (such as avidin that is capable of binding biotin) may be attached to such solid support. In some embodiments, the solid support is a carboxylated latex or magnetic microsphere.

The phrase "specific binding" or "binds specifically" refers to a binding reaction where two members of a binding pair (for example, an antibody and a molecule comprising the antibody's target epitope) bind to each other with an affinity that is at least 10-fold better than the members' affinity for other components of a heterogeneous mixture (for example, a hybridoma culture supernatant or other mixture of proteins).

The term "variable region" refers to an N' terminal region of each of the heavy and light chains of an antibody that has relatively more variability compared to the constant region(s) of the heavy and light chains of an antibody. The variable region contains the CDRs.

DETAILED DESCRIPTION OF THE INVENTION

It has been discovered that affinity ligands (such as antibodies) can be identified for use in immunoaffinity purification of target molecules (such as immunoglobulins M, A, or E) such that mild conditions can be used to elute the target molecule to which the affinity ligand specifically binds, thereby avoiding harsh elution conditions used previously. Certain examples and features of the present disclosure relate to methods to identify affinity ligands, such as antibodies, that are especially useful for mild elution immunoaffinity chromatography. Such ligands, when attached to a solid support, allow one-step purification of target molecules using mild elution conditions. The use of mild elution conditions circumvents the typically harsh elution conditions used in this type of chromatography that may lead to denaturing or aggregation of target molecules (such as low pH, for example, pH 3.0). The described methods utilize in vitro enrichment methods to permit selection of affinity ligands for which mild elution conditions can be used. The selection of such ligands is performed by a first binding step under conditions that allow binding in standard/neutral buffer conditions (such as neutral pH and/or low salt), followed by a subsequent elution step that is performed using mild elution conditions. The described methods permit specific selection and enrichment and finally isolation of affinity ligands having the desired characteristics. As such, affinity ligands of interest can be generated more rapidly and efficiently using the described methods.

Certain examples and features of the present disclosure relate to affinity ligands, such as antibodies, that exhibit the property of specifically binding to a target under neutral conditions and releasing the target under mild elution conditions. These affinity ligands can be selected for using the method described above. Examples of affinity ligands that are specific for human immunoglobulin M (IgM), human immunoglobulin A (IgA), and human immunoglobulin E (IgE) are described.

Certain examples and features of the present disclosure relate to methods of using such affinity ligands to purify targets using mild elution conditions. Affinity ligands may be used linked to a solid support as an affinity purification column. For example, some targets that are sensitive to harsh elution conditions (for example, pH 3.0) may be successfully purified using an affinity column generated using the affinity ligands that allow elution of targets under mild elution conditions. For example, such affinity ligands are useful for isolating IgM, IgA, or IgE molecules as these molecules may be sensitive to denaturation when affinity purified using harsh elution conditions. Other molecules that are sensitive to denaturation can be purified accordingly, once an affinity ligand has been isolated using the methods described in this disclosure.

I. Affinity Ligands

Affinity ligand compositions are described herein that bind specifically to a target and from which target can be eluted using mild elution conditions. As described further below, the affinity ligand may be an antibody, antibody-like molecule, or other affinity-binding molecule. For ease of description, this disclosure will sometimes describe examples and features of the affinity ligands in the context of antibody affinity ligands. However, this disclosure is not limited to affinity ligands that are antibodies.

The affinity ligand may be selected from a variety of different types of protein or non-protein compositions. In certain cases, an affinity ligand is an antibody, antibody-like molecule, or any other affinity-binding molecule derived from a naive expression library as described below in Section II. For example, the antibody may be a monoclonal antibody, a Fab fragment, a F(ab')2, an Fv, a scFv, an Fd, a dAb, an Fc fragment, a VHH, or other fragments thereof that retain antigen-binding function. In some examples, affinity ligand may be recombinant antibodies having heterologous constant and variable domains; for example, generated by a recombinant protein expression library. In some instances, the affinity ligand may be a recombinant Fab fragment. For example, the Fab fragment may have the variable domain and the first constant domain (Fd chain) of one heavy chain plus one complete light chain (L chain). The Fd and L chain are linked by strong non-covalent interactions and can be covalently linked by a disulfide bond. The polynucleotide sequence encoding the recombinant Fab fragment may be subcloned into an expression vector containing a heterologous promoter to drive expression of the recombinant Fab fragment. The Fab fragment may monovalent, bivalent, or multivalent. In some instances, the Fab fragment is monovalent. In some examples, the affinity ligand is a single-chain variable (scFv) fragment or a bivalent scFv fragment (diabody). ScFv fragments typically have one VH and one VL chain expressed as a single polypeptide joined by a peptide linker. The polypeptide linker stabilizes the interaction between the VH and VL chains. The polynucleotide sequence encoding the recombinant scFv fragment may be subcloned into an expression vector containing a heterologous promoter to drive expression of the recombinant scFv fragment. In some instances, the affinity ligand may be a recombinant antibody or protein that specifically binds to targets in a manner similar to antibodies, or fragment thereof that retains antigen-binding function. The affinity ligand may be a recombinant protein that contains at least three complementarity determining regions (CDRs) that cause the specific binding of the affinity ligand to the target; for example, three heavy chain CDRs and, in some examples, contains six CDRs (three heavy chain and three light chain). In some instances, the antibody may be a variable domain of heavy chain (VHH) antibody or a nanobody (a monomeric variable domain antibody). The VHH or nanobody may be encoded by a singly polypeptide.

In some examples, the affinity ligand is a camelid antibody or camelid nanobody. Camelid antibodies are certain IgG antibodies from the mammalian family of camel and dromedary (*Camelus bactrianus* and *Camelus dromaderius*) family, including new world members such as llama species (such as *Lama paccos*, *Lama glama* and *Lama vicugna*), that lack light chains. See, for example, International Appl. WO 94/04678. The small single variable domain (VHH) of the camelid antibody can be used to as the basis of a low molecular weight antibody-derived protein known as a "camelid nanobody" having high affinity for a target. See U.S. Pat. No. 5,759,808; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available.

In some cases, the affinity ligand can be a compound or non-antibody protein that specifically binds to targets in a manner similar to antibodies. Certain of these "antibody mimics" use non-immunoglobulin protein scaffolds as alternative protein frameworks for the variable regions of antibodies. For example, the affinity ligand can be a monobody, which are small antibody mimics using the scaffold of a fibronectin type III domain (FN3). FN3 scaffold functions as an effective framework onto which loops for specific building functions can be grafted. For example, the affinity ligand may utilize the tenth FN3 unit of human fibronectin as scaffold. It is small, monomeric, and does not have disulfide bonds. FN3-based antigen-binding molecules can be prepared using methods described in the art. For example, see Koide et al., J. Mol. Biol. 284: 1141-1151, 1998; Koide et al., Proc. Natl Acad. Sci. USA 99:1253-1258, 2002; and Batori et al., Protein Eng. 15:1015-20, 2002, and U.S. Pat. Nos. 6,818,418 and 7,115,396. In another example, the affinity ligand may be a single polypeptide chain binding molecule that contains the antigen binding sites of both the heavy and light variable regions of an antibody connected by a peptide linker and will fold into a structure similar to that of the two peptide antibody. See, for example, U.S. Pat. No. 5,260,203. Also, the affinity ligand may be a recombinant protein containing derivative sequences of one or more loops of cytochrome b562 that are selected for binding specificity to the target. See, for example, Ku et al., Proc. Natl. Acad. Sci. U.S.A. 92(14):6552-6556 (1995). In another example, the affinity ligand may be an antibody mimic based on a lipocalin scaffold, in which one or more of the hypervariable loops of the lipocalin protein are randomized and selected for specific binding to the target. See, for example, Beste et al., Proc. Natl. Acad. Sci. U.S.A. 96(5):1898-1903 (1999). An example of such antibody mimetics are Anticalins®, which are small, single chain peptides, typically between 160 and 180 residues. In addition, the affinity ligand may be a synthetic antibody mimic using the rigid, non-peptide organic scaffold of calixarene to which are attached multiple variable peptide loops used as binding sites. See, for example, U.S. Pat. No. 5,770,380. In some examples, the affinity ligand may be an antibody-like binding peptidomimetic. See, for example, Murali et al., Cell. Mol. Biol. 49(2):209-216 (2003). Also, in some examples, the affinity ligand may include a scaffold derived from one or more A-domains. For example, the affinity ligand may include multiple A-domains, each of which binding independently to a distinct epitope of the target. Such affinity ligands can be generated using methods described in, for example, Gliemann et al., Biol. Chem. 379:951-964, 1998; Koduri et al., Biochemistry 40:12801-12807, 2001 and Silverman et al., Nat Biotechnol. 23:1556-61, 2005. Other exemplary non-antibody scaffolds for use as ligands include darpins, affimers, cystine-knot mini-proteins, affilins, and peptides or non-protein-based scaffolds like aptamers.

In some instances, the affinity ligand may comprise an affinity tag or moiety. The affinity tag or moiety may be useful for purification of the affinity ligand or attachment to a solid support. For example, the affinity ligand may include at least one of a FLAG® peptide, 6×-Histidine (6×His) peptide, etc. In some cases, the affinity ligand is chemically modified to facilitate attachment of the ligand to a solid support.

In one aspect, the affinity ligand binds specifically to its target under neutral buffer conditions. Neutral buffer conditions may include a pH of approximately physiological pH, or relatively neutral pH, such as, for example a pH of about 6.0, 6.2, 6.5, 6.8, 7.1, 7.3, 7.5, 7.8, 7.9, 8.1, or a pH of about 6.0 to about 8.0. In some instances, the neutral buffer condition also comprises a relatively low salt concentration and/or ionic strength. For example, the salt concentration may be approximately physiological salt concentration. In some cases, the neutral buffer conditions include approximately physiological ionic strength. In some instances, neutral buffer conditions may be used for a wash buffer. In such instances, the wash buffer may have somewhat higher salt concentration or ionic strength to improve stringency and reduce non-specific binding of non-targets to the affinity ligand. In some instances, the neutral buffer condition does not include a salt. In certain instances, the neutral buffer condition may include detergent to reduce non-specific binding of non-targets to the affinity ligand. In some instances, the neutral buffer condition comprises a buffering agent. In one example, a neutral wash buffer may be phosphate buffered saline (PBS). In another example, the neutral wash buffer may be PBS containing about 0.05-1.0% Tween-20® (for example, 0.1%). Other solutions and detergents are contemplated.

In another aspect, under mild elution conditions, the specific binding of the affinity ligand to its target is reduced such that the affinity ligand and the target substantially dissociate from each other. In one aspect, the mild elution conditions may comprise a pH of about 4.0 to about 5.5. In another aspect, the mild elution conditions may comprise about 1-2 M $MgCl_2$.

In one aspect, mild elution conditions may comprise a pH in the range of about 4.0 to about 5.5. For example, mild elution conditions may include a pH of at least about 4.0 but less than or equal to about 5.5. The mild elution condition may include a pH greater than or equal to about 4.0, a pH of about 4.5, a pH of about 5.0, or a pH of about 5.5, or any pH within the range of about 4.0 to about 5.5. Where the pH is in the range of about 4.0 to 5.5, the elution buffer may further comprise a relatively low salt concentration. In some instances, the elution buffer may contain salt conditions relatively similar to physiological salt conditions. In some instances, the salt concentration may be 25 mM, 50 mM, 100 mM, 125 mM, 150 mM, 175 mM, 200 mM, 225 mM, or 250 mM. In one example, the elution buffer may include about 150 mM NaCl. In some cases, the mild elution conditions include approximately physiological ionic strength. In some instances the elution buffer may further include a buffering agent. Exemplary buffering agents include citrate, sodium acetate, and sodium phosphate buffered saline (PBS). In one example, the elution buffer may contain 100 mM citrate buffer. In another example, the elution buffer may contain 100 mM sodium acetate. In another example, the elution buffer may contain 1×PBS. In one example, the elution buffer may contain 150 mM NaCl and 100 mM citrate buffer.

In another aspect, mild elution conditions may comprise a salt concentration of about 1 M to 2 M $MgCl_2$. For example, the salt concentration may be about 0.8 M, about 1 M, about 1.2 M, about 1.4 M, about 1.6 M, about 1.8 M, about 2 M, or about 2.2 M. In one example, the mild elution condition comprises 2 M MgCl$_2$. In some instances, the mild elution conditions may further comprise a relatively neutral pH, or an approximately physiological pH, or a pH of about 6.8 to about 7.9, or a pH of about 6.0 to about 8.0, or any pH with these ranges. For example, the pH may be about 6.0, about 6.2, about 6.4, about 6.6, about 6.8, about 7.0, about 7.2, about 7.4, about 7.6, about 7.8, or about 8.0, when the mild elution condition includes a salt concentration of about 1 M to 2 M MgCl$_2$. In some instances, the elution buffer may further include a buffering agent. Exemplary buffering agents include citrate, sodium acetate, and phosphate buffered saline (PBS). The buffering agent may be of sufficient concentration to provide pH buffering. In one example, the elution buffer may contain 100 mM citrate. In another example, the elution buffer may contain 100 mM sodium acetate. In another example, the elution buffer may contain 1×PBS.

It is understood that, where the mild elution condition comprises a pH in the range of about 4.0 to 5.5, the neutral buffer conditions generally have a higher pH of approximately neutral pH or approximately physiological pH. It is also understood that, where the mild elution condition comprises about 1M to 2M MgCl$_2$, the neutral buffer conditions generally have a lower salt concentration or ionic strength.

In one aspect, the affinity ligand binds specifically to a target epitope of a target molecule. The target epitope can be a portion of a target molecule, such as a protein, nucleic acid, or other biological molecule. For example, the target may be a protein or other molecule that is sensitive to harsh buffer conditions, including low pH (such as pH 3.0). In some instances, a target may denature, dissociate into individual subunits, or dissociate from cofactors under harsh buffer conditions. In some examples, the target molecule may be an immunoglobulin (antibody), such as an immunoglobulin G (IgG), an immunoglobulin M (IgM), an immunoglobulin A (IgA), or an immunoglobulin E (IgE). In some instances, the affinity ligand may be a Fab fragment that binds specifically to an IgG, an IgM, an IgA, or an IgE.

For example, the affinity ligand may be a Fab fragment that binds specifically to an IgE having any of the heavy and light chain CDR sequences as set forth in FIG. 1A and FIG. 1B, respectively. In some instances, the antibodies specific for IgE may contain a combination of CDR1, CDR2, and CDR3 sequences as set forth in FIG. 1A or FIG. 1B. In some examples, such affinity ligand antibodies will have reduced binding to IgE under mild elution conditions, such as at a pH equal to or greater than about 4.0 and less than or equal to about 5.5, such that the IgE elutes from the affinity agent. For example, as described in Example 2, certain anti-IgE antibodies substantially dissociate from their target under elution conditions comprising pH 4.0 and pH 5.0. In some instances, the elution buffer conditions also comprise relatively low salt, such as 150 mM NaCl, and a buffering agent, such as citrate. Other suitable salts and buffering agents are also contemplated.

In another example, the affinity ligand may be a Fab fragment that binds specifically to an IgA having any of the heavy and light chain CDR sequences as set forth in FIG. 2A and FIG. 2B, respectively. In some instances, the antibodies specific for IgA may contain a combination of CDR1, CDR2, and CDR3 sequences as set forth in FIG. 2A or FIG. 2B. In some examples, such affinity ligand antibodies will have reduced binding to IgA under mild elution conditions, such as at a pH equal to or greater than about 4.0 and less than or equal to about 5.5, such that the IgE elutes from the affinity agent. For example, as described in Example 2, certain anti-IgA antibodies substantially dissociate from their target under elution conditions comprising pH 4.0 and pH 5.0. In some instances, the elution buffer conditions also comprise relatively low salt, such as 150 mM NaCl, and a buffering agent, such as citrate. Other suitable salts and buffering agents are also contemplated.

In another example, the affinity ligand may be a Fab fragment that binds specifically to an IgM having any of the heavy and light chain CDR sequences as set forth in FIG. 3A and FIG. 3B, respectively. In some examples, the affinity ligand may have at least one of the heavy chain sequences and at least one of the light chain sequences shown in FIGS. 4A-4I. In some instances, the affinity ligand may have at least one heavy and light chain sequences pair as shown in FIGS. 4A-4I. In some instances, the antibodies specific for IgM may contain a combination of CDR1, CDR2, and CDR3 sequences as set forth in FIG. 3A or FIG. 3B. In some examples, such affinity ligand antibodies will have reduced binding to IgM under mild elution conditions, such as at a pH equal to or greater than about 4.0 and less than or equal to about 5.5, such that the IgM elutes from the affinity agent. For example, as described in Example 2, certain anti-IgM antibodies substantially dissociate from their target under elution conditions comprising pH 4.0 and pH 5.0. In some instances, the elution buffer conditions also comprise relatively low salt, such as 150 mM NaCl, and a buffering agent, such as citrate. Other suitable salts and buffering agents are also contemplated.

In certain examples, the affinity ligand may have CDR sequences similar to those identified in this disclosure except varying in amino acid sequence at one or two amino acid positions. In some instances, the variance in sequence is a conservative amino acid change.

While this disclosure describes specific examples and features of the affinity ligands that are specific for immunoglobulin targets, affinity ligands specific for other types of ligands are also contemplated.

II. Selection Methods

The described selection methods allow for fast and efficient identification of affinity ligands, in particular antibodies, for use in affinity chromatography methods using mild elution conditions. In some embodiments, a plurality of potential affinity ligands are provided and processed such that ligands are selected that specifically bind to a target under neutral buffer conditions and display weak specific binding strength to the target under mild elution conditions.

A variety of methods are known and can be used for expressing a plurality of affinity ligands. In particular, naive expression libraries are useful for expressing a large number of recombinant proteins, polypeptides, and peptides, including, for example, antibodies, that have a large diversity of structure or specificity in their binding domains. A naive library is one generated from synthetic or natural ligand repertoires that have not previously subjected to selections for increased affinity for a target. In some instances, a naive library is generated from a plurality of nucleic acid sequences that encode a plurality of affinity ligands or at least a plurality of target binding regions. In some instances, the nucleic acid sequences encoding the target binding regions of the plurality of affinity ligands may have randomized sequences to generate binding regions in the plurality of affinity ligands that have randomized amino acid sequences. In some instances, the expression library expresses proteins or polypeptides having a structural domain with a common amino sequence and a binding domain having variable sequences such that the proteins or polypeptides expressed by the library may display a large number of distinct binding domains based on sequence variability. As such, different proteins or polypeptides expressed by the library may have different binding specificities for different targets under different conditions. In some examples, the expression libraries express hundreds of thousands, millions, or billions of different proteins or polypeptides, each of which may have a distinct binding affinity and, thus, may bind to different targets with different degrees of specificity under different conditions. Expression libraries useful for expressing a plurality of affinity ligands for use in this method include phage display libraries, yeast display libraries, ribosome display, mRNA display or other selection system, or any other recombinant expression library capable of expressing a plurality of affinity ligands having a range of binding specificities. An example of a useful affinity ligand expression library is the HuCAL Platinum® Platform (AbD Serotec, Bio-Rad), which provides phage display libraries of antibodies in Fab format representing an extensive array ($>10^{10}$ members) of CDR sequence variability (Prassler, J., et al. (2011). "HuCAL PLATINUM, a synthetic Fab library optimized for sequence diversity and superior performance in mammalian expression systems." J. Mol. Biol. 413(1): 261-278). In some instances, the variability of the plurality of affinity ligands expressed by the library facilitate the identification of ligands that bind to a target with specific binding affinity under neutral buffer conditions and have substantially reduced specific binding under mild elution conditions as described in Section I.

To perform the method, a target of interest is linked or adsorbed to a solid support. The target may be such as a protein, nucleic acid, or other biomolecule as described above. The solid support may be the wall or floor of an assay vessel, or a dipstick or other implement to be inserted into an assay vessel, or particles (such as magnetic beads) placed inside or suspended in an assay vessel. Particles, and especially beads, can be useful in many embodiments, including beads that are microscopic in size (microparticles) and formed of a polymeric material.

To prevent non-specific binding of affinity ligands, the target-linked solid support may be blocked with a blocking buffer. For example, the blocking buffer may contain an animal protein blocker (such a milk or bovine serum albumin), a non-animal protein blocker (such as Chemi-BLOCKER™), or a detergent (such a Tween-20®). In some instances, the blocking buffer may contain a closely related antigen. For example, where the target is an IgM antibody with kappa light chain, the blocking buffer may contain an antibody of different isotype (e.g., IgG) with kappa light chain as a blocker. Inclusion of this blocker may help to avoid enrichment of affinity ligands that bind specifically to the kappa light chain or to heavy chain epitopes that are similar in IgM and IgG. In particular, where the target protein is an immunoglobulin and the plurality of affinity ligands are antibodies, the target-linked solid support may be blocked with one or more types of antibody light chains as a blocker. For example, where the ligand is human IgM or human IgA, the target-linked solid support may be blocked with human IgG1 lambda or IgG1 kappa as described in Examples 1 and 2. In some instances, the blocking buffer may contain culture media (for example, media that sustain growth of a eukaryotic cell culture producing immunoglobulin like IgE, IgA or IgM). Blocking with culture medium may be useful to avoid enrichment of affinity ligands with cross-reactivity to components in the culture medium. In some instances, this can be useful because the target proteins are expressed in cells that are grown in culture medium. For example, as described in Examples 1 and 2, where the ligand is human IgE, the target-linked solid support may be blocked with culture medium.

The expressed affinity ligands can be brought into contact with the target-linked solid support under neutral buffer conditions to achieve binding of the affinity ligands, if any ligands in the library have affinity for the target. To remove non-specifically or weakly bound affinity ligands, a washing step may be performed using neutral buffer conditions as described above in Section I.

An elution step may then be performed using the mild elution conditions as described above in Section I. Under such mild elution conditions, the binding of some of the affinity ligands to its target may be sufficiently reduced such that the affinity ligand and the target substantially dissociate from each other under these conditions. In one aspect, the mild elution conditions may comprise a pH of about 4.0 to about 5.5. In another aspect, the mild elution conditions may comprise about 1-2 M $MgCl_2$.

The described methods allow for specific selection and enrichment of affinity ligands that specifically bind to a target under neutral buffer conditions and have substantially reduced specific binding to the target under mild elution conditions. Various elution conditions may be assessed to determine the optimal elution condition for a particular affinity ligand-target combination. Control elution conditions, in particular harsh elution conditions (such as pH 3.0), can be used for comparison purposes to assess the extent of elution obtained under the various elution conditions tested.

Additional assessment of affinity ligands identified using the methods may be performed. For example, once affinity ligands of interest are identified using the methods described above, the nucleotide sequences encoding the affinity ligands of interest may be cloned for larger scale production (for example, in vitro eukaryotic or bacterial expression). Cloned affinity ligands of interest may then be further screened to confirm specificity, such as, for example, by assessing binding affinity for other targets.

III. Affinity Chromatography Methods

Affinity ligands identified that specifically bind to a target under neutral buffer conditions and have substantially reduced binding to the target under mild elution conditions are useful for affinity chromatography. For example, such affinity ligands can be used for the affinity purification of targets in samples or expression cultures. The target may be a protein, nucleic acid, or other biological molecule. The affinity ligands are particularly useful for affinity chromatography for targets that are sensitive to harsh buffer conditions, including low pH (such as pH 3.0). For example, affinity chromatography using the affinity ligands described herein are useful for purification or assessment of targets that denature, dissociate into individual subunits, or dissociate from cofactors under harsh buffer conditions. Exemplary targets for the affinity chromatography methods described herein are immunoglobulins. As IgMs and IgAs are relatively sensitive to low pH conditions, affinity ligands that specifically bind to IgM or IgA are particularly useful for immune-chromatographic purification of IgMs and IgAs.

Affinity ligands for use in affinity chromatograph may be expressed and purified. These steps may be performed using conventional subcloning and expression technologies (for example, bacterial expression) using the nucleic acid sequences that encode these ligands or their binding domains. In some instances, the polynucleotides encoding the affinity ligands may be subcloned with an affinity tag or moiety that is useful for purification of the affinity ligands (for example, at least one of a FLAG® peptide, 6×-Histidine peptide, etc.). Affinity ligands are generally prepared in substantially purified form prior to use in generating an affinity chromatography matrix.

To perform affinity chromatography using the affinity ligands, the affinity ligands may be bound to a solid support to generate an affinity chromatography matrix. The affinity ligand is bound to or linked to the solid support. In some examples, the affinity ligand binds to the solid support through ionic interaction. In some instances, the affinity ligand is linked to the solid support through chemical bonds or cross-linking. Any solid support is contemplated for linkage to the affinity ligands. Various commercial matrices can be used to generate the affinity matrix with the affinity ligand bound thereto. Exemplary matrices include NETS-activated Sepharose matrix or Ni-NTA Agarose. The solid support may be selected based on characteristics of the purified affinity ligand, characteristics of the target, or intended uses of the target following affinity chromatography. The solid support can be, for example, porous or non-porous and can be in the form, for example, of a matrix, bead, particle, chip, or other conformation, for example, a membrane or a monolith (such as a single block, pellet, or slab of material). The solid support can be the wall or floor of an assay vessel, or a dipstick or other implement to be inserted into an assay vessel, or particles placed inside or suspended in an assay vessel. Particles, and especially beads, can be useful in many embodiments, including beads that are microscopic in size (microparticles) and formed of a polymeric material. Polymers useful as microparticles are those that are chemically inert relative to the components of the biological sample and to the assay reagents other than the affinity ligands that are immobilized on the microparticle surface. Examples of suitable polymers are polystyrenes, polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. The size range of the microparticles can vary. In some embodiments, the microparticles range in diameter from about 0.3 micrometers to about 120 micrometers, and other embodiments, from about 0.5 micrometers to about 40 micrometers, and in still other embodiments, from about 2 micrometers to about 10 micrometers.

Affinity chromatography may be performed on a wide range of samples that contain the target of interest. In some instances, the samples are obtained from subjects (including humans, primates, non-primate mammals, birds, reptiles, and amphibians). For example, the sample may be a bodily fluid. The sample may also be cultured bacteria or other cells or tissues that express the target of interest, a cell culture supernatant, or a lysate from bacterial or eukaryotic cells. In addition, one or more purification steps may be performed on the sample to enrich the target prior to affinity chromatography using the affinity ligands described herein.

The sample is applied to the solid support to allow the target to be bound by the affinity ligand. The conditions for the binding may be neutral or physiological. To remove non-specifically or weakly bound non-target compounds, a washing step may be performed using neutral buffer conditions as described above in Section I.

To elute the target bound to the affinity ligand-solid support, an elution step is performed using mild elution conditions as described above in Section I. Under mild elution conditions, the binding of the affinity ligand to its target is reduced such that the affinity ligand and the target substantially dissociate from each other under these conditions. In one aspect, the mild elution conditions may comprise a pH of about 4.0 to about 5.5. In another aspect, the mild elution conditions may comprise about 1-2 M $MgCl_2$. In some instances, elution may be performed as a single-step elution such that the target bound to the affinity ligand-solid support is eluted by exposing it to the mild elution conditions directly. In some instances, elution may be performed as a multiple-step elution such that the target bound to the affinity ligand-solid support is eluted by exposing it sequentially to multiple mild elution conditions having increasing salt concentrations or decreasing pH. In some instances, elution may be performed using a pH or salt gradient such that the target bound to the affinity ligand-solid support is eluted by exposing it to dynamic elution conditions as a gradient of linearly increasing salt concentration or decreasing pH.

The eluted target is useful for a variety of applications. For example, in the case that the target is an antibody (an immunoglobulin, such as IgM, IgA, or IgE), the eluted immunoglobulin target may be used, for example, as a therapeutic molecule, or as a diagnostic or laboratory reagent. In some instances, additional steps may be performed on the eluted target to prepare it for subsequent uses (for example, subsequent chromatography steps, filtration like ultrafiltration or diafiltration, dialysis, labeling, etc.).

IV. Kits

Kits containing affinity ligands that specifically bind to a target under neutral buffer conditions and elute the target under mild elution conditions are also contemplated. Kits may include one or more types of affinity ligands. The affinity ligands in the kit may be specific for the same target or for different targets. If the affinity ligands are specific for the same target, they may be specific for different epitopes of the target. In some instances, the affinity ligands are labeled (for example, with a peptide tag, or a chemical moiety for site-specific coupling to a matrix). The kits may include affinity ligands bound to a solid support. In some examples, the affinity ligand-bound solid support is packed into a chromatography column. Sometimes, the chromatography column is provided separately and the affinity ligand-bound solid support will be packed into the chromatography column prior to use. In some cases, the kit provides the affinity ligand and solid support separately along with instructions for coupling the affinity ligand to the solid support. The kit may further include an equilibration buffer, a washing buffer, an elution buffer, or some combination of these buffers. In some cases, more than one washing buffer or elution buffer is provided. Multiple elution buffers may be provided, with each elution buffer having a different elution condition (such as pH, salt type, or salt concentration). For example, different elution buffers may be provided for different affinity ligands included in the kit.

Exemplary buffers as referenced in this disclosure may include, for example, citrate, MES, or Bis-Tris, amongst others.

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. Certain features that are described in this specification in the context of separate embodiments can also be implemented in combination in a single implementation. Conversely, various features that are described in the context of a single implementation can also be implemented in multiple ways separately or in any suitable subcombination. Moreover, although features may be described above as acting in certain combinations, one or more features from a combination can in some cases be excised from the combination, and the combination may be directed to a subcombination or variation of a subcombination. Thus, particular embodiments have been described. Other embodiments are within the scope of the disclosure.

EXAMPLES

The following examples are offered to illustrate, but not to limit the claimed invention.

In the examples described below, antibodies were generated using the HuCAL PLATINUM® library that includes the CysDisplay® selection technology (Rothe, C., et al., 2008. "The human combinatorial antibody library HuCAL GOLD combines diversification of all six CDRs according to the natural immune system with a novel display method for efficient selection of high-affinity antibodies." J Mol Biol 376(4): 1182-1200.). The aim was to generate Fab antibodies against human IgM, IgA, and IgE that bind at neutral pH but can be eluted from the antigen under mild conditions (e.g. pH 4 to pH 5). Selection on the antigens using elution under mild conditions resulted in 14 antibodies against IgM, 40 antibodies against IgA, and 17 antibodies against IgE. Assays were performed to identify the antibodies with desirable properties for use as affinity chromatography reagent.

Example 1

This example provides a description of the materials and methods used in performing the experiments described in Example 2.

The antigens and closely related antigens (CRAs) are listed in Table 1 below.

TABLE 1

Antigens and CRAs

| Antigen/CRA | Reference | Source |
|---|---|---|
| hIgM | Ag05450 | Human IgM, human plasma (AbD Serotec 5275-5504) |
| hIgA | Ag5451 | Human IgA, human colostrum (AbD Serotec 5111-5504) |
| hIgM | Ag04815 | Human IgM, human serum (Sigma I8260) |
| hIgA | Ag4813 | Human IgA, human colostrum (Sigma I2636) |
| hIgE | Ag05681 | Human IgE with lambda light chain, AbD00264 |
| hIgE | Ag05682 | Human IgE with kappa light chain, (AbD Serotec, HCA190) |
| hIgE | Ag05711 | Human IgE, myeloma (AbD Serotec PHP142) |
| hIgG1lambda | Ag05029 | Human IgG1 lambda, human myeloma plasma (Sigma I5029) |
| hIgG1lambda | Ag05419 | Human IgG1 lambda, human myeloma plasma (Sigma I5029) |
| hIgG1kappa | Ag05153 | Human IgG1 kappa, human myeloma plasma (Sigma I5154) |

Recombinant antibodies were isolated from the HuCAL PLATINUM® library of human antibody genes by three iterative rounds of panning with the antigens as described in Table 1, using standard protocols. (Knappik et al., J. Mol. Biol. 2000, 296:57-86; Prassler et al., J. Mol. Biol. 2011, 413:261-278; Krebs et al., J. Immunol. Methods 2001, 254:67-84; Jarutat et al., Biol. Chem. 2006, 387:995-1003.)

For pannings 274.17-274.22 (see Table 2), the antigens were passively adsorbed to microtiter plates (F96 Maxisorp™ Nunc-Immuno Plate #442404) for use in "solid phase panning" as described below.

For pannings 274.4-274.9 and 289.12-14, the antigens were coupled to Dynal M-450 Epoxy beads (Invitrogen 140-11). The antigen coupled beads were incubated overnight at room temperature, blocked by addition of Tris, pH7.4, and subsequently re-suspended in PBS.

The phage antibody library was incubated with blocking buffer containing the CRAs as set forth in Table 1 and Table 2. The blocked library was then incubated with the antigen coupled beads, and non-specific or blocked antibodies were washed off. Specific antibody phage were eluted as noted in Table 2, by incubation with pH 3 elution buffer as control selection (150 mM NaCl, 100 mM Citrate buffer pH 3), with pH 4 elution buffer (150 mM NaCl, 100 mM Citrate buffer pH 4), or pH 5 elution buffer (150 mM NaCl, 100 mM Citrate buffer or 150 mM NaCl, 100 mM Sodium Acetate buffer) for the pH elution conditions or with high salt elution buffer (2M $MgCl_2$ in PBS). The pH elution condition buffers were neutralized with 1M Tris before *E. coli* infection. Phagemid containing bacteria were grown overnight at 37° C. and new antibody displaying phage were produced for the next panning round.

After 3 rounds of panning, the enriched pool of Fab genes was isolated and inserted into the *E. coli* expression vector pMx11-FH that leads to functional periplasmic expression of monovalent Fab fragments. (Rauchenberger et al., J. Biol. Chem. 2003, 278:38194-38205.) Each Fab includes a FLAG tag and a 6×His tag in tandem at the C-terminus of the heavy chain.

*E. coli* TGIF (TG1 depleted for the F pilus; Rauchenberger et al. 2003) was then transformed with the ligated expression vectors. Following transformation, 368 individual colonies were randomly picked for each panning and grown in microtiter plates, which were then stored with 15% glycerol at −80° C. These master plates were replicated and the resulting daughter plates were used for expression of the antibodies. After induction of antibody expression with 1 mM Isopropyl-β-D-thiogalactopyranosid (IPTG) overnight at 22° C., the cultures were chemically lysed, and the crude extracts were tested in Enzyme-Linked Immunosorbent Assay (ELISA) with the immobilized antigens and closely related antigens for the presence of antibody fragments that bind specifically to the immobilized antigens. In addition binding to IgM or IgA from a different source (Sigma) was tested. These antigens were also used to determine which antibodies can be washed of the ELISA plate after incubation with the different elution buffers for 20 min. The sequences of the antibody VH and VL complementarity-determining regions (CDR) were determined from a selection of the clones that gave a strong signal on the antigens in the ELISA (at least 5-fold above the background signal, antigens from AbD Serotec and Sigma) and a weak or no signal on the CRAs and on the antigen after elution buffer treatment (below 5-fold above the background signal). Clones containing antibodies with unique sequence were chosen for antibody production.

TABLE 2

Panning, Blocking and Screening Antigens

| Pan-code | Panning Antigens | Elution Strategy | CRAs Used for Blocking | Primary ELISA Screening on Antigens |
|---|---|---|---|---|
| 274.4 | hIgM (Ag05450) | pH 3 Elution | Ag05029 & Ag05153 (hIgG1 lambda & kappa) to final conc. of 50 μg/mL 100 μl cell culture medium | Ag05450 (hIgM) Ag05029 (hIgG1lambda) Ag05153 (hIgG1kappa) Ag04815 (hIgM, Sigma) Ag04815 (elution buffer incubation) |
| 274.5 | hIgA (Ag05451) | Bead Panning pH 3 Elution | Ag05029 & Ag05153 (hIgG1 lambda & kappa) to final conc. of 50 μg/mL 100 μl cell culture medium | Ag05451 (hIgA) Ag05029 (hIgG1lambda) Ag05153 (hIgG1kappa) Ag04813 (hIgA, Sigma) Ag04813 (elution buffer incubation) |
| 274.6 | hIgM (Ag05450) | Bead Panning pH 4 Elution | Ag05029 & Ag05153 (hIgG1 lambda & kappa) to final conc. of 50 μg/mL 100 μl cell culture medium | Ag05450 (hIgM) Ag05029 (hIgG1lambda) Ag05153 (hIgG1kappa) Ag04815 (hIgM, Sigma) Ag04815 (elution buffer incubation) |
| 274.7 | hIgA (Ag05451) | Bead Panning pH 4 Elution | Ag05029 & Ag05153 (hIgG1 lambda & kappa) to final conc. of 50 μg/mL 100 μl cell culture medium | Ag05451 (hIgA) Ag05029 (hIgG1lambda) Ag05153 (hIgG1kappa) Ag04813 (hIgA, Sigma) Ag04813 (elution buffer incubation) |
| 274.8 | hIgM (Ag05450) | Bead Panning High Salt Elution (2M MgCl$_2$) | Ag05029 & Ag05153 (hIgG1 lambda & kappa) to final conc. of 50 μg/mL 100 μl cell culture medium | Ag05450 (hIgM) Ag05029 (hIgG1lambda) Ag05153 (hIgG1kappa) Ag04815 (hIgM, Sigma) Ag04815 (elution buffer incubation) |
| 274.9 | hIgA (Ag05451) | Bead Panning High Salt Elution (2M MgCl$_2$) | Ag05029 & Ag05153 (hIgG1 lambda & kappa) to final conc. of 50 μg/mL 100 μl cell culture medium | Ag05451 (hIgA) Ag05029 (hIgG1lambda) Ag05153 (hIgG1kappa) Ag04813 (hIgA, Sigma) Ag04813 (elution buffer incubation) |
| 274.17 | hIgM (Ag05450) | Bead Panning pH 3 Elution | Ag05029 & Ag05153 (hIgG1 lambda & kappa) to final conc. of 50 μg/mL 100 μl cell culture medium | Ag05450 (hIgM) Ag05029 (hIgG1lambda) Ag05153 (hIgG1kappa) Ag04815 (hIgM, Sigma) Ag04815 (elution buffer incubation) |
| 274.18 | hIgA (Ag05451) | Bead Panning pH 3 Elution | Ag05029 & Ag05153 (hIgG1 lambda & kappa) to final conc. of 50 μg/mL 100 μl cell culture medium | Ag05451 (hIgA) Ag05029 (hIgG1lambda) Ag05153 (hIgG1kappa) Ag04813 (hIgA, Sigma) Ag04813 (elution buffer incubation) |
| 274.19 | hIgM (Ag05450) | Bead Panning pH 4 Elution | Ag05029 & Ag05153 (hIgG1 lambda & kappa) to final conc. of 50 μg/mL 100 μl cell culture medium | Ag05450 (hIgM) Ag05029 (hIgG1lambda) Ag05153 (hIgG1kappa) Ag04815 (hIgM, Sigma) Ag04815 (elution buffer incubation) |
| 274.20 | hIgA (Ag05451) | Bead Panning pH 4 Elution | Ag05029 & Ag05153 (hIgG1 lambda & kappa) to final conc. of 50 μg/mL 100 μl cell culture medium | Ag05451 (hIgA) Ag05029 (hIgG1lambda) Ag05153 (hIgG1kappa) Ag04813 (hIgA, Sigma) Ag04813 (elution buffer incubation) |
| 274.21 | hIgM (Ag05450) | Bead Panning High Salt Elution (2M MgCl$_2$) | Ag05029 & Ag05153 (hIgG1 lambda & kappa) to final conc. of 50 μg/mL 100 μl cell culture medium | Ag05450 (hIgM) Ag05029 (hIgG1lambda) Ag05153 (hIgG1kappa) Ag04815 (hIgM, Sigma) Ag04815 (elution buffer incubation) |
| 274.22 | hIgA (Ag05451) | Bead Panning High Salt Elution (2M MgCl$_2$) | Ag05029 & Ag05153 (hIgG1 lambda & kappa) to final conc. of 50 μg/mL 100 μl cell culture medium | Ag05451 (hIgA) Ag05029 (hIgG1lambda) Ag05153 (hIgG1kappa) Ag04813 (hIgA, Sigma) Ag04813 (elution buffer incubation) |
| 289.12 | hIgE lambda (Ag05681) | Bead Panning pH 4 | Ag05419 & Ag05153 (hIgG1 lambda & kappa) to final conc. of 50 μg/mL | Ag05681 (hIgE/lambda) Ag05682 (hIgE/kappa) Ag05419 (hIgG1lambda) |

TABLE 2-continued

Panning, Blocking and Screening Antigens

| Pan-code | Panning Antigens | Elution Strategy | CRAs Used for Blocking | Primary ELISA Screening on Antigens |
|---|---|---|---|---|
| | hIgE/kappa (Ag05682) | Elution, 10 min Elution Step | 100 μl cell culture medium | Ag05153 (hIgG1kappa) Ag05681 (elution buffer incubation) |
| 289.13 | hIgE lambda (Ag05681) hIgE/kappa (Ag05682) | Bead Panning pH 4 Elution, 5 min Elution Step | Ag05419 & Ag05153 (hIgG1 lambda & kappa) to final conc. of 50 μg/mL 100 μl cell culture medium | Ag05681 (hIgE/lambda) Ag05682 (hIgE/kappa) Ag05419 (hIgG1lambda) Ag05153 (hIgG1kappa) Ag05681 (elution buffer incubation) |
| 289.14 | hIgE lambda (Ag05681) hIgE/kappa (Ag05682) | Bead Panning pH 5 Elution, 10 min Elution Step | Ag05419 & Ag05153 (hIgG1 lambda & kappa) to final conc. of 50 μg/mL 100 μl cell culture medium | Ag05681 (hIgE/lambda) Ag05682 (hIgE/kappa) Ag05419 (hIgG1lambda) Ag05153 (hIgG1kappa) Ag05681 (elution buffer incubation) |

The ELISA screening protocol is set forth in the Table 3 below.

TABLE 3

ELISA Screening Protocol

| Plates | 384 well Maxisorp microtiter plates (MTP), black, flat bottom, Polystyrene (Nunc 460518) |
|---|---|
| Coating | 20 μL/well of antigens at 5 μg/mL in PBS pH 7.4; overnight (o/n) incubation at 4° C. |
| Wash | 2x PBST (PBS with 0.05% Tween ® 20) |
| Blocking | 100 μL of 5% non-fat dried milk in PBST for 1-2 h at room temperature (RT) |
| Wash | 2x PBST |
| Primary Ab (HuCAL ®-Fab) | 20 μL/well of crude E. coli lysate of expression culture containing HuCAL ®-Fab (pre-blocked with a final concentration of 5% non-fat dried milk in PBST), 1 h at RT |
| Wash | 5x PBST |
| Secondary Ab | 20 μL/well of anti-His tag, HRP conjugate (Qiagen 34460), 1:2000 dilution in HiSpec buffer (AbD Serotec BUF049), 1 h at RT |
| Wash | 5x PBST |
| Detection | 20 μL/well QuantaBlu ® (Thermo Scientific 15169) |
| Reader Settings | Excitation at 320 ± 25 nm, emission at 420 ± 35 nm |

E. coli TGIF⁻ cultures (250 mL) containing the chosen antibody genes were grown at 30° C. until $OD_{600nm}$ reached 0.5, and the antibody expression was induced by adding IPTG to a final concentration of 1 mM. After further incubation for at least 14 hours at 30° C., the cells were harvested, chemically lysed, and the soluble crude extract was subjected to one-step affinity chromatography (Ni-NTA Agarose, Qiagen 1018240). After elution of the purified antibodies from the column, the buffer was changed from elution buffer to 3xPBS, pH 7.4, and the concentration was determined by $UV_{280nm}$ measurement. Purity and activity was tested subsequently by Coomassie-stained SDS-PAGE and ELISA, respectively.

The quality control ELISA (indirect ELISA) protocol using purified HuCAL® antibodies is set forth in Table 4 below.

TABLE 4

QC ELISA Protocol

| Plate | 384 well Maxisorp MTP, black, flat bottom, Polystyrene (Nunc 460518) |
|---|---|
| Coating | 20 μL/well of antigen at 5 μg/mL in PBS, o/n at 4° C. |
| Wash | 2x PBST (PBS with 0.05% Tween-20 ®) |
| Blocking | 100 μL of 5% non-fat dried milk in PBST for 1-2 hr at RT |
| Wash | 2x PBST |
| Primary Ab (HuCAL ®-Fab) | 20 μL/well of antibody at 2 μg/mL in PBST for 1 hr at RT |
| Wash | 5x PBST |
| Secondary Ab | 20 μL/well of anti-His tag, HRP conjugate (Qiagen 34460), 1:2000 dilution in HiSpec buffer (AbD Serotec BUF049), 1 hr at RT |
| Wash | 5x PBST Optional: manually wash specific wells with elution buffer, incubate for 5 min, remove buffer, repeat 2x |
| Detection | 20 μL/well QuantaBlu ® (Thermo Scientific 15169) |
| Reader Settings | Excitation at 320 ± 25 nm, emission at 420 ± 35 nm |
| Background | Signal values on unspecific antigens (BSA, GST) were used for the calculation of background signal |

Example 2

The results of the methods described in Example 1 are described in this example.

Primary ELISA Screening

The outcome of a panning is tested in the primary screening on several antigens and closely related antigens (CRA). The antigen role defines whether positive (+) signals are expected (positive controls for the panning antigen) or whether no signal (−) is wanted (negative controls; CRAs).

An ELISA signal on an antigen plate (positive control) is considered a hit if the signal is 5-fold above background. Background is the average value of a number of wells on the plate that were not treated with antigen or antibody.

A signal on a CRA (negative control) is counted, and during the analysis subtracted from the positive hits, if the signal is at least 2-fold above background.

A clone is considered a hit if it is positive on all antigens (positive controls) and negative on all CRAs (negative controls).

The values in Table 5 indicate the numbers of hits according to the above definition. The Analysis column indicates the number of hits that no longer bind to the antigen under the test elution conditions.

TABLE 5

Primary screening ELISA results

| Antigen Role | + | + | − | − | − | |
|---|---|---|---|---|---|---|
| Panning | hIgM, Ag05450 | hIgM, Ag04815 | hIgG1 lambda, Ag05029 | hIgG1 kappa, Ag05153 | hIgM, Ag04815 & elution buffer | Analysis |
| 274.4 | 234 | 43 | 0 | 2 | 11, pH 3 | 38 |
| 274.6 | 191 | 59 | 1 | 2 | 5, pH 4 | 55 |
| 274.8 | 234 | 163 | 3 | 2 | 7, high salt | 153 |
| 274.17 | 239 | 8 | 0 | 15 | 1, pH 3 | 4 |
| 274.19 | 228 | 106 | 2 | 0 | 1, pH 4 | 93 |
| 274.21 | 28 | 0 | 1 | 1 | 7, high salt | 0 |
| | hIgA, Ag05451 | hIgA, Ag04813 | hIgG1 lambda, Ag05029 | hIgG1 kappa, Ag05153 | hIgA, Ag04813 & elution buffer | Analysis |
| 274.5 | 205 | 200 | 2 | 1 | 71, pH 3 | 125 |
| 274.7 | 223 | 201 | 1 | 31 | 96, pH 4 | 94 |
| 274.9 | 285 | 286 | 1 | 8 | 271, high salt | 5 |
| 274.18 | 193 | 215 | 3 | 1 | 52, pH 3 | 132 |
| 274.20 | 173 | 184 | 0 | 6 | 119, pH 4 | 58 |
| 274.22 | 174 | 220 | 6 | 1 | 166, high salt | 16 |
| | hIgE, Ag05681 | hIgE, Ag05682 | hIgG1 lambda, Ag05419 | hIgG1 kappa, Ag05153 | hIgE, Ag05681 & elution buffer | Analysis |
| 289.12 | 9 | 1 | 0 | 3 | 4, pH 4 | 1 |
| 289.13 | 20 | 24 | 24 | 164 | 208, pH 4, not used* | 9 |
| 289.14 | 25 | 186 | 147 | 10 | 21, pH 5 | 10 |

*The number of hits was too high, so this result was considered to be an artifact and was not used to pick clones for further characterization.

Sequencing and Identification of Unique Antibodies

For the IgE project, 20 clones (289.12: 1, 289.13: 9, 289.14: 10) were sequenced and resulted in 17 different antibodies (AbD22512, AbD22628-22643). The heavy and light chain CDR1, CDR2, and CDR3 region sequences of these antibodies are shown in FIG. 1A and FIG. 1B.

For the IgA project, a total of 45 clones (274.7: 18, 274.9: 3, 274.20: 15, 274.22: 9) were selected for further analysis. Sequencing of the gene regions coding for VH and VL revealed 40 different antibodies (AbD20776-20791, AbD20797-20799, AbD20801-20812, AbD20813-20821). The heavy and light chain CDR1, CDR2, and CDR3 region sequences of these antibodies are shown in FIG. 2A and FIG. 2B.

For the IgM project, a total of 50 clones (274.6: 15, 274.8: 20, 274.19: 15) were selected for further analysis. Sequencing of the gene regions coding for VH and VL revealed 14 different antibodies (AbD20768-20775, AbD20792-20796, AbD20800). The heavy and light chain CDR1, CDR2, and CDR3 region sequences of these antibodies are shown in FIG. 3A FIG. 3B; full heavy and light chain sequences for certain of these antibodies is shown in FIGS. 4A-4I.

The antibodies were expressed, purified via affinity chromatography and tested using ELISA. The results are shown in FIGS. 5-9 and in Tables 6-8 and described further below.

For each clone shown, a number of antigens and conditions were tested. The bars indicate the signal strength plotted as specific fluorescence divided by background fluorescence. The designation of the clones is "clone-name.batch-number." For example, AbD20768.1 is the first batch of AbD20768

FIG. 5: BSA and N1-CD33-6×His are unrelated antigens. hIgG1Kap-ctrl and hIgG1lambdaCtrl are CRAs (human IgG1 isotype with kappa and lambda light chain, respectively). hIgM is human IgM from AbD Serotec (5275-5504). H-IgM (Sigma) is human IgM from Sigma (I8260). Antigen with "pH4 wash" indicate the residual signal on that antigen after 3 consecutive 5 minute incubations of the corresponding wells with the elution buffer (pH 4).

Figure 6:
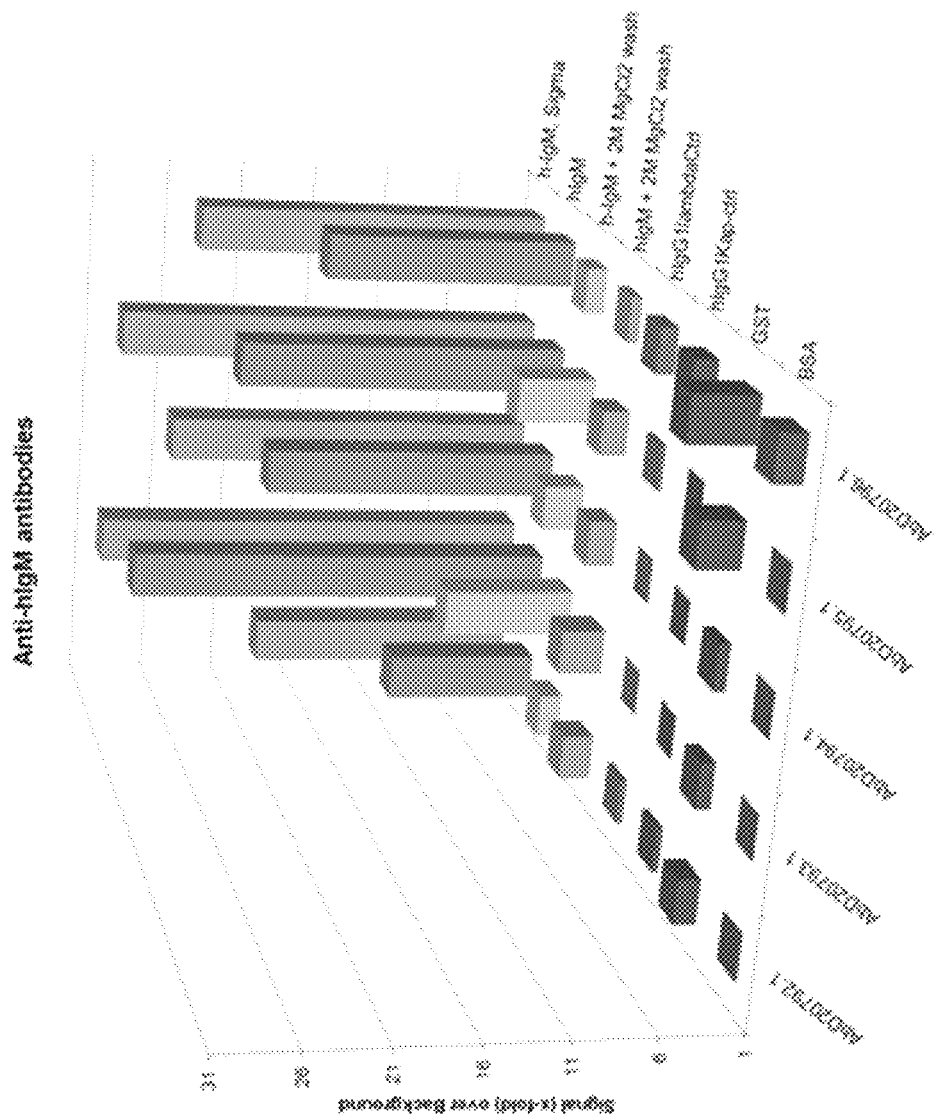
FIG. 6 shows ELISA results for a second set of anti-IgM antibody affinity ligands assessing binding to and elution of target molecules according to one example.

FIG. 6: BSA and N1-CD33-His6 are unrelated antigens. hIgG1Kap-ctrl and hIgG1lambdaCtrl are CRAs (human IgG1 isotype with kappa and lambda light chain, respectively). hIgM is human IgM from AbD Serotec (5275-5504). H-IgM (Sigma) is human IgM from Sigma (I8260). Antigen with "2M MgCl2 wash" indicate the residual signal on that antigen after 3 consecutive 5 minute incubations of the corresponding wells with the elution buffer (2M $MgCl_2$ in PBS).

Figure 7:
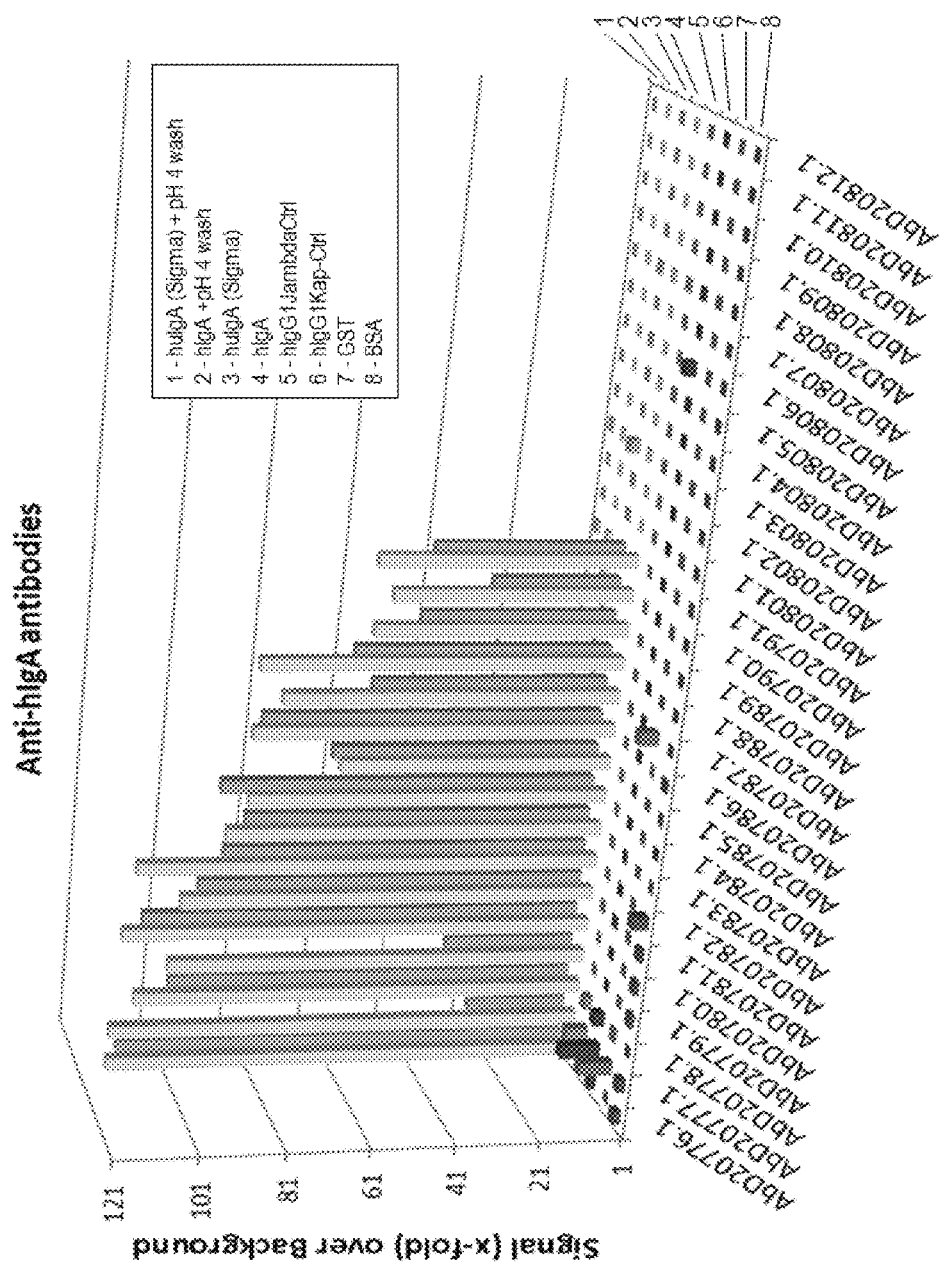
FIG. 7 shows ELISA results for a first set of anti-IgA antibody affinity ligands assessing binding to and elution of target molecules according to one example.

FIG. 7: BSA and GST are unrelated antigens. hIgG1Kap-ctrl and hIgG1lambdaCtrl are CRAs (human IgG1 isotype with kappa and lambda light chain, respectively). hIgA is human IgA from AbD Serotec (5111-5504). HIgA (Sigma) is human IgA from Sigma (I2636). Antigen with "pH4 wash" indicate the residual signal on that antigen after 3 consecutive 5 minute incubations of the corresponding wells with the elution buffer (pH 4). A number of antibodies that were originally positive in the primary screening turned out to be negative here (AbD20801 to AbD20812).

Figure 8:
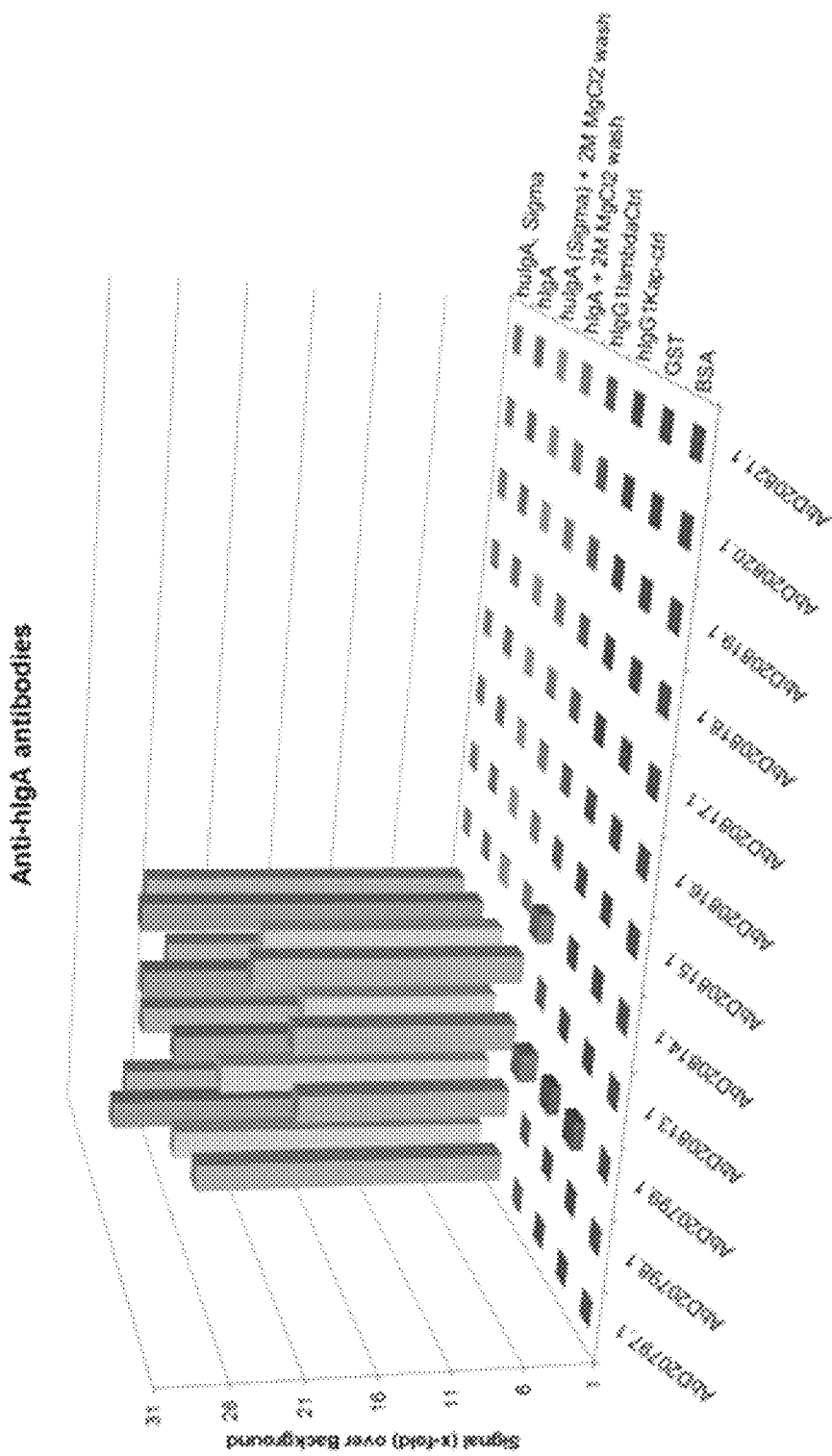
FIG. 8 shows ELISA results for a second set of anti-IgA antibody affinity ligands assessing binding to and elution of target molecules according to one example. Controls N1-CD33-6×His and BSA are also shown.

FIG. 8: BSA and N1-CD33-His6 are unrelated antigens. hIgG1Kap-ctrl and hIgG1lambdaCtrl are CRAs (human IgG1 isotype with kappa and lambda light chain, respectively). hIgA is human IgA from AbD Serotec (5111-5504). HIgA (Sigma) is human IgA from Sigma (I2636). Antigen with "2M MgCl2 wash" indicate the residual signal on that antigen after 3 consecutive 5 minute incubations of the corresponding wells with the elution buffer (2M $MgCl_2$ in PBS). A number of antibodies that were originally positive in the primary screening turned out to be negative here (AbD20814-AbD20821).

Figure 9:
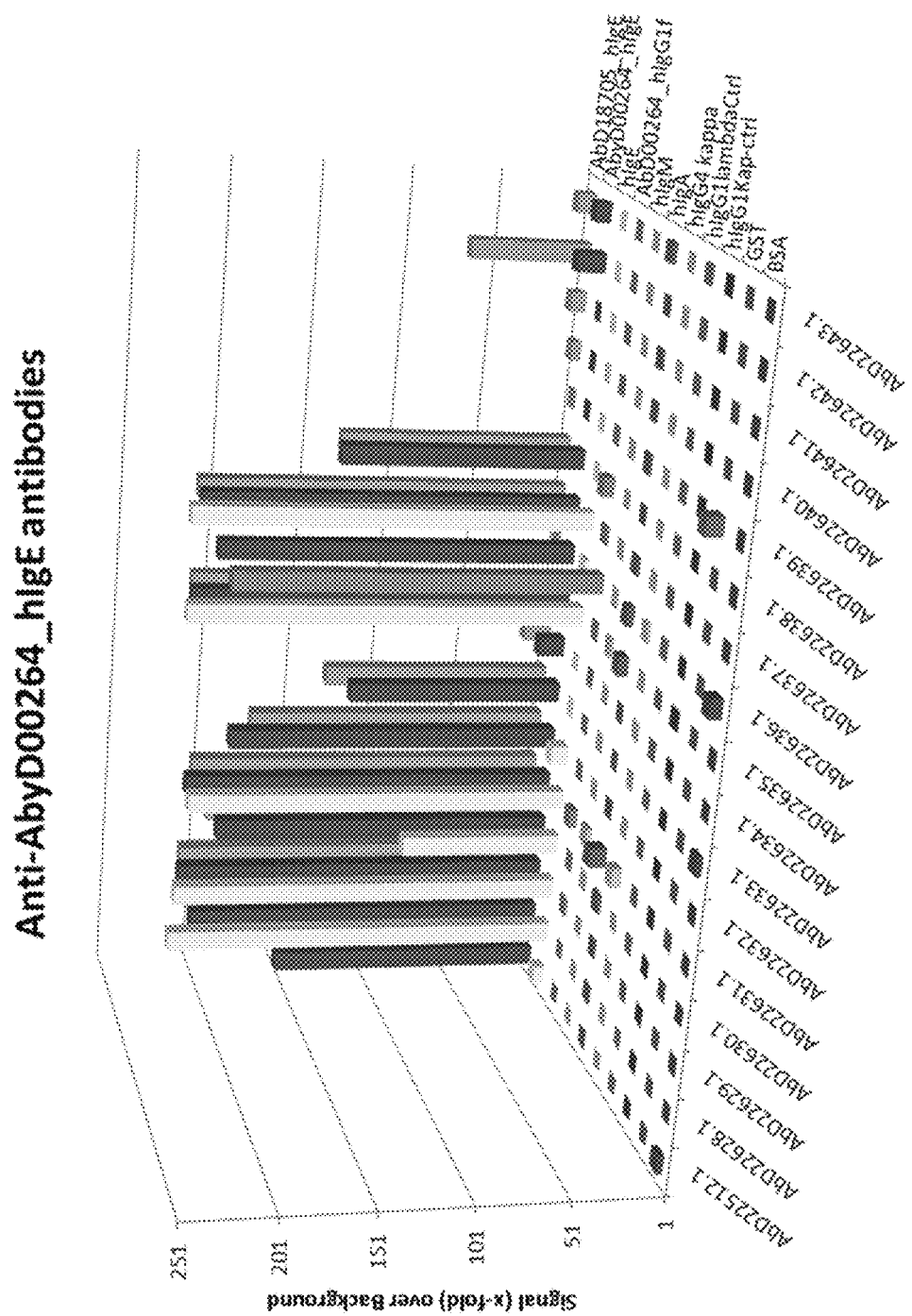
FIG. 9 shows ELISA results for a set of anti-IgE antibody affinity ligands assessing binding specificity for target molecules according to one example.

FIG. 9: BSA and GST are unrelated antigens. hIgG1Kapctrl and hIgG1lambdaCtrl are CRAs (human IgG1 isotype with kappa and lambda light chain, respectively). hIgG4 kappa is human IgG4 with kappa light chain (Sigma I4639). hIgM is human IgM from AbD Serotec (5275-5504). AbD00264_hIgG1f is a human antibody derived from HuCAL and formatted into the IgG1 isotype. AbD00264_hIgE is the same antibody formatted into the IgE isotype. AbD18705_hIgE is another HuCAL-derived antibody formatted into the IgE isotype. hIgE is human IgE from myeloma (AbD Serotec PHP 142).

TABLE 6

Overview of Specific Anti-hIgM Antibodies

| Antibody | Antigen Number | Antigen Name | conc. [mg/ml] | Elution buffer |
|---|---|---|---|---|
| AbD20768.1 | Ag05450 | hIgM | 1.56 | pH 4 |
| AbD20769.1 | Ag05450 | hIgM | 1.65 | pH 4 |
| AbD20770.1 | Ag05450 | hIgM | 1.6 | pH 4 |
| AbD20771.1 | Ag05450 | hIgM | 1.7 | pH 4 |
| AbD20772.1 | Ag05450 | hIgM | 0.88 | pH 4 |
| AbD20773.1 | Ag05450 | hIgM | 0.82 | pH 4 |
| AbD20774.1 | Ag05450 | hIgM | 1.48 | pH 4 |
| AbD20775.1 | Ag05450 | hIgM | 1.11 | pH 4 |
| AbD20800.1 | Ag05450 | hIgM | 0.72 | pH 4 |
| AbD20792.1 | Ag05450 | hIgM | 0.97 | 2M MgCl$_2$ |
| AbD20793.1 | Ag05450 | hIgM | 0.3 | 2M MgCl$_2$ |
| AbD20794.1 | Ag05450 | hIgM | 0.93 | 2M MgCl$_2$ |
| AbD20795.1 | Ag05450 | hIgM | 0.73 | 2M MgCl$_2$ |
| AbD20796.1 | Ag05450 | hIgM | 0.93 | 2M MgCl$_2$ |

TABLE 7

Overview of Specific Anti-hIgA Antibodies

| Antibody | Antigen Number | Antigen Name | conc. [mg/ml] | Elution buffer |
|---|---|---|---|---|
| AbD20776.1 | Ag05451 | hIgA | 1.13 | pH 4 |
| AbD20777.1 | Ag05451 | hIgA | 0.96 | pH 4 |
| AbD20778.1 | Ag05451 | hIgA | 1.32 | pH 4 |
| AbD20779.1 | Ag05451 | hIgA | 1.38 | pH 4 |
| AbD20780.1 | Ag05451 | hIgA | 1.54 | pH 4 |
| AbD20781.1 | Ag05451 | hIgA | 0.99 | pH 4 |
| AbD20782.1 | Ag05451 | hIgA | 0.99 | pH 4 |
| AbD20783.1 | Ag05451 | hIgA | 1.25 | pH 4 |
| AbD20784.1 | Ag05451 | hIgA | 1.03 | pH 4 |
| AbD20785.1 | Ag05451 | hIgA | 1.46 | pH 4 |
| AbD20786.1 | Ag05451 | hIgA | 1.22 | pH 4 |
| AbD20787.1 | Ag05451 | hIgA | 1.35 | pH 4 |
| AbD20788.1 | Ag05451 | hIgA | 1.5 | pH 4 |
| AbD20789.1 | Ag05451 | hIgA | 1.68 | pH 4 |
| AbD20790.1 | Ag05451 | hIgA | 1.61 | pH 4 |
| AbD20791.1 | Ag05451 | hIgA | 1.25 | pH 4 |
| AbD20797.1 | Ag05451 | hIgA | 1.43 | 2M MgCl$_2$ |
| AbD20798.1 | Ag05451 | hIgA | 1.43 | 2M MgCl$_2$ |
| AbD20799.1 | Ag05451 | hIgA | 1.04 | 2M MgCl$_2$ |
| AbD20813.1 | Ag05451 | hIgA | 1.21 | 2M MgCl$_2$ |

TABLE 8

Overview of Specific Anti-hIgE Antibodies

| Antibody | Antigen Number | Antigen Name | conc. [mg/ml] | Elution buffer |
|---|---|---|---|---|
| AbD22512.1 | Ag05681 | hIgE | 1.76 | pH 4 |
| AbD22628.1 | Ag05681 | hIgE | 1.41 | pH 4 |

TABLE 8-continued

Overview of Specific Anti-hIgE Antibodies

| Antibody | Antigen Number | Antigen Name | conc. [mg/ml] | Elution buffer |
|---|---|---|---|---|
| AbD22629.1 | Ag05681 | hIgE | 1.83 | pH 4 |
| AbD22630.1 | Ag05681 | hIgE | 1.78 | pH 4 |
| AbD22631.1 | Ag05681 | hIgE | 1.75 | pH 4 |
| AbD22632.1 | Ag05681 | hIgE | 1.77 | pH 4 |
| AbD22633.1 | Ag05681 | hIgE | 1.59 | pH 4 |
| AbD22634.1 | Ag05681 | hIgE | 0.69 | pH 4 |
| AbD22635.1 | Ag05681 | hIgE | 1.72 | pH 5 |
| AbD22636.1 | Ag05681 | hIgE | 1.70 | pH 5 |
| AbD22637.1 | Ag05681 | hIgE | 1.20 | pH 5 |
| AbD22638.1 | Ag05681 | hIgE | 1.70 | pH 5 |
| AbD22639.1 | Ag05681 | hIgE | 1.37 | pH 5 |
| AbD22640.1 | Ag05681 | hIgE | 1.58 | pH 5 |
| AbD22641.1 | Ag05681 | hIgE | 1.76 | pH 5 |
| AbD22642.1 | Ag05681 | hIgE | 0.90 | pH 5 |
| AbD22643.1 | Ag05681 | hIgE | 1.69 | pH 5 |

Example 3

Selected antibody Fab fragments isolated as described in Example 2 were used as affinity ligands to purify an immunoglobulin target. Two anti-IgM antibody Fab fragments were selected as representative affinity ligands: AbD20771 and AbD20775. The affinity ligands were expressed in *E. coli* as monomers having a FLAG-His6 tag on the heavy chain. The ligands were purified using Ni-NTA agarose.

Four hIgM molecules were selected as exemplary target molecules to assess the purification capability of the ligands. These ligands are set forth in Table 9. Supernatant containing these ligands was collected during culturing of the cell lines noted in Table 9. OBT1524 hIgM (AbD Serotec, Bio-Rad), an IgM protein purified from myeloma serum, was used as a standard control.

TABLE 9

IgM Target Molecules For Purification

| Target Molecule | Cell Line Expression |
|---|---|
| AbD00264 hIgM lambda (AbD Serotec, BioRad) | Expression in a stable human HKB11 cell pool (AbD Serotec, BioRad) |
| AbD18705 hIgM kappa (AbD Serotec, BioRad) | Expression in a stable human HKB11 cell pool (AbD Serotec, BioRad) |
| AbD18777 hIgM kappa (AbD Serotec, BioRad) | Transient expression in human HKB11 cell line (AbD Serotec, BioRad) |

The purified affinity ligands were coupled to 1 ml "HiTrap NETS-activated HP" columns according to manufacture's protocol (GE Healthcare #17-0716-01), with 7 mg of the ligand being applied to the column. The columns were run on a GE ÄKTAxpress™ FPLC instrument. The supernatant sample (200 ml) was loaded using a flow rate of 0.4 ml/min (62 cm/h; retention time of 2.4 min) using PBS (pH about 7.0-7.2) as binding and washing buffer. The elution buffer was 100 mM citrate, 150 mM NaCl, pH 4.0. Following elution, a neutralization buffer (1 M Tris/HCl pH 9.0) was used to neutralize the pH of the purified IgM targets.

Figure 10:
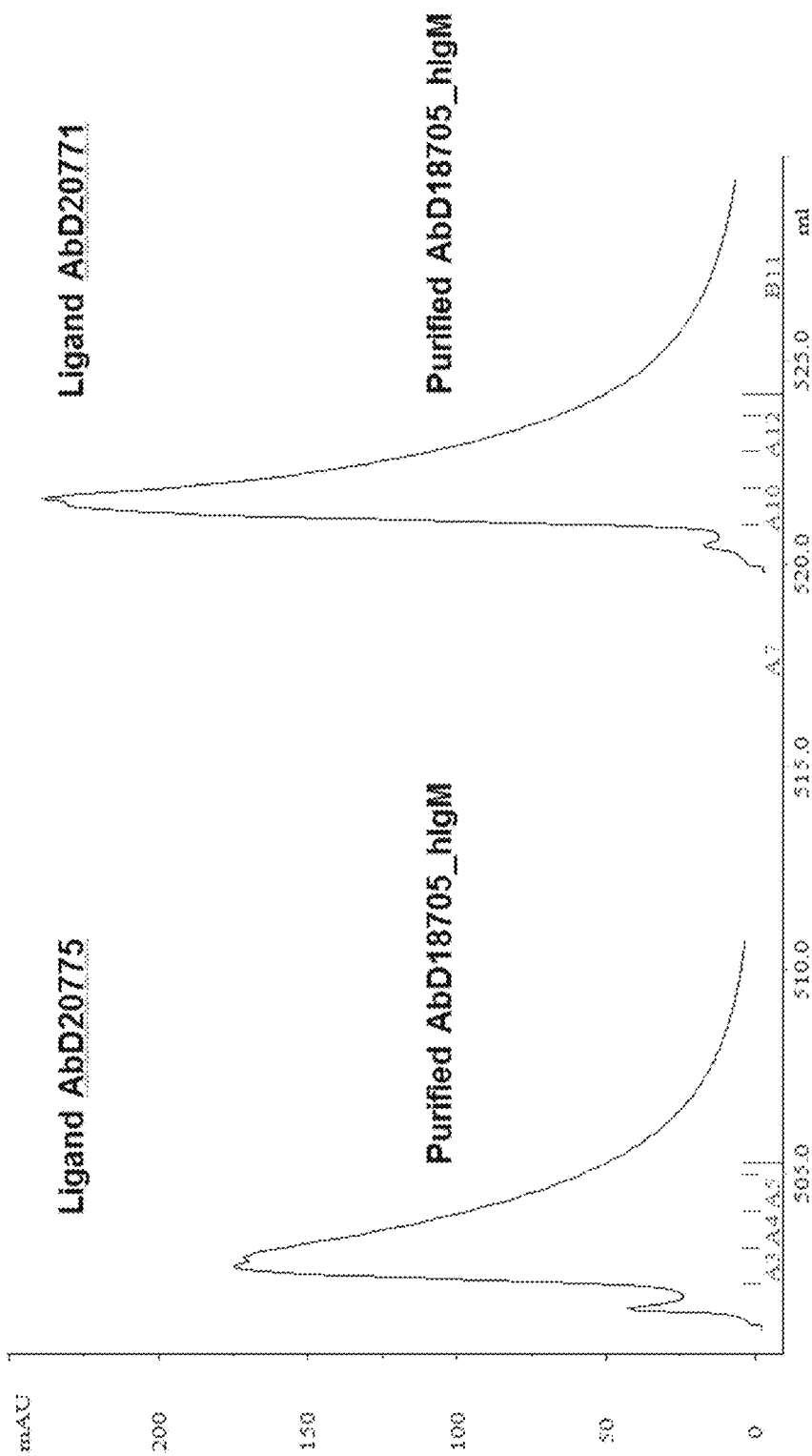
FIG. 10 shows elution profiles of purified AbD18705 hIgM target molecule from affinity ligand columns according to one example. The affinity column on the left uses anti-IgM antibody ligand AbD20775.2, and the affinity column on the right uses anti-IgM antibody ligand AbD20771.2. Collected fractions (A#) are shown across the bottom of each graph.

Exemplary results are shown for target molecule AbD18705 IgM. Results for the other two target molecules were similar. Elution profiles (UV 280 nm) are shown in FIG. 10 (collected fractions are indicated). The AbD18705 IgM target molecule is captured from cell culture supernatant and eluted under mild conditions (pH 4.0) using both affinity ligand AbD20771 and AbD20775.

Figure 11:
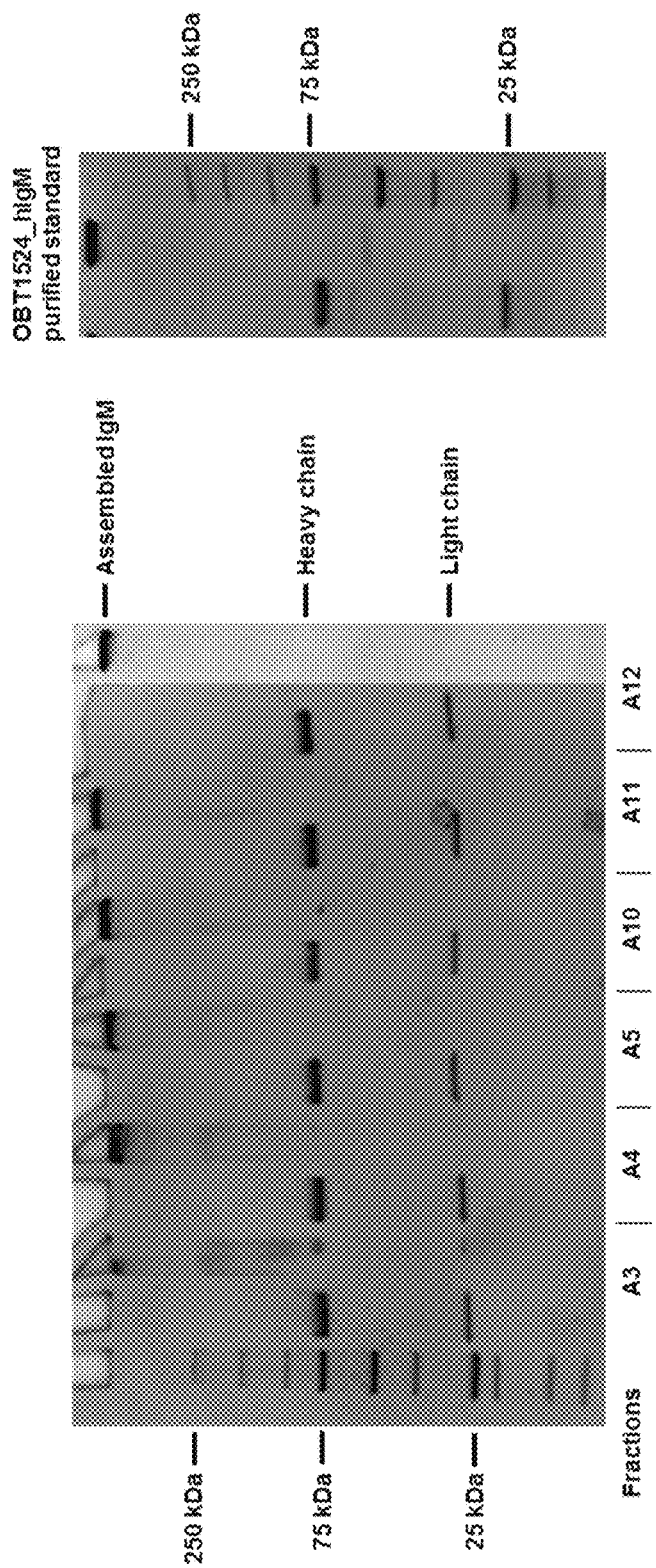
FIG. 11 shows SDS-PAGE analysis of purified AbD18705 hIgM target molecule elution fractions according to one example. The left gel shows the purified AbD18705 hIgM from the indicated fractions (each fraction shown under reducing and under oxidizing conditions). Purified human IgM (product number OBT1524) is shown as a control in the gel on the right, again under reducing and oxidizing conditions.

To assess the purity and integrity of the purified target molecules, the purified protein fractions (A3/4/5 for the AbD20775 column and A10/11/12 for the AbD20771 column, as identified in FIG. 10; 1 µg protein/lane) were run on 4-20% Mini-PROTEAN™ Stain-free TGX gels (Bio-Rad). Exemplary reducing and non-reducing lanes are shown for each fraction, respectively, in FIG. 11. Comparisons were made to the purified OBT1524 IgM standard control protein (FIG. 11, right panel). The purity of the AbD18705 IgM target molecule in the fractions is high under reducing conditions and both heavy and light chains can be detected. Under non-reducing conditions, assembled IgM is detectable.

Figure 12:
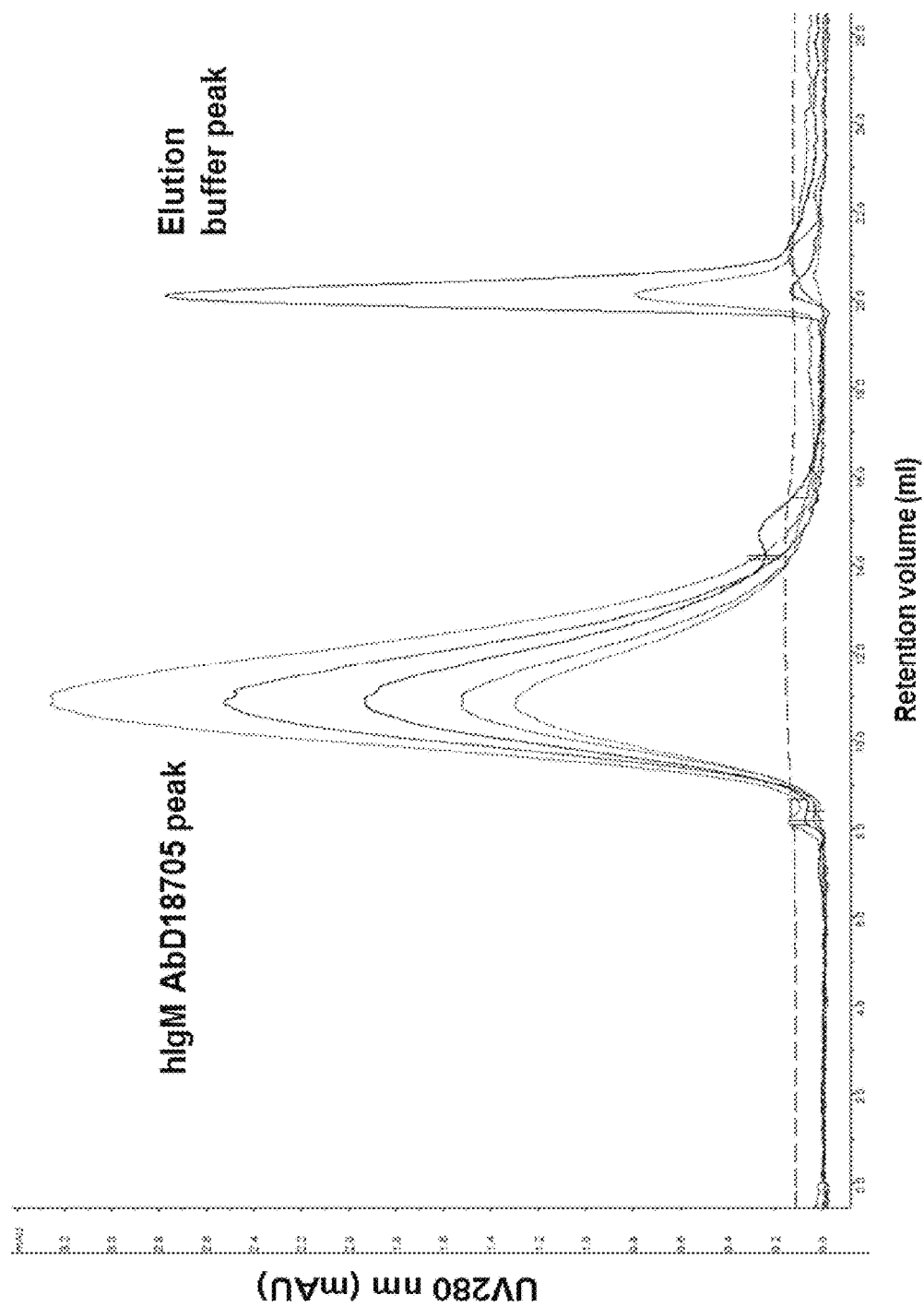
FIG. 12 shows an overlay of size exclusion chromatography runs for purified AbD18705 hIgM target molecule elution fractions identified in FIG. 10 according to one example.

Size exclusion chromatography (SEC) using a Superose 6 SEC column (GE Healthcare) was also performed to assess the integrity of the purified target molecules. FIG. 12 shows an overlay of SEC runs (UV280 nm signal) for fractions A4/5/10/11/12 as identified in FIG. 10. The peak retention volume was 10.8 ml, corresponding to a MW of 916 kDa (calculated MW for IgM AbD18705 in pentameric form without glycosylation is 859 kDa. All fractions show an identical elution behaviour indicating that assembled, non-aggregated IgM is present in the fractions. No degradation or aggregation is visible.

Figure 13:
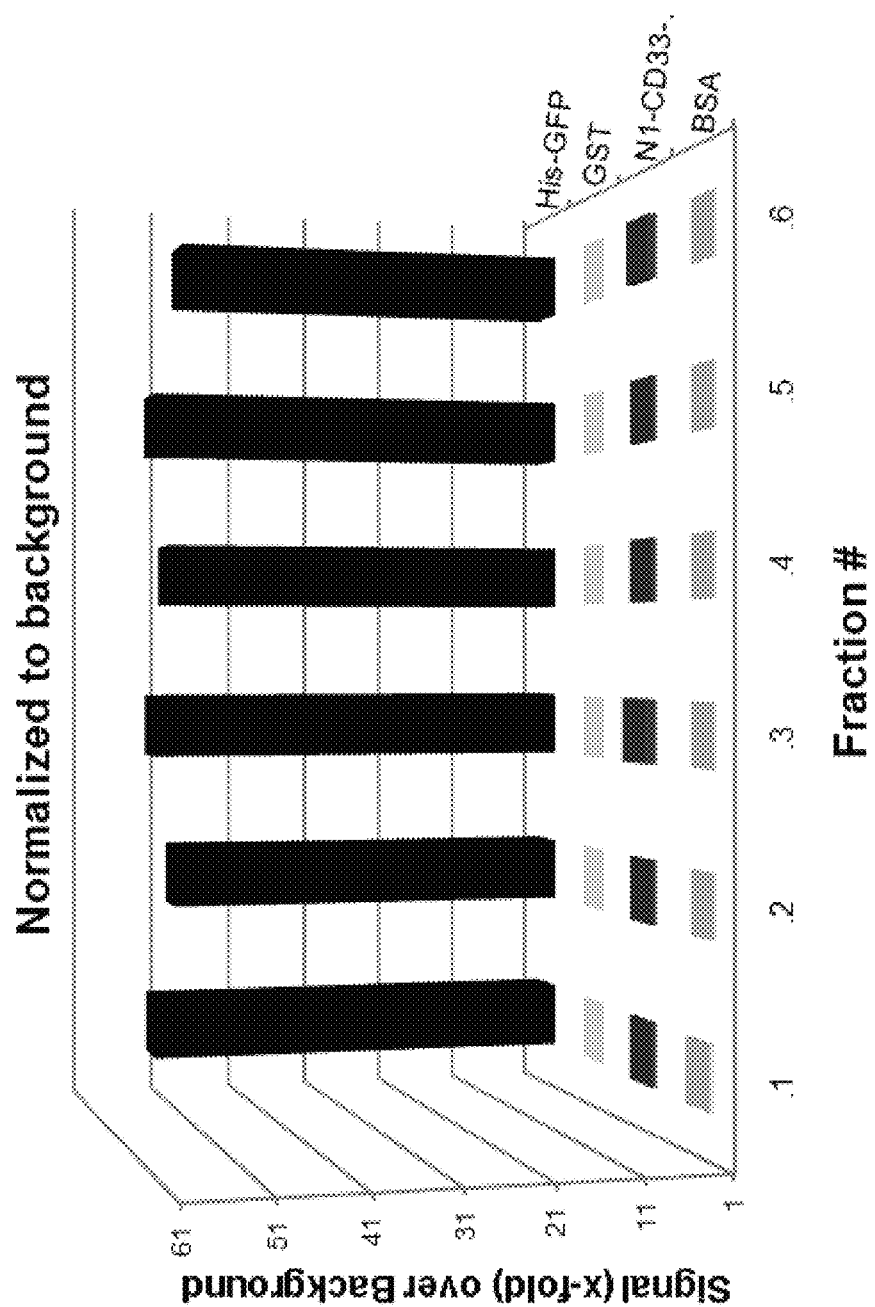
FIG. 13 shows a graph illustrating the results of an ELISA assay assessing the activity and specificity of the purified AbD18705 hIgM target molecule ("His-GFP") for its antigen GFP according to one example. Controls GST, N1-CD33-6×His, and BSA are also shown.

Finally, ELISA analysis of the various fractions was performed to assess activity and specificity of the purified AbD18705 hIgM target molecule. Negative control antigens (BSA, N1-CD33-6×His, GST) were coated at 5 µg/ml onto the ELISA plate along with the specific antigen His-GFP, which is the antigen of AbD18705. The six fractions A3/4/5 and A10/11/12 of the purified IgM AbD18705, numbered 1 to 6 here, were added (20 µl each) after washing, blocking and additional washing. Detection was performed using an anti-human IgM HRP conjugate (AbD Serotec) in combination with Quantablu™ substrate. As shown in FIG. 13, the purified AbD18705 hIgM antibody fractions all recognize the His-GFP antigen specifically and, thus, have a native active conformation.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

---

What is claimed is:

1. An affinity ligand that binds specifically to a target molecule, wherein the specific binding strength of the affinity ligand to the target molecule is reduced under buffer conditions comprising (i) a pH of 4.0 to 5.5 or (ii) 1-2 M $MgCl_2$, wherein the affinity ligand is an anti-IgM antibody comprising at least one of (i) or (ii) as follows:
  (i) heavy chain complementarity determining regions CDR1, CDR2, and CDR3 sequences selected from:
  SEQ ID NO:223, SEQ ID NO:231, and SEQ ID NO:239, respectively; or
  SEQ ID NO:224, SEQ ID NO:232, and SEQ ID NO:240, respectively; or
  SEQ ID NO:225, SEQ ID NO:233, and SEQ ID NO:241, respectively; or
  SEQ ID NO:226, SEQ ID NO:234, and SEQ ID NO:242, respectively; or
  SEQ ID NO:227, SEQ ID NO:235, and SEQ ID NO:243, respectively; or
  SEQ ID NO:228, SEQ ID NO:236, and SEQ ID NO:244, respectively; or
  SEQ ID NO:229, SEQ ID NO:237, and SEQ ID NO:245, respectively;
  SEQ ID NO:230, SEQ ID NO:238, and SEQ ID NO:246, respectively, or
  (ii) light chain complementarity determining regions CDR1, CDR2, and CDR3 sequences selected from:
  SEQ ID NO:247, SEQ ID NO:255, and SEQ ID NO:263, respectively; or
  SEQ ID NO:248, SEQ ID NO:256, and SEQ ID NO:264, respectively; or
  SEQ ID NO:249, SEQ ID NO:257, and SEQ ID NO:265, respectively; or
  SEQ ID NO:250, SEQ ID NO:258, and SEQ ID NO:266, respectively; or
  SEQ ID NO:251, SEQ ID NO:259, and SEQ ID NO:267, respectively; or
  SEQ ID NO:252, SEQ ID NO:260, and SEQ ID NO:268, respectively; or
  SEQ ID NO:253, SEQ ID NO:261, and SEQ ID NO:269, respectively; or
  SEQ ID NO:254, SEQ ID NO:262, and SEQ ID NO:270, respectively.

2. The affinity ligand of claim 1, wherein the affinity ligand is (i) an immunoglobulin or (ii) a recombinant Fab fragment or Fab fragment derivative.

3. The affinity ligand of claim 1, wherein the affinity ligand is linked to a solid support.

4. A method of isolating a target molecule, the method comprising the steps of:
  a) providing a solid support linked to the affinity ligand of claim 1;
  b) contacting the solid support with a sample containing the target molecule;
  c) washing the solid support with a wash buffer to remove unbound components of the sample; and
  d) eluting bound target molecule from the solid support with an elution buffer comprising (i) a pH of 4.0 to 5.5 or (ii) 1-2 M $MgCl_2$.

5. The method of claim 4, wherein the eluting comprises:
  (i) a single-step elution with an elution buffer comprising (i) a pH of 4.0 to 5.5 or (ii) 1-2 M $MgCl_2$;
  (ii) a multiple-step elution with a plurality of elution buffers comprising (i) a pH of 4.0 to 5.5 or (ii) 1-2 M $MgCl_2$, wherein the plurality of elution buffers are applied to the solid support sequentially, wherein elution buffers having higher salt concentrations are applied after elution buffers having lower salt concentrations and elution buffers having lower pH are applied after elution buffers having higher pH;
  (iii) a gradient elution with an elution buffer having a gradient of linearly increasing salt concentration during the time of the eluting, wherein the maximum salt concentration is 1-2 M $MgCl_2$; or
  (iv) a gradient elution with an elution buffer having a gradient of linearly decreasing pH during the time of the eluting, wherein the minimum pH is 4.0.

6. A kit comprising the affinity ligand of claim 1.

7. The affinity ligand of claim 1, wherein
  the heavy chain CDR1, CDR2, and CDR3 are SEQ ID NO:223, SEQ ID NO:231, and SEQ ID NO:239, respectively; and
  the light chain CDR1, CDR2, and CDR3 are SEQ ID NO:247, SEQ ID NO:255, and SEQ ID NO:263, respectively.

8. The affinity ligand of claim 1, wherein
  the heavy chain CDR1, CDR2, and CDR3 are SEQ ID NO:224, SEQ ID NO:232, and SEQ ID NO:240, respectively; and
  the light chain CDR1, CDR2, and CDR3 are SEQ ID NO:248, SEQ ID NO:256, and SEQ ID NO:264, respectively.

9. The affinity ligand of claim 1, wherein
  the heavy chain CDR1, CDR2, and CDR3 are SEQ ID NO:225, SEQ ID NO:233, and SEQ ID NO:241, respectively; and the light chain CDR1, CDR2, and CDR3 are SEQ ID NO:249, SEQ ID NO:257, and SEQ ID NO:265, respectively.

10. The affinity ligand of claim 1, wherein
the heavy chain CDR1, CDR2, and CDR3 are SEQ ID NO:226, SEQ ID NO:234, and SEQ ID NO:242, respectively; and
the light chain CDR1, CDR2, and CDR3 are SEQ ID NO:250, SEQ ID NO:258, and SEQ ID NO:266, respectively.

11. The affinity ligand of claim 1, wherein
the heavy chain CDR1, CDR2, and CDR3 are SEQ ID NO:227, SEQ ID NO:235, and SEQ ID NO:243, respectively; and
the light chain CDR1, CDR2, and CDR3 are SEQ ID NO:251, SEQ ID NO:259, and SEQ ID NO:267, respectively.

12. The affinity ligand of claim 1, wherein
the heavy chain CDR1, CDR2, and CDR3 are SEQ ID NO:228, SEQ ID NO:236, and SEQ ID NO:244, respectively; and
the light chain CDR1, CDR2, and CDR3 are SEQ ID NO:252, SEQ ID NO:260, and SEQ ID NO:268, respectively.

13. The affinity ligand of claim 1, wherein
the heavy chain CDR1, CDR2, and CDR3 are SEQ ID NO:229, SEQ ID NO:237, and SEQ ID NO:245, respectively; and
the light chain CDR1, CDR2, and CDR3 are SEQ ID NO:253, SEQ ID NO:261, and SEQ ID NO:269, respectively.

14. The affinity ligand of claim 1, wherein
the heavy chain CDR1, CDR2, and CDR3 are SEQ ID NO:230, SEQ ID NO:238, and SEQ ID NO:246, respectively; and
the light chain CDR1, CDR2, and CDR3 are SEQ ID NO:254, SEQ ID NO:262, and SEQ ID NO:270, respectively.

* * * * *

SEQUENCE LISTING

```
<160> NUMBER OF SEQ ID NOS: 288

<210> SEQ ID NO 1
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 1

Gly Tyr Ser Phe Ser Ser Tyr Trp Ile Thr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 2

Gly Tyr Thr Phe Thr Gly Tyr Asp Ile His
1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 3

Gly Gly Thr Phe Ser Asp Tyr Ala Ile Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 4

Gly Gly Thr Phe Ser Thr Tyr Ala Ile Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 5

Gly Tyr Ser Phe Thr Ser Tyr Trp Ile Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic affinity ligand peptide sequence

<400> SEQUENCE: 6

Gly Asp Ser Val Ser Arg Asn Ser Ala Ala Trp Asn
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 7

Gly Gly Thr Phe Ser Ser Tyr Tyr Ile His
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 8

Gly Phe Thr Phe Ser Ser Tyr Val Met Thr
1               5                   10

```
<210> SEQ ID NO 9
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 9

Gly Gly Thr Phe Asn Ser Tyr Ala Ile His
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 10

Gly Gly Thr Phe Ser Asp Tyr Ala Ile Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 11

Gly Phe Thr Phe Ser Ser Tyr Ala Ile Ser
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 12

Gly Gly Thr Phe Ser Asp Tyr Ala Ile Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 13

Gly Phe Thr Phe Ser Thr Tyr Ala Met His
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 14

Gly Phe Thr Phe Arg Ser His Gly Met Ser
1               5                   10

<210> SEQ ID NO 15
```

```
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 15

Gly Phe Thr Phe Arg Ser His Gly Met Ser
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 16

Gly Tyr Thr Phe Thr Gly Tyr Tyr Met Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 17

Gly Phe Thr Phe Ser Asp Tyr Ala Ile His
1               5                   10

<210> SEQ ID NO 18
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 18

Trp Met Gly Thr Ile Phe Pro Asp Asp Ser Tyr Thr Ile Tyr Ser Pro
1               5                   10                  15

Ser Phe Gln Gly
            20

<210> SEQ ID NO 19
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 19

Trp Met Gly Trp Ile Ala Pro Tyr Asn Gly Gly Thr Asn Tyr Ala Gln
1               5                   10                  15

Lys Phe Gln Gly
            20

<210> SEQ ID NO 20
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 20
```

Trp Met Gly Gly Ile Ile Pro Ile Phe Gly Thr Ala Asn Tyr Ala Gln
1               5                   10                  15

Lys Phe Gln Gly
            20

<210> SEQ ID NO 21
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 21

Trp Met Gly Gly Ile Ile Pro Ile Phe Gly Thr Ala Asp Tyr Ala Gln
1               5                   10                  15

Lys Phe Gln Gly
            20

<210> SEQ ID NO 22
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 22

Trp Met Gly Ile Ile Asp Pro Ser Asn Ser Asp Thr Arg Tyr Ser Pro
1               5                   10                  15

Ser Phe Gln Gly
            20

<210> SEQ ID NO 23
<211> LENGTH: 21
<212> TYPE: PRT
<213> ORGANISM: Artificial Sequence
<220> FEATURE:
<223> OTHER INFORMATION: synthetic affinity ligand peptide sequence

<400> SEQUENCE: 23

Trp Leu Gly Arg Ile Gln Tyr Arg Ser Lys Trp Ile Asn Asp Tyr Ala
1               5                   10                  15

Val Ser Val Lys Ser
            20

<210> SEQ ID NO 24
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 24

Trp Met Gly Gly Ile Gly Pro Ile Phe Gly Val Ala Asn Tyr Ala Gln
1               5                   10                  15

Lys Phe Gln Gly
            20

<210> SEQ ID NO 25
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 25

```
Trp Val Ser Ala Ile Ser Tyr Asp Gly Ser Ser Thr Tyr Tyr Ala Asp
1               5                   10                  15

Ser Val Lys Gly
            20

<210> SEQ ID NO 26
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 26

Trp Met Gly Gly Ile Ala Pro Ile Phe Gly Thr Ala Asn Tyr Ala Gln
1               5                   10                  15

Lys Phe Gln Gly
            20

<210> SEQ ID NO 27
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 27

Trp Met Gly Gly Ile Glu Pro Val Phe Gly Thr Ala Lys Tyr Ala Gln
1               5                   10                  15

Lys Phe Gln Gly
            20

<210> SEQ ID NO 28
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 28

Trp Val Ser Tyr Ile Ser Ser Gly Gly Ser Glu Thr Tyr Tyr Ala Asp
1               5                   10                  15

Ser Val Lys Gly
            20

<210> SEQ ID NO 29
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 29

Trp Met Gly Gly Ile Ser Pro Asp Phe Gly Thr Ala Asn Tyr Ala Gln
1               5                   10                  15

Lys Phe Gln Gly
            20

<210> SEQ ID NO 30
<211> LENGTH: 22
<212> TYPE: PRT
<213> ORGANISM: Artificial Sequence
<220> FEATURE:
<223> OTHER INFORMATION: synthetic affinity ligand peptide sequence
```

```
<400> SEQUENCE: 30

Trp Val Gly Arg Ile Lys Ser Lys Gln Asp Gly Gly Thr Thr Asp Tyr
1               5                   10                  15

Ala Ala Pro Val Lys Gly
            20

<210> SEQ ID NO 31
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 31

Trp Val Ser Thr Ile Ser Gly Ser Gly Ser Asn Thr Tyr Tyr Ala Asp
1               5                   10                  15

Ser Val Lys Gly
            20

<210> SEQ ID NO 32
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 32

Trp Val Ser Thr Ile Ser Gly Ser Gly Ser Asn Thr Tyr Tyr Ala Asp
1               5                   10                  15

Ser Val Lys Gly
            20

<210> SEQ ID NO 33
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 33

Trp Met Gly Tyr Ile Ser Pro Tyr Ser Gly Lys Thr Asn Tyr Ala Gln
1               5                   10                  15

Lys Phe Gln Gly
            20

<210> SEQ ID NO 34
<211> LENGTH: 22
<212> TYPE: PRT
<213> ORGANISM: Artificial Sequence
<220> FEATURE:
<223> OTHER INFORMATION: synthetic affinity ligand peptide sequence

<400> SEQUENCE: 34

Trp Val Gly Arg Ile Lys Ser His Ala Tyr Gly Gly Thr Thr Asp Tyr
1               5                   10                  15

Ala Ala Pro Val Lys Gly
            20

<210> SEQ ID NO 35
<211> LENGTH: 14
<212> TYPE: PRT
<213> ORGANISM: Artificial Sequence
<220> FEATURE:
<223> OTHER INFORMATION: synthetic affinity ligand peptide sequence
```

```
<400> SEQUENCE: 35

Met Gly Tyr Tyr Thr Ala Gly Gln Ala His Ala Tyr Asp Phe
1               5                   10

<210> SEQ ID NO 36
<211> LENGTH: 17
<212> TYPE: PRT
<213> ORGANISM: Artificial Sequence
<220> FEATURE:
<223> OTHER INFORMATION: synthetic affinity ligand peptide sequence

<400> SEQUENCE: 36

Asp Met Gly Thr Ser Tyr Leu Pro Ser Asn Trp Ser Tyr Pro Phe Ala
1               5                   10                  15

Tyr

<210> SEQ ID NO 37
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 37

Ser Arg Ala Ser Tyr Ser Tyr Gly Phe Asp Tyr
1               5                   10

<210> SEQ ID NO 38
<211> LENGTH: 15
<212> TYPE: PRT
<213> ORGANISM: Artificial Sequence
<220> FEATURE:
<223> OTHER INFORMATION: synthetic affinity ligand peptide sequence

<400> SEQUENCE: 38

Ser Gln Arg Gly Gly Ala Ser Val Tyr Ser Tyr Ala Phe Asp Ile
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 39

Gly Arg Gly Tyr Ser Tyr Pro Phe Asp Tyr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 40

Asp Ser Tyr Thr Ser Thr Gly Gly Met Asp Ile
1               5                   10

<210> SEQ ID NO 41
<211> LENGTH: 12
<212> TYPE: PRT
<213> ORGANISM: Artificial Sequence
<220> FEATURE:
```

<223> OTHER INFORMATION: synthetic affinity ligand peptide sequence

<400> SEQUENCE: 41

Asp His Ser Tyr Tyr Pro Val Phe Tyr Phe Asp Asn
1               5                   10

<210> SEQ ID NO 42
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 42

Ser Glu Tyr Ala Ile Val Tyr Phe Asp Tyr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 43

Ser Arg Thr Leu Val Ser Gly Tyr Tyr Pro Phe Asp Val
1               5                   10

<210> SEQ ID NO 44
<211> LENGTH: 12
<212> TYPE: PRT
<213> ORGANISM: Artificial Sequence
<220> FEATURE:
<223> OTHER INFORMATION: synthetic affinity ligand peptide sequence

<400> SEQUENCE: 44

Met Gly Tyr Tyr Pro Pro Ala Gly Ala Met Asp Val
1               5                   10

<210> SEQ ID NO 45
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 45

Val Arg Gly Tyr Tyr Ser Tyr Pro Phe Asp Val
1               5                   10

<210> SEQ ID NO 46
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 46

Ser Ile Lys Thr Tyr Tyr Val Tyr Gln Ala Phe Asp His
1               5                   10

<210> SEQ ID NO 47
<211> LENGTH: 15
<212> TYPE: PRT
<213> ORGANISM: Artificial Sequence
<220> FEATURE:
<223> OTHER INFORMATION: synthetic affinity ligand peptide sequence -continued

<400> SEQUENCE: 47

Thr Arg Arg Gly Thr Trp Tyr Arg Tyr Ala Arg Ser Leu Asp Val
1               5                   10                  15

<210> SEQ ID NO 48
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 48

Tyr Ala Tyr Ala Ala Gly Thr Ile Phe Asp Val
1               5                   10

<210> SEQ ID NO 49
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 49

Tyr Ala Tyr Ala Ala Gly Thr Ile Phe Asp Val
1               5                   10

<210> SEQ ID NO 50
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 50

Glu Met Gly Tyr Tyr Gln Gly Phe Asp Ile
1               5                   10

<210> SEQ ID NO 51
<211> LENGTH: 6
<212> TYPE: PRT
<213> ORGANISM: Artificial Sequence
<220> FEATURE:
<223> OTHER INFORMATION: synthetic affinity ligand peptide sequence

<400> SEQUENCE: 51

Glu Ser Tyr Phe Asp Tyr
1               5

<210> SEQ ID NO 52
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 52

Ser Gly Asp Lys Ile Gly Lys Lys Tyr Ala Tyr
1               5                   10

<210> SEQ ID NO 53
<211> LENGTH: 11
<212> TYPE: PRT
<213> ORGANISM: Artificial Sequence
<220> FEATURE:
<223> OTHER INFORMATION: synthetic affinity ligand peptide sequence

```
<400> SEQUENCE: 53

Ser Gly Asp Asn Ile Gly Ser Lys Phe Ala Ser
1               5                   10

<210> SEQ ID NO 54
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 54

Ser Gly Asp Asn Leu Gly Asp Lys Phe Ala His
1               5                   10

<210> SEQ ID NO 55
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 55

Ser Gly Asp Ala Leu Gly Thr Gln Phe Ala His
1               5                   10

<210> SEQ ID NO 56
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 56

Ser Gly Asp Ala Leu Pro Thr Met Phe Ala His
1               5                   10

<210> SEQ ID NO 57
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 57

Ser Gly Asp Ser Leu Val Lys Lys His Ala Ser
1               5                   10

<210> SEQ ID NO 58
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 58

Ser Gly Asp Asn Leu Gly Lys Lys Tyr Val His
1               5                   10

<210> SEQ ID NO 59
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 59
```

```
Arg Ala Ser Gln Gly Ile Ser Ser Tyr Leu Asn
1               5                   10

<210> SEQ ID NO 60
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 60

Ser Gly Asp Asn Leu Gly Phe Lys Phe Ala His
1               5                   10

<210> SEQ ID NO 61
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 61

Ser Gly Asp Asn Ile Arg Thr Gln Phe Val Gln
1               5                   10

<210> SEQ ID NO 62
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 62

Ser Gly Asp Ala Ile Gly Asp Lys Phe Val His
1               5                   10

<210> SEQ ID NO 63
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 63

Ser Gly Asp Ala Leu Gly Thr Lys Tyr Val His
1               5                   10

<210> SEQ ID NO 64
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 64

Ser Gly Ser Ser Ser Asn Ile Gly Tyr Asn Tyr Val Ser
1               5                   10

<210> SEQ ID NO 65
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 65
```

Ser Gly Ser Ser Ser Asn Ile Gly Ala Asn Thr Val Ser
1               5                   10

<210> SEQ ID NO 66
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 66

Ser Gly Ser Ser Ser Asn Ile Gly Ala Asn Thr Val Ser
1               5                   10

<210> SEQ ID NO 67
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 67

Arg Ala Ser Gln Ser Ile Ile Asn Tyr Leu Asn
1               5                   10

<210> SEQ ID NO 68
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 68

Ser Gly Asp Asn Leu Gly Glu Lys Phe Val His
1               5                   10

<210> SEQ ID NO 69
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 69

Leu Val Ile Tyr Ser Asp Asn Asn Arg Pro Ser
1               5                   10

<210> SEQ ID NO 70
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 70

Leu Val Ile Tyr Asp Asp Ser Lys Arg Pro Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 71

Leu Val Ile Tyr Asp Asp Asn Asp Arg Pro Ser

```
1               5                   10
```

<210> SEQ ID NO 72
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 72

```
Leu Val Ile Tyr Asp Asp Asn Lys Arg Pro Ser
1               5                   10
```

<210> SEQ ID NO 73
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 73

```
Leu Val Ile Tyr Asp Asp Asn Lys Arg Pro Ser
1               5                   10
```

<210> SEQ ID NO 74
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 74

```
Leu Val Ile Tyr Asp Asp Asp Lys Arg Pro Ser
1               5                   10
```

<210> SEQ ID NO 75
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 75

```
Pro Val Ile Tyr Asp Asp Ser Lys Arg Pro Ser
1               5                   10
```

<210> SEQ ID NO 76
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 76

```
Leu Leu Ile Tyr Ser Ala Ser Asn Leu Gln Ser
1               5                   10
```

<210> SEQ ID NO 77
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 77

```
Leu Val Ile Tyr Asp Asp Ser Asn Arg Pro Ser
1               5                   10
```

```
<210> SEQ ID NO 78
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 78

Leu Val Ile Tyr Asp Asp Asn His Arg Pro Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 79

Leu Val Ile Tyr Asp Asp Ser Lys Arg Pro Ser
1               5                   10

<210> SEQ ID NO 80
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 80

Leu Val Ile Ser Asp Asp Asn Glu Arg Pro Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 81

Leu Leu Ile Tyr Ser Asn Thr Lys Arg Pro Ser
1               5                   10

<210> SEQ ID NO 82
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 82

Leu Leu Ile Tyr Gly Asn Ile Gln Arg Pro Ser
1               5                   10

<210> SEQ ID NO 83
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 83

Leu Leu Ile Tyr Gly Asn Ile Gln His Pro Ser
1               5                   10
```

<210> SEQ ID NO 84
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 84

Leu Leu Ile Ser Asp Ala Ser Ser Leu Gln Ser
1               5                   10

<210> SEQ ID NO 85
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 85

Leu Val Ile Tyr Tyr Asp Asn His Arg Pro Ser
1               5                   10

<210> SEQ ID NO 86
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 86

Tyr Val Thr Asp Gly Tyr Phe Thr Thr Gly
1               5                   10

<210> SEQ ID NO 87
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 87

Tyr Ser Arg Ala Gln Ser Gly Ser Pro Val
1               5                   10

<210> SEQ ID NO 88
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 88

Gln Ser Tyr Asp Ser Ser Ser Ser Leu Arg
1               5                   10

<210> SEQ ID NO 89
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 89

Gln Ser Ala Asp Trp Met Asp Tyr
1               5

```
<210> SEQ ID NO 90
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 90

Ala Ser Tyr Ala Ser Ser Leu Asn Pro Val
1               5                   10

<210> SEQ ID NO 91
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 91

Ala Ser Tyr Asp Gly Trp Gly Asn Glu Arg
1               5                   10

<210> SEQ ID NO 92
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 92

Gln Ser Tyr Asp Arg Ser Leu Asp Phe Asn
1               5                   10

<210> SEQ ID NO 93
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 93

Gln Gln Gly Ile Ser Trp Leu Arg
1               5

<210> SEQ ID NO 94
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 94

Ser Ser Tyr Asp Tyr Ser Ser Val
1               5

<210> SEQ ID NO 95
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 95

Ala Ser Arg Asp Lys Ser Ala Asn Ser Val
1               5                   10

<210> SEQ ID NO 96
```

```
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 96

Gln Ser Tyr Asp Phe Gly Gly Asn Gly Ile
1               5                   10

<210> SEQ ID NO 97
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 97

Gln Ser Tyr Asp Phe Ser Ala Ser Ser Val
1               5                   10

<210> SEQ ID NO 98
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 98

Gln Ser Arg Ala His Gly Gly Asn Ser Ile
1               5                   10

<210> SEQ ID NO 99
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 99

Ala Ala Tyr Asp Ala Ile Phe Asn Lys Ile
1               5                   10

<210> SEQ ID NO 100
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 100

Ala Ala Tyr Asp Ala Ile Phe Asn Lys Ile
1               5                   10

<210> SEQ ID NO 101
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 101

Gln Gln Asn Leu Ser Gly Pro Phe
1               5

<210> SEQ ID NO 102
<211> LENGTH: 8
```

```
<212> TYPE: PRT
<213> ORGANISM: Artificial Sequence
<220> FEATURE:
<223> OTHER INFORMATION: synthetic affinity ligand peptide sequence

<400> SEQUENCE: 102

Ala Ser Trp Asp Ile Glu Ser Val
1               5

<210> SEQ ID NO 103
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 103

Gly Gly Thr Phe Ser Ser Tyr Ser Ile Ser
1               5                   10

<210> SEQ ID NO 104
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 104

Gly Gly Thr Phe Arg Ser Tyr Ala Ile Ser
1               5                   10

<210> SEQ ID NO 105
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 105

Gly Gly Thr Phe Ser Ser Tyr Ala Ile Ser
1               5                   10

<210> SEQ ID NO 106
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 106

Gly Gly Thr Phe Ser Ser Tyr Ser Ile Ser
1               5                   10

<210> SEQ ID NO 107
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 107

Gly Gly Thr Phe Ser Ser Asn Thr Ile Ser
1               5                   10

<210> SEQ ID NO 108
<211> LENGTH: 10
<212> TYPE: PRT
```

<213> ORGANISM: Artificial Sequence
<220> FEATURE:
<223> OTHER INFORMATION: synthetic affinity ligand peptide sequence

<400> SEQUENCE: 108

Gly Gly Thr Phe Ser Ser Tyr Ala Ile Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 109

Gly Tyr Thr Phe Thr Ser Tyr Tyr Ile His
1               5                   10

<210> SEQ ID NO 110
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 110

Gly Gly Thr Phe Ser Ser Tyr Ala Ile Asn
1               5                   10

<210> SEQ ID NO 111
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 111

Gly Gly Thr Phe Ser Ser Tyr Ala Ile Ser
1               5                   10

<210> SEQ ID NO 112
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 112

Gly Gly Thr Phe Ser Ser Tyr Ala Ile Gly
1               5                   10

<210> SEQ ID NO 113
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 113

Gly Gly Thr Phe Ser Ser Tyr Ala Ile Ser
1               5                   10

<210> SEQ ID NO 114
<211> LENGTH: 10
<212> TYPE: PRT
<213> ORGANISM: Artificial Sequence

```
<220> FEATURE:
<223> OTHER INFORMATION: synthetic affinity ligand peptide sequence

<400> SEQUENCE: 114

Gly Gly Thr Phe Ser Ser Tyr Ala Ile Asn
1               5                   10

<210> SEQ ID NO 115
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 115

Gly Gly Thr Phe Ser Gly Tyr Gly Ile Ser
1               5                   10

<210> SEQ ID NO 116
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 116

Gly Phe Thr Phe Ser Asp Tyr Gly Leu His
1               5                   10

<210> SEQ ID NO 117
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 117

Gly Gly Thr Phe Ser Ser Tyr Ala Val Asn
1               5                   10

<210> SEQ ID NO 118
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 118

Gly Gly Thr Phe Ser Ser Tyr Ala Ile Ser
1               5                   10

<210> SEQ ID NO 119
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 119

Gly Gly Thr Phe Ser Thr Tyr Ala Ile Ser
1               5                   10

<210> SEQ ID NO 120
<211> LENGTH: 10
<212> TYPE: PRT
<213> ORGANISM: Artificial Sequence
<220> FEATURE:
```

```
<223> OTHER INFORMATION: synthetic affinity ligand peptide sequence

<400> SEQUENCE: 120

Gly Gly Thr Phe Arg Ser Tyr Ala Val His
1               5                   10

<210> SEQ ID NO 121
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 121

Gly Gly Thr Phe Ser Asp Asn Ala Ile Ser
1               5                   10

<210> SEQ ID NO 122
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 122

Gly Gly Thr Phe Ser Ser Tyr Ala Ile Ser
1               5                   10

<210> SEQ ID NO 123
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 123

Trp Met Gly Gly Ile Ile Pro Ile Phe Gly Ile Ala Ser Tyr Ala Gln
1               5                   10                  15

Lys Phe Gln Gly
            20

<210> SEQ ID NO 124
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 124

Trp Met Gly Gly Ile Ile Pro Arg Phe Gly Ile Ala Asn Tyr Ala Gln
1               5                   10                  15

Lys Phe Gln Gly
            20

<210> SEQ ID NO 125
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 125

Trp Met Gly Gly Ile Tyr Pro Phe Val Gly Thr Ala His Tyr Ala Gln
1               5                   10                  15

Lys Phe Gln Gly
```

20

<210> SEQ ID NO 126
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 126

Trp Met Gly Gly Ile Ile Pro Ile Phe Gly Ser Ala Asn Tyr Ala Gln
1               5                   10                  15

Lys Phe Gln Gly
            20

<210> SEQ ID NO 127
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 127

Trp Met Gly Gly Ile Ile Pro Ile Phe Gly Thr Ala Asn Tyr Ala Gln
1               5                   10                  15

Lys Phe Gln Gly
            20

<210> SEQ ID NO 128
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 128

Trp Met Gly Gly Ile Ile Pro Ile Phe Gly Ile Ala Lys Tyr Ala Gln
1               5                   10                  15

Lys Phe Gln Gly
            20

<210> SEQ ID NO 129
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 129

Trp Met Gly Trp Ile Asn Pro Asn Asn Gly Asn Thr Arg Tyr Ala Gln
1               5                   10                  15

Lys Phe Gln Gly
            20

<210> SEQ ID NO 130
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 130

Trp Met Gly Gly Ile Ile Pro Ile Phe Gly Thr Ala Asn Tyr Ala Gln
1               5                   10                  15

Lys Phe Gln Gly
            20

<210> SEQ ID NO 131
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 131

Trp Met Gly Gly Ile Ile Pro Ile Phe Gly Ile Ala Lys Tyr Ala Gln
1               5                   10                  15

Lys Phe Gln Gly
            20

<210> SEQ ID NO 132
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 132

Trp Met Gly Gly Ile Ile Pro His Phe Gly Thr Ala Asn Tyr Ala Gln
1               5                   10                  15

Lys Phe Gln Gly
            20

<210> SEQ ID NO 133
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 133

Trp Met Gly Gly Ile His Pro Ala Phe Gly Thr Ala Thr Tyr Ala Gln
1               5                   10                  15

Lys Phe Gln Gly
            20

<210> SEQ ID NO 134
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 134

Trp Met Gly Gly Ile Ile Pro Ile Phe Gly Thr Ala Asn Tyr Ala Gln
1               5                   10                  15

Lys Phe Gln Gly
            20

<210> SEQ ID NO 135
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 135

Trp Met Gly Gly Ile Tyr Pro Ile Phe Gly Tyr Ala Asn Tyr Ala Gln
1               5                   10                  15

Lys Phe Gln Gly
         20

<210> SEQ ID NO 136
<211> LENGTH: 22
<212> TYPE: PRT
<213> ORGANISM: Artificial Sequence
<220> FEATURE:
<223> OTHER INFORMATION: synthetic affinity ligand peptide sequence

<400> SEQUENCE: 136

Trp Val Gly Arg Ile Lys Ser Lys Thr Asn Gly Gly Thr Thr Asp Tyr
1               5                   10                  15

Ala Ala Pro Val Lys Gly
         20

<210> SEQ ID NO 137
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 137

Trp Met Gly Gly Ile Ala Pro Ile Phe Gly Thr Ala Asn Tyr Ala Gln
1               5                   10                  15

Lys Phe Gln Gly
         20

<210> SEQ ID NO 138
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 138

Trp Met Gly Gly Ile Ile Pro His Phe Gly Thr Ala Ser Tyr Ala Gln
1               5                   10                  15

Lys Phe Gln Gly
         20

<210> SEQ ID NO 139
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 139

Trp Met Gly Gly Ile Ile Pro Ile Phe Gly Thr Ala Asn Tyr Ala Gln
1               5                   10                  15

Lys Phe Gln Gly
         20

<210> SEQ ID NO 140
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 140

Trp Met Gly Gly Ile Ile Pro Asn Phe Gly Thr Ala His Tyr Ala Gln

```
1               5                   10                  15

Lys Phe Gln Gly
            20

<210> SEQ ID NO 141
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 141

Trp Met Gly Gly Ile Ile Pro His Phe Gly Thr Ala Asn Tyr Ala Gln
1               5                   10                  15

Lys Phe Gln Gly
            20

<210> SEQ ID NO 142
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 142

Trp Met Gly Gly Ile Ile Pro Ile Phe Gly Ala Ala Thr Tyr Ala Gln
1               5                   10                  15

Lys Phe Gln Gly
            20

<210> SEQ ID NO 143
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 143

Asp Ser Ser Ser Ile Glu Tyr Phe Asp Val
1               5                   10

<210> SEQ ID NO 144
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 144

Gly His Arg Tyr Thr Asp Gly Phe Ala Tyr
1               5                   10

<210> SEQ ID NO 145
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 145

Asp Arg Ser Ile Tyr Ser Tyr Phe Asp Tyr
1               5                   10

<210> SEQ ID NO 146
<211> LENGTH: 9
```

```
<212> TYPE: PRT
<213> ORGANISM: Artificial Sequence
<220> FEATURE:
<223> OTHER INFORMATION: synthetic affinity ligand peptide sequence

<400> SEQUENCE: 146

His Gly Val Ser Glu Ala Phe Asp Tyr
1               5

<210> SEQ ID NO 147
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 147

Glu Val Asp Ser Ser Tyr Pro Glu Asp Tyr
1               5                   10

<210> SEQ ID NO 148
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 148

Asp Ile Arg Ile Ser Thr His Phe Asp Tyr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 149

Asn Ser Phe Tyr Ser Glu Trp Phe Asp Val
1               5                   10

<210> SEQ ID NO 150
<211> LENGTH: 17
<212> TYPE: PRT
<213> ORGANISM: Artificial Sequence
<220> FEATURE:
<223> OTHER INFORMATION: synthetic affinity ligand peptide sequence

<400> SEQUENCE: 150

Val Leu Tyr Ser Ser Tyr Tyr Gly Met Gly His Tyr Glu Tyr Phe Asp
1               5                   10                  15

Ile

<210> SEQ ID NO 151
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 151

Asp Ile Arg Ile Ser Thr His Phe Asp Tyr
1               5                   10

<210> SEQ ID NO 152
```

```
<211> LENGTH: 16
<212> TYPE: PRT
<213> ORGANISM: Artificial Sequence
<220> FEATURE:
<223> OTHER INFORMATION: synthetic affinity ligand peptide sequence

<400> SEQUENCE: 152

His Ser Tyr Ser Thr Gly Leu Tyr Met Gly Ser Asp Tyr Met Asp Tyr
1               5                   10                  15

<210> SEQ ID NO 153
<211> LENGTH: 14
<212> TYPE: PRT
<213> ORGANISM: Artificial Sequence
<220> FEATURE:
<223> OTHER INFORMATION: synthetic affinity ligand peptide sequence

<400> SEQUENCE: 153

His Ala Gly Tyr Gly Ala Ser Gly Tyr Glu Tyr Met Asp Asn
1               5                   10

<210> SEQ ID NO 154
<211> LENGTH: 19
<212> TYPE: PRT
<213> ORGANISM: Artificial Sequence
<220> FEATURE:
<223> OTHER INFORMATION: synthetic affinity ligand peptide sequence

<400> SEQUENCE: 154

Asp Val Ser Ser Tyr Tyr Tyr Gly Phe His Tyr His Ala Tyr Trp
1               5                   10                  15

Phe Asp Val

<210> SEQ ID NO 155
<211> LENGTH: 7
<212> TYPE: PRT
<213> ORGANISM: Artificial Sequence
<220> FEATURE:
<223> OTHER INFORMATION: synthetic affinity ligand peptide sequence

<400> SEQUENCE: 155

Asp Ser Asp Tyr Phe Asp Tyr
1               5

<210> SEQ ID NO 156
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 156

Ser Lys Gly Arg Gly Leu Tyr Gln Asn Ile Gln Asp Tyr
1               5                   10

<210> SEQ ID NO 157
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 157

Gly His Tyr Ile Ser Ser Tyr Ala Phe Asp Val
1               5                   10
```

```
<210> SEQ ID NO 158
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 158

Asp Ile Arg Ile Ser Thr His Phe Asp Tyr
1               5                   10

<210> SEQ ID NO 159
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 159

Asp Phe Tyr Asp Gly Phe Asp Tyr
1               5

<210> SEQ ID NO 160
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 160

Asp Glu Tyr Val Gly His Tyr Phe Asp His
1               5                   10

<210> SEQ ID NO 161
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 161

Glu Pro Ile Val Asn Ser Ser Pro Met Ala Val
1               5                   10

<210> SEQ ID NO 162
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 162

Gln Glu Tyr Ser Tyr Tyr Asn Phe Asp Pro
1               5                   10

<210> SEQ ID NO 163
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 163

Arg Ala Ser Gln Ser Ile Asn Thr Tyr Leu Ala
1               5                   10

<210> SEQ ID NO 164
```

```
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 164

Arg Ala Ser Gln Gly Ile Ser Asn His Leu Asn
1               5                   10

<210> SEQ ID NO 165
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 165

Ser Gly Ser Ser Ser Asn Ile Gly Lys Asn Tyr Val His
1               5                   10

<210> SEQ ID NO 166
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 166

Arg Ala Ser Gln Ser Ile Ser Asn Tyr Leu Asn
1               5                   10

<210> SEQ ID NO 167
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 167

Arg Ala Ser Gln Asp Ile Met Leu Asn Leu Asn
1               5                   10

<210> SEQ ID NO 168
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 168

Arg Ala Ser Gln Ser Ile Arg Asn Tyr Leu Ala
1               5                   10

<210> SEQ ID NO 169
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 169

Arg Ala Ser Gln Ser Ile Asn Ser Tyr Leu Ala
1               5                   10

<210> SEQ ID NO 170
<211> LENGTH: 12
```

```
<212> TYPE: PRT
<213> ORGANISM: Artificial Sequence
<220> FEATURE:
<223> OTHER INFORMATION: synthetic affinity ligand peptide sequence

<400> SEQUENCE: 170

Arg Ala Ser Gln Ile Val Ser Ser Ser Tyr Leu Val
1               5                   10

<210> SEQ ID NO 171
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 171

Arg Ala Ser Gln Gly Ile Leu Ser Phe Leu Thr
1               5                   10

<210> SEQ ID NO 172
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 172

Arg Ala Ser Gln Asp Ile Ser Arg Tyr Leu Asn
1               5                   10

<210> SEQ ID NO 173
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 173

Arg Ala Ser Gln Ser Ile Ile Lys Tyr Leu Ala
1               5                   10

<210> SEQ ID NO 174
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 174

Ser Gly Asp Asn Ile Arg Lys Lys Tyr Val His
1               5                   10

<210> SEQ ID NO 175
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 175

Arg Ala Ser Gln Asp Ile Arg Asn Tyr Leu Asn
1               5                   10

<210> SEQ ID NO 176
<211> LENGTH: 11
<212> TYPE: PRT
```

```
<213> ORGANISM: Artificial Sequence
<220> FEATURE:
<223> OTHER INFORMATION: synthetic affinity ligand peptide sequence

<400> SEQUENCE: 176

Ser Gly Asp Lys Ile Gly Asp Lys Tyr Ala Asp
1               5                   10

<210> SEQ ID NO 177
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 177

Ser Gly Asp Lys Leu Gly Ser Ser Tyr Ala Thr
1               5                   10

<210> SEQ ID NO 178
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 178

Arg Ala Ser Gln Ser Ile Arg Asn Tyr Leu Ala
1               5                   10

<210> SEQ ID NO 179
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 179

Arg Ala Ser Gln Ser Ile Lys Thr Tyr Leu Ala
1               5                   10

<210> SEQ ID NO 180
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 180

Arg Ala Ser Gln Ser Ile Phe Asn Tyr Leu Asn
1               5                   10

<210> SEQ ID NO 181
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 181

Arg Ala Ser Gln Ser Ile Ser Ser Tyr Leu Asn
1               5                   10

<210> SEQ ID NO 182
<211> LENGTH: 11
<212> TYPE: PRT
<213> ORGANISM: Artificial Sequence
```

```
<220> FEATURE:
<223> OTHER INFORMATION: synthetic affinity ligand peptide sequence

<400> SEQUENCE: 182

Arg Ala Ser Gln Ser Ile Asn Asn Tyr Leu Asn
1               5                   10

<210> SEQ ID NO 183
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 183

Leu Leu Ile Ser Gly Ala Ser Ser Leu Gln Ser
1               5                   10

<210> SEQ ID NO 184
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 184

Leu Leu Ile Tyr Gly Ala Ser Ser Leu Gln Ser
1               5                   10

<210> SEQ ID NO 185
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 185

Val Leu Ile Tyr Arg Asp Asn Gln Arg Pro Ser
1               5                   10

<210> SEQ ID NO 186
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 186

Leu Leu Ile Tyr Asp Ala Ser Ser Leu Gln Ser
1               5                   10

<210> SEQ ID NO 187
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 187

Leu Leu Ile Tyr Ala Thr Ser Ser Leu Gln Ser
1               5                   10

<210> SEQ ID NO 188
<211> LENGTH: 11
<212> TYPE: PRT
<213> ORGANISM: Artificial Sequence
<220> FEATURE:
```

<223> OTHER INFORMATION: synthetic affinity ligand peptide sequence

<400> SEQUENCE: 188

Leu Leu Ile Tyr Asp Ala Ser Ser Leu Gln Ser
1               5                   10

<210> SEQ ID NO 189
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 189

Leu Leu Ile Tyr Ala Ala Ser Asn Leu Gln Ser
1               5                   10

<210> SEQ ID NO 190
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 190

Leu Leu Ile Tyr Gly Ala Ser Ser Arg Ala Thr
1               5                   10

<210> SEQ ID NO 191
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 191

Leu Leu Ile Tyr Asp Ala Ser Ser Leu Gln Ser
1               5                   10

<210> SEQ ID NO 192
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 192

Leu Leu Ile Tyr Gly Ala Ser Asn Leu Gln Ser
1               5                   10

<210> SEQ ID NO 193
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 193

Leu Leu Ile Tyr Gly Ala Ser Lys Leu Gln Ser
1               5                   10

<210> SEQ ID NO 194
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 194

Leu Val Ile Tyr Asp Asp Asn Glu Arg Pro Ser
1               5                   10

<210> SEQ ID NO 195
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 195

Leu Leu Ile Tyr Gln Val Ser Thr Gln Gln Ser
1               5                   10

<210> SEQ ID NO 196
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 196

Leu Val Ile Tyr Arg Asp Ser Asn Arg Pro Ser
1               5                   10

<210> SEQ ID NO 197
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 197

Leu Val Ile Tyr Glu Gln Ser Lys Arg Pro Ser
1               5                   10

<210> SEQ ID NO 198
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 198

Leu Leu Ile Tyr Asp Ala Ser Ser Leu Gln Ser
1               5                   10

<210> SEQ ID NO 199
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 199

Leu Leu Ile Tyr Ala Val Ser Ser Leu Gln Ser
1               5                   10

<210> SEQ ID NO 200
<211> LENGTH: 11
<212> TYPE: PRT
<213> ORGANISM: Artificial Sequence
<220> FEATURE:
<223> OTHER INFORMATION: synthetic affinity ligand peptide sequence

```
<400> SEQUENCE: 200

Leu Leu Ile Tyr Ala Ala Ser Arg Leu Gln Ser
1               5                   10

<210> SEQ ID NO 201
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 201

Leu Leu Ile His Asp Ala Ser Ser Leu Gln Ser
1               5                   10

<210> SEQ ID NO 202
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 202

Leu Leu Ile Tyr Gln Ala Ser Arg Leu Gln Ser
1               5                   10

<210> SEQ ID NO 203
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 203

Gln Gln Ala Tyr Thr Arg Ser Phe
1               5

<210> SEQ ID NO 204
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 204

Gln Gln Glu Tyr Ser Ser Pro Ile
1               5

<210> SEQ ID NO 205
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 205

Gln Ala Tyr Asp Leu Leu Ser Arg Arg Trp
1               5                   10

<210> SEQ ID NO 206
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 206
```

```
Gln Gln Tyr Tyr His Phe Pro Ile
1               5

<210> SEQ ID NO 207
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 207

Gln Gln Arg Ser His Trp Ser Asn
1               5

<210> SEQ ID NO 208
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 208

His Gln Tyr Tyr Ser Thr Pro Leu
1               5

<210> SEQ ID NO 209
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 209

Gln Gln Tyr Tyr Ser Trp Pro Ile
1               5

<210> SEQ ID NO 210
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 210

Gln Gln Ala Asp Gln Tyr Pro Met
1               5

<210> SEQ ID NO 211
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 211

His Gln Tyr Tyr Ser Thr Pro Leu
1               5

<210> SEQ ID NO 212
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 212
```

```
Gln Gln Ala Tyr Ser Thr Pro Val
1               5
```

<210> SEQ ID NO 213
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 213

```
Gln Gln Tyr Tyr Ser Tyr Pro Ala
1               5
```

<210> SEQ ID NO 214
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 214

```
Gln Val Ala Thr Tyr Leu Asn Arg
1               5
```

<210> SEQ ID NO 215
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 215

```
Gln Gln Ala Tyr Ser Asn Pro His
1               5
```

<210> SEQ ID NO 216
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 216

```
Ala Ser Tyr Asp Trp His Met Ile His Tyr
1               5                   10
```

<210> SEQ ID NO 217
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 217

```
Gln Val Trp Thr Arg Thr Gln Tyr
1               5
```

<210> SEQ ID NO 218
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 218

```
His Gln Tyr Tyr Ser Thr Pro Leu
```

```
1               5
```

<210> SEQ ID NO 219
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 219

```
Met Gln Ser Tyr Ser Ser Pro Tyr
1               5
```

<210> SEQ ID NO 220
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 220

```
Gln Gln Met Tyr Asp Lys Pro Phe
1               5
```

<210> SEQ ID NO 221
<211> LENGTH: 7
<212> TYPE: PRT
<213> ORGANISM: Artificial Sequence
<220> FEATURE:
<223> OTHER INFORMATION: synthetic affinity ligand peptide sequence

<400> SEQUENCE: 221

```
Gln Gln Ser Leu Gln Tyr Tyr
1               5
```

<210> SEQ ID NO 222
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 222

```
Gln Gln Gly Tyr Ser Ser Pro Phe
1               5
```

<210> SEQ ID NO 223
<211> LENGTH: 12
<212> TYPE: PRT
<213> ORGANISM: Artificial Sequence
<220> FEATURE:
<223> OTHER INFORMATION: synthetic affinity ligand peptide sequence

<400> SEQUENCE: 223

```
Gly Asp Ser Val Ser Asp Ser Ser Ala Ala Trp Asn
1               5                   10
```

<210> SEQ ID NO 224
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 224

```
Gly Phe Thr Phe Ser Arg Tyr Gly Met Asn
1               5                   10
```

<210> SEQ ID NO 225
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 225

Gly Phe Thr Phe Gly Asp Tyr Trp Ile His
1               5                   10

<210> SEQ ID NO 226
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 226

Gly Phe Thr Phe Ser Arg Tyr Ala Met Ser
1               5                   10

<210> SEQ ID NO 227
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 227

Gly Gly Thr Phe Ser Gly Tyr Ala Ile Ser
1               5                   10

<210> SEQ ID NO 228
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 228

Gly Tyr Ser Phe Thr Thr Tyr Thr Ile Ser
1               5                   10

<210> SEQ ID NO 229
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 229

Gly Phe Thr Phe Ser Ser Tyr Gly Met His
1               5                   10

<210> SEQ ID NO 230
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 230

Gly Phe Thr Phe Ser Ser Phe Ala Leu Thr
1               5                   10

```
<210> SEQ ID NO 231
<211> LENGTH: 21
<212> TYPE: PRT
<213> ORGANISM: Artificial Sequence
<220> FEATURE:
<223> OTHER INFORMATION: synthetic affinity ligand peptide sequence

<400> SEQUENCE: 231

Trp Leu Gly Arg Ile Tyr Tyr Arg Ser Lys Trp Tyr Asn Asp Tyr Ala
1               5                   10                  15

Val Ser Val Lys Ser
            20

<210> SEQ ID NO 232
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 232

Trp Val Ser Gly Ile Ser Gly Ser Gly Ser Tyr Thr Tyr Tyr Ala Asp
1               5                   10                  15

Ser Val Lys Gly
            20

<210> SEQ ID NO 233
<211> LENGTH: 19
<212> TYPE: PRT
<213> ORGANISM: Artificial Sequence
<220> FEATURE:
<223> OTHER INFORMATION: synthetic affinity ligand peptide sequence

<400> SEQUENCE: 233

Trp Val Ser Ser Ile Ser Gly Gly Asn Thr Tyr Tyr Ala Asp Ser
1               5                   10                  15

Val Lys Gly

<210> SEQ ID NO 234
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 234

Trp Val Ser Ser Ile Ser Tyr Lys Gly Ser Asn Thr Tyr Tyr Ala Asp
1               5                   10                  15

Ser Val Lys Gly
            20

<210> SEQ ID NO 235
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 235

Trp Met Gly Arg Ile Phe Pro Arg Ser Gly Phe Ala Asn Tyr Ala Gln
1               5                   10                  15

Lys Phe Gln Gly
            20
```

<210> SEQ ID NO 236
<211> LENGTH: 20
<212> TYPE: PRT
<213> ORGANISM: Artificial Sequence
<220> FEATURE:
<223> OTHER INFORMATION: synthetic affinity ligand peptide sequence

<400> SEQUENCE: 236

Trp Met Gly Ile Ile Tyr Pro Ser Asp Ser Asp Thr Ile Tyr Ser Pro
1               5                   10                  15

Ser Phe Gln Gly
            20

<210> SEQ ID NO 237
<211> LENGTH: 22
<212> TYPE: PRT
<213> ORGANISM: Artificial Sequence
<220> FEATURE:
<223> OTHER INFORMATION: synthetic affinity ligand peptide sequence

<400> SEQUENCE: 237

Trp Val Gly Arg Ile Lys Ser Lys Met Asn Gly Gly Thr Thr Asp Tyr
1               5                   10                  15

Ala Ala Pro Val Lys Gly
            20

<210> SEQ ID NO 238
<211> LENGTH: 22
<212> TYPE: PRT
<213> ORGANISM: Artificial Sequence
<220> FEATURE:
<223> OTHER INFORMATION: synthetic affinity ligand peptide sequence

<400> SEQUENCE: 238

Trp Val Gly Phe Ile Lys Ser Lys Thr His Gly Gly Thr Thr Asp Tyr
1               5                   10                  15

Ala Ala Pro Val Lys Gly
            20

<210> SEQ ID NO 239
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 239

Glu Ser Pro Ala Asp Val Ser Gly Ile Asn Phe Asp Ile
1               5                   10

<210> SEQ ID NO 240
<211> LENGTH: 12
<212> TYPE: PRT
<213> ORGANISM: Artificial Sequence
<220> FEATURE:
<223> OTHER INFORMATION: synthetic affinity ligand peptide sequence

<400> SEQUENCE: 240

Arg Ser Arg Tyr Pro Tyr Val Tyr Val Phe Asp Tyr
1               5                   10

<210> SEQ ID NO 241
<211> LENGTH: 12
<212> TYPE: PRT
<213> ORGANISM: Artificial Sequence

```
<220> FEATURE:
<223> OTHER INFORMATION: synthetic affinity ligand peptide sequence

<400> SEQUENCE: 241

Ser Leu Tyr Trp Arg Tyr Ser Ser Tyr Phe Asp Pro
1               5                   10

<210> SEQ ID NO 242
<211> LENGTH: 15
<212> TYPE: PRT
<213> ORGANISM: Artificial Sequence
<220> FEATURE:
<223> OTHER INFORMATION: synthetic affinity ligand peptide sequence

<400> SEQUENCE: 242

Ala Pro Tyr Pro Gly Ser Val Ser Arg Tyr Gly Ala Phe Asp Tyr
1               5                   10                  15

<210> SEQ ID NO 243
<211> LENGTH: 14
<212> TYPE: PRT
<213> ORGANISM: Artificial Sequence
<220> FEATURE:
<223> OTHER INFORMATION: synthetic affinity ligand peptide sequence

<400> SEQUENCE: 243

Asp Val Ser Gly Val Thr Gly Tyr Arg Lys Ala Arg Asp Tyr
1               5                   10

<210> SEQ ID NO 244
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 244

Ser Ser Val Val Gly Phe Asp Val
1               5

<210> SEQ ID NO 245
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 245

Ser Leu Thr Ser Gly Phe Asp Tyr
1               5

<210> SEQ ID NO 246
<211> LENGTH: 7
<212> TYPE: PRT
<213> ORGANISM: Artificial Sequence
<220> FEATURE:
<223> OTHER INFORMATION: synthetic affinity ligand peptide sequence

<400> SEQUENCE: 246

Asn Arg Gly His Phe Asp Tyr
1               5

<210> SEQ ID NO 247
<211> LENGTH: 11
<212> TYPE: PRT
<213> ORGANISM: Artificial Sequence
<220> FEATURE:
```

<223> OTHER INFORMATION: synthetic affinity ligand peptide sequence

<400> SEQUENCE: 247

Arg Ala Ser Gln Ser Ile Tyr Ser His Leu Ala
1               5                   10

<210> SEQ ID NO 248
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 248

Ser Gly Ser Ser Ser Asn Ile Gly Ser Tyr Tyr Val Asn
1               5                   10

<210> SEQ ID NO 249
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 249

Arg Ala Ser Gln Thr Ile Ser Asn His Leu Asn
1               5                   10

<210> SEQ ID NO 250
<211> LENGTH: 14
<212> TYPE: PRT
<213> ORGANISM: Artificial Sequence
<220> FEATURE:
<223> OTHER INFORMATION: synthetic affinity ligand peptide sequence

<400> SEQUENCE: 250

Thr Gly Ser Ser Ser Asn Ile Gly Ala Gly Tyr Tyr Val His
1               5                   10

<210> SEQ ID NO 251
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 251

Arg Ala Ser Gln Gly Ile Arg Thr Arg Leu Lys
1               5                   10

<210> SEQ ID NO 252
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 252

Arg Ala Ser Gln Ser Ile Ser Ser Tyr Leu Asn
1               5                   10

<210> SEQ ID NO 253
<211> LENGTH: 11
<212> TYPE: PRT
<213> ORGANISM: Artificial Sequence
<220> FEATURE:
<223> OTHER INFORMATION: synthetic affinity ligand peptide sequence

```
<400> SEQUENCE: 253

Ser Gly Asp Asn Leu Arg Asp Lys Tyr Val Tyr
1               5                   10

<210> SEQ ID NO 254
<211> LENGTH: 13
<212> TYPE: PRT
<213> ORGANISM: Artificial Sequence
<220> FEATURE:
<223> OTHER INFORMATION: synthetic affinity ligand peptide sequence

<400> SEQUENCE: 254

Ser Gly Ser Ser Ser Asn Ile Gly Ala Tyr Tyr Val Tyr
1               5                   10

<210> SEQ ID NO 255
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 255

Leu Leu Ile Tyr Ala Ala Ser Asn Leu Gln Ser
1               5                   10

<210> SEQ ID NO 256
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 256

Leu Leu Ile Tyr Arg Asn Asn Gln Arg Pro Ser
1               5                   10

<210> SEQ ID NO 257
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 257

Leu Leu Ile Tyr Ala Ala Ser Ser Leu Gln Ser
1               5                   10

<210> SEQ ID NO 258
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 258

Leu Leu Ile Tyr Gly Asn Asn Gln Arg Pro Ser
1               5                   10

<210> SEQ ID NO 259
<211> LENGTH: 11
<212> TYPE: PRT
<213> ORGANISM: Artificial Sequence
<220> FEATURE:
<223> OTHER INFORMATION: synthetic affinity ligand peptide sequence
```

```
<400> SEQUENCE: 259

Leu Leu Ile Tyr Gly Ala Ser Thr Leu Gln Ser
1               5                   10

<210> SEQ ID NO 260
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 260

Leu Leu Ile Tyr Ala Ala Ser Arg Leu Gln Ser
1               5                   10

<210> SEQ ID NO 261
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 261

Leu Val Ile Tyr Ser Asn Ser Asn Arg Pro Ser
1               5                   10

<210> SEQ ID NO 262
<211> LENGTH: 11
<212> TYPE: PRT
<213> ORGANISM: Artificial Sequence
<220> FEATURE:
<223> OTHER INFORMATION: synthetic affinity ligand peptide sequence

<400> SEQUENCE: 262

Leu Leu Ile Tyr Gly Asn Asn Gln Arg Pro Ser
1               5                   10

<210> SEQ ID NO 263
<211> LENGTH: 7
<212> TYPE: PRT
<213> ORGANISM: Artificial Sequence
<220> FEATURE:
<223> OTHER INFORMATION: synthetic affinity ligand peptide sequence

<400> SEQUENCE: 263

Gln Gln Ser Asp Glu Ser Ile
1               5

<210> SEQ ID NO 264
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 264

Ser Ala Tyr Thr Gly Leu Ser Ser Ser Pro
1               5                   10

<210> SEQ ID NO 265
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 265
```

```
Gln Gln Ser Leu His Tyr Pro Tyr
1               5

<210> SEQ ID NO 266
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 266

Gly Ala Arg Asp Phe Gln Leu Ser Ser Trp
1               5                   10

<210> SEQ ID NO 267
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 267

Gln Gln Gln Asp Gln Thr Pro Tyr
1               5

<210> SEQ ID NO 268
<211> LENGTH: 8
<212> TYPE: PRT
<213> ORGANISM: Artificial Sequence
<220> FEATURE:
<223> OTHER INFORMATION: synthetic affinity ligand peptide sequence

<400> SEQUENCE: 268

Gln Gln His Leu Ser Trp Pro Glu
1               5

<210> SEQ ID NO 269
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 269

Tyr Ala Trp Ala Arg Arg His Thr Gly Ala
1               5                   10

<210> SEQ ID NO 270
<211> LENGTH: 10
<212> TYPE: PRT
<213> ORGANISM: Artificial Sequence
<220> FEATURE:
<223> OTHER INFORMATION: synthetic affinity ligand peptide sequence

<400> SEQUENCE: 270

Tyr Ser Trp Asp His Met Leu Asn Gly Tyr
1               5                   10

<210> SEQ ID NO 271
<211> LENGTH: 245
<212> TYPE: PRT
<213> ORGANISM: Artificial Sequence
<220> FEATURE:
<223> OTHER INFORMATION: synthetic affinity ligand peptide sequence

<400> SEQUENCE: 271
```

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ser Ile Ser Tyr Lys Gly Ser Asn Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Pro Tyr Pro Gly Ser Val Ser Arg Tyr Gly Ala Phe Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
    210                 215                 220

Lys Ser Glu Phe Asp Tyr Lys Asp Asp Asp Lys Gly Ala Pro His
225                 230                 235                 240

His His His His His
            245

<210> SEQ ID NO 272
<211> LENGTH: 216
<212> TYPE: PRT
<213> ORGANISM: Artificial Sequence
<220> FEATURE:
<223> OTHER INFORMATION: synthetic affinity ligand peptide sequence

<400> SEQUENCE: 272

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Tyr Val His Trp Tyr Gln Gln Leu Pro Gly Thr Ala Pro Lys Leu
        35                  40                  45

Leu Ile Tyr Gly Asn Asn Gln Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gly Ala Arg Asp Phe Gln
                85                  90                  95

Leu Ser Ser Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Ala
            210                 215

<210> SEQ ID NO 273
<211> LENGTH: 239
<212> TYPE: PRT
<213> ORGANISM: Artificial Sequence
<220> FEATURE:
<223> OTHER INFORMATION: synthetic affinity ligand peptide sequence

<400> SEQUENCE: 273

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Ala Leu Thr Trp Val Arg Gln Ala Pro Gly Lys Gly Leu Glu Trp Val
            35                  40                  45

Gly Phe Ile Lys Ser Lys Thr His Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asn Arg Gly His Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Thr Lys Ser Glu Phe Asp Tyr
            210                 215                 220

Lys Asp Asp Asp Asp Lys Gly Ala Pro His His His His His His
225                 230                 235

<210> SEQ ID NO 274
<211> LENGTH: 215

```
<212> TYPE: PRT
<213> ORGANISM: Artificial Sequence
<220> FEATURE:
<223> OTHER INFORMATION: synthetic affinity ligand peptide sequence

<400> SEQUENCE: 274

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ala Tyr
            20                  25                  30

Tyr Val Tyr Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Tyr Ser Trp Asp His Met Leu
                85                  90                  95

Asn Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 275
<211> LENGTH: 240
<212> TYPE: PRT
<213> ORGANISM: Artificial Sequence
<220> FEATURE:
<223> OTHER INFORMATION: synthetic affinity ligand peptide sequence

<400> SEQUENCE: 275

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Gly Arg Ile Lys Ser Lys Met Asn Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ser Leu Thr Ser Gly Phe Asp Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Glu Phe Asp
210                 215                 220

Tyr Lys Asp Asp Asp Lys Gly Ala Pro His His His His His His
225                 230                 235                 240

<210> SEQ ID NO 276
<211> LENGTH: 213
<212> TYPE: PRT
<213> ORGANISM: Artificial Sequence
<220> FEATURE:
<223> OTHER INFORMATION: synthetic affinity ligand peptide sequence

<400> SEQUENCE: 276

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Arg Asp Lys Tyr Val
            20                  25                  30

Tyr Trp Tyr Gln Gln Lys Pro Gly Gln Ala Pro Val Leu Val Ile Tyr
        35                  40                  45

Ser Asn Ser Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Tyr Ala Trp Ala Arg Arg His Thr Gly
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
        210

<210> SEQ ID NO 277
```

```
<211> LENGTH: 244
<212> TYPE: PRT
<213> ORGANISM: Artificial Sequence
<220> FEATURE:
<223> OTHER INFORMATION: synthetic affinity ligand peptide sequence

<400> SEQUENCE: 277

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
                20                  25                  30

Ala Ile Ser Trp Val Arg Gln Ala Pro Gly Gln Gly Leu Glu Trp Met
            35                  40                  45

Gly Arg Ile Phe Pro Arg Ser Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Ser Gly Val Thr Gly Tyr Arg Lys Ala Arg Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Glu Phe Asp Tyr Lys Asp Asp Asp Lys Gly Ala Pro His His
225                 230                 235                 240

His His His His

<210> SEQ ID NO 278
<211> LENGTH: 214
<212> TYPE: PRT
<213> ORGANISM: Artificial Sequence
<220> FEATURE:
<223> OTHER INFORMATION: synthetic affinity ligand peptide sequence

<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Thr Arg
                20                  25                  30

Leu Lys Trp Tyr Gln Gln Lys Pro Gly Lys Ala Pro Lys Leu Leu Ile
            35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Asp Gln Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210
```

<210> SEQ ID NO 279
<211> LENGTH: 241
<212> TYPE: PRT
<213> ORGANISM: Artificial Sequence
<220> FEATURE:
<223> OTHER INFORMATION: synthetic affinity ligand peptide sequence

<400> SEQUENCE: 279

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Trp Ile His Trp Val Arg Gln Ala Pro Gly Lys Gly Leu Glu Trp Val
        35                  40                  45

Ser Ser Ile Ser Gly Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Leu Tyr Trp Arg Tyr Ser Ser Tyr Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220
```

```
Asp Tyr Lys Asp Asp Asp Lys Gly Ala Pro His His His His
225                 230                 235                 240

His

<210> SEQ ID NO 280
<211> LENGTH: 214
<212> TYPE: PRT
<213> ORGANISM: Artificial Sequence
<220> FEATURE:
<223> OTHER INFORMATION: synthetic affinity ligand peptide sequence

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn His
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu His Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210

<210> SEQ ID NO 281
<211> LENGTH: 246
<212> TYPE: PRT
<213> ORGANISM: Artificial Sequence
<220> FEATURE:
<223> OTHER INFORMATION: synthetic affinity ligand peptide sequence

<400> SEQUENCE: 281

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Asp Ser
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
50                  55                  60
```

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Ser Pro Ala Asp Val Ser Gly Ile Asn Phe
            100                 105                 110

Asp Ile Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Glu Phe Asp Tyr Lys Asp Asp Asp Lys Gly Ala Pro
225                 230                 235                 240

His His His His His His
                245

<210> SEQ ID NO 282
<211> LENGTH: 213
<212> TYPE: PRT
<213> ORGANISM: Artificial Sequence
<220> FEATURE:
<223> OTHER INFORMATION: synthetic affinity ligand peptide sequence

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Ser His
                20                  25                  30

Leu Ala Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Glu Ser Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Ala
        210

<210> SEQ ID NO 283
<211> LENGTH: 240
<212> TYPE: PRT
<213> ORGANISM: Artificial Sequence
<220> FEATURE:
<223> OTHER INFORMATION: synthetic affinity ligand peptide sequence

<400> SEQUENCE: 283

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asp Val Ser Trp Val Arg Gln Ala Pro Gly Gln Gly Leu Glu Trp Met
            35                  40                  45

Gly Ile Ile Asn Pro Tyr Asn Gly Lys Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Lys Pro Val Gly Ala Arg Tyr Phe Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Glu Phe Asp
    210                 215                 220

Tyr Lys Asp Asp Asp Lys Gly Ala Pro His His His His His His
225                 230                 235                 240

<210> SEQ ID NO 284
<211> LENGTH: 216
<212> TYPE: PRT
<213> ORGANISM: Artificial Sequence
<220> FEATURE:
<223> OTHER INFORMATION: synthetic affinity ligand peptide sequence

<400> SEQUENCE: 284

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
```

```
                20                  25                  30
Tyr Val Val His Trp Tyr Gln Gln Leu Pro Gly Thr Ala Pro Lys Leu
            35                  40                  45
Leu Ile Tyr Asp Asn Asn Lys Arg Pro Ser Gly Val Pro Asp Arg Phe
 50                  55                  60
Ser Gly Ser Lys Ser Gly Thr Ser Ala Ser Leu Ala Ile Thr Gly Leu
 65                  70                  75                  80
Gln Ala Glu Asp Glu Ala Asp Tyr Tyr Cys Ala Ser Trp Asp Leu Gly
                85                  90                  95
Arg Lys Tyr Ser Val Phe Gly Gly Thr Lys Leu Thr Val Leu Gly
            100                 105                 110
Gln Pro Lys Ala Ala Pro Ser Val Thr Leu Phe Pro Pro Ser Ser Glu
            115                 120                 125
Glu Leu Gln Ala Asn Lys Ala Thr Leu Val Cys Leu Ile Ser Asp Phe
        130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Ala
    210                 215

<210> SEQ ID NO 285
<211> LENGTH: 244
<212> TYPE: PRT
<213> ORGANISM: Artificial Sequence
<220> FEATURE:
<223> OTHER INFORMATION: synthetic affinity ligand peptide sequence

<400> SEQUENCE: 285

Gln Val Gln Leu Val Gln Ser Gly Ala Glu Val Lys Lys Pro Gly Ala
 1               5                   10                  15
Ser Val Lys Val Ser Cys Lys Ala Ser Gly Tyr Thr Phe Thr Ser Tyr
            20                  25                  30
Asp Met His Trp Val Arg Gln Ala Pro Gly Gln Gly Leu Glu Trp Met
        35                  40                  45
Gly Trp Ile Asn Pro Tyr Asn Gly Gly Thr Lys Tyr Ala Gln Lys Phe
    50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Glu Asp Thr Ala Val Tyr Tyr Cys
                85                  90                  95
Ala Arg Ala Ser Tyr Gly Gly Tyr Ser His Val Tyr Ser Phe Asp Ile
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
```

```
                      165                 170                 175

Pro Ala Val Leu Gln Ser Ser Gly Leu Tyr Ser Leu Ser Val Val
                180                 185                 190

Thr Val Pro Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Glu Phe Asp Tyr Lys Asp Asp Asp Lys Gly Ala Pro His His
225                 230                 235                 240

His His His His

<210> SEQ ID NO 286
<211> LENGTH: 213
<212> TYPE: PRT
<213> ORGANISM: Artificial Sequence
<220> FEATURE:
<223> OTHER INFORMATION: synthetic affinity ligand peptide sequence

<400> SEQUENCE: 286

Asp Ile Glu Leu Thr Gln Pro Pro Ser Val Ser Val Ser Pro Gly Gln
1               5                   10                  15

Thr Ala Ser Ile Thr Cys Ser Gly Asp Lys Leu Arg Arg Lys Ile Val
                20                  25                  30

His Trp Tyr Gln Gln Lys Pro Gly Gln Ala Pro Val Leu Val Ile Tyr
            35                  40                  45

Ser Asp Thr Asp Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Arg Thr Leu Gly Pro Arg Ile
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 287
<211> LENGTH: 238
<212> TYPE: PRT
<213> ORGANISM: Artificial Sequence
<220> FEATURE:
<223> OTHER INFORMATION: synthetic affinity ligand peptide sequence

<400> SEQUENCE: 287

Glu Val Gln Leu Val Gln Ser Gly Ala Glu Val Lys Lys Pro Gly Glu
```

```
1               5                   10                  15
Ser Leu Lys Ile Ser Cys Lys Gly Ser Gly Tyr Ser Phe Thr Thr Tyr
            20                  25                  30

Thr Ile Ser Trp Val Arg Gln Met Pro Gly Lys Gly Leu Glu Trp Met
            35                  40                  45

Gly Ile Ile Tyr Pro Ser Asp Ser Asp Thr Ile Tyr Ser Pro Ser Phe
            50                  55                  60

Gln Gly Gln Val Thr Ile Ser Ala Asp Lys Ser Ile Ser Thr Ala Tyr
65                      70                  75                  80

Leu Gln Trp Ser Ser Leu Lys Ala Ser Asp Thr Ala Met Tyr Tyr Cys
                85                  90                  95

Ala Arg Ser Ser Val Val Gly Phe Asp Val Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Glu Phe Asp Tyr Lys
            210                 215                 220

Asp Asp Asp Asp Lys Gly Ala Pro His His His His His
225                 230                 235

<210> SEQ ID NO 288
<211> LENGTH: 214
<212> TYPE: PRT
<213> ORGANISM: Artificial Sequence
<220> FEATURE:
<223> OTHER INFORMATION: synthetic affinity ligand peptide sequence

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                      70                  75                  80

Glu Asp Phe Ala Thr Tyr Tyr Cys Gln Gln His Leu Ser Trp Pro Glu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
```

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Ala
    210
```